(12) United States Patent
Itoh

(10) Patent No.: US 8,211,120 B2
(45) Date of Patent: Jul. 3, 2012

(54) MANIPULATING HANDLE FOR SUCCESSIVE CLIPPING DEVICE, SUCCESSIVE CLIPPING DEVICE, MANIPULATING HANDLE FOR CLIPPING DEVICE, AND CLIPPING DEVICE

(75) Inventor: Koji Itoh, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 386 days.

(21) Appl. No.: 12/504,494

(22) Filed: Jul. 16, 2009

(65) Prior Publication Data

US 2010/0016867 A1 Jan. 21, 2010

(30) Foreign Application Priority Data

Jul. 17, 2008 (JP) ................................. 2008-186324
Aug. 18, 2008 (JP) ................................. 2008-209953
Aug. 28, 2008 (JP) ................................. 2008-219782

(51) Int. Cl.
*A61B 17/10* (2006.01)

(52) U.S. Cl. ........................................................ 606/142

(58) Field of Classification Search .......... 606/139–143, 606/205–211; 623/23.72; 227/175.1
See application file for complete search history.

(56) References Cited

U.S. PATENT DOCUMENTS

| 7,223,271 | B2 * | 5/2007 | Muramatsu et al. | 606/143 |
| 8,062,311 | B2 * | 11/2011 | Litscher et al. | 606/143 |
| 2002/0133178 | A1 | 9/2002 | Muramatsu et al. | |
| 2002/0177861 | A1 * | 11/2002 | Sugiyama et al. | 606/151 |

FOREIGN PATENT DOCUMENTS

| JP | 2002-191609 A | 7/2002 |
| JP | 2002-272751 A | 9/2002 |

* cited by examiner

*Primary Examiner* — Melanie Tyson
*Assistant Examiner* — Son Dang
(74) *Attorney, Agent, or Firm* — Birch, Stewart, Kolasch & Birch, LLP

(57) ABSTRACT

A manipulating handle for a successive clipping device comprises: a cylindrical handle main body connected to a sheath with a manipulating wire extending from the sheath being arranged in an interior thereof; a slider engaged with the manipulating wire for moving the manipulating wire in the axial direction of the handle main body; and a slider-movement-amount regulating member attached onto the outer circumferential surface of the handle main body so as to be rotatable in a circumferential direction of the handle main body, for regulating, according to a rotational position in a circumferential direction thereof, an amount of movement of the slider in the axial direction of the handle main body to one of a plurality of different amounts of movement required for respective clipping manipulations using a plurality of clips connected to the manipulating wire.

14 Claims, 31 Drawing Sheets

FIG.13
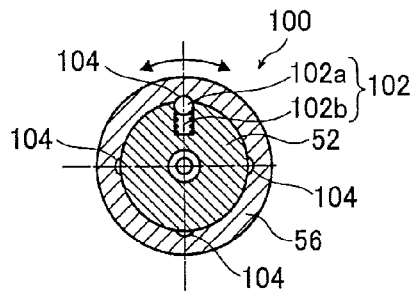
FIG.14A  FIG.14B
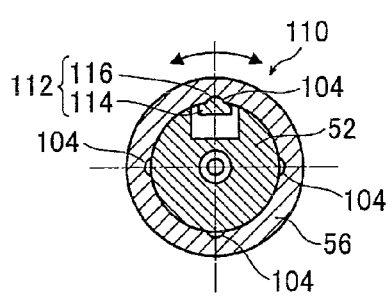 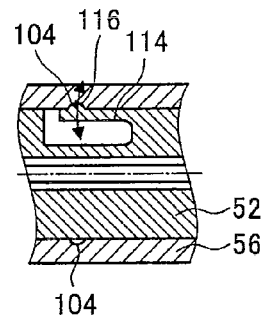
FIG.15A  FIG.15B
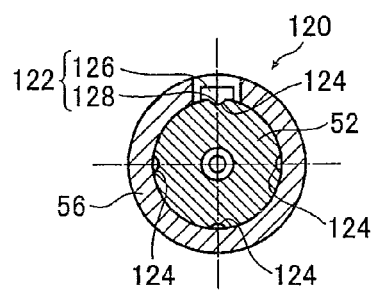 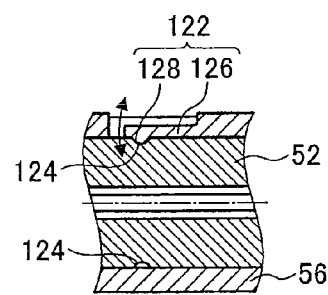
FIG.16A  FIG.16B
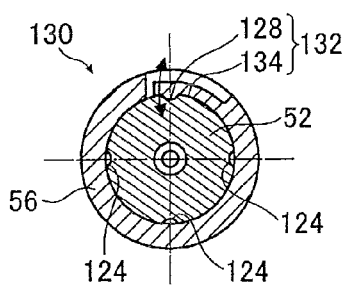 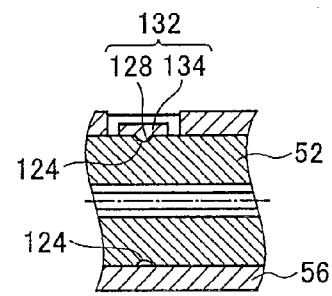

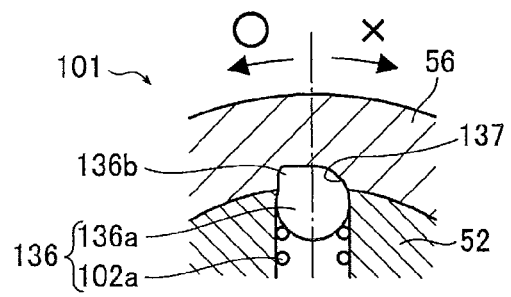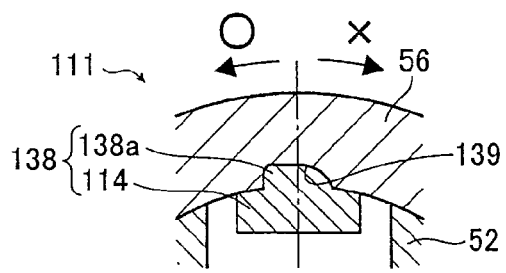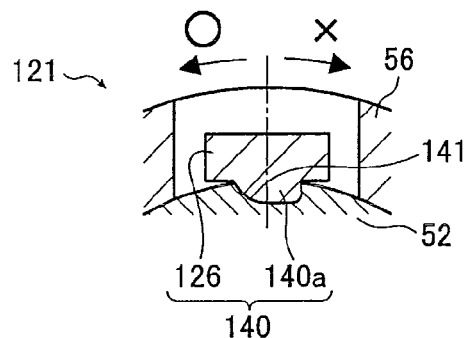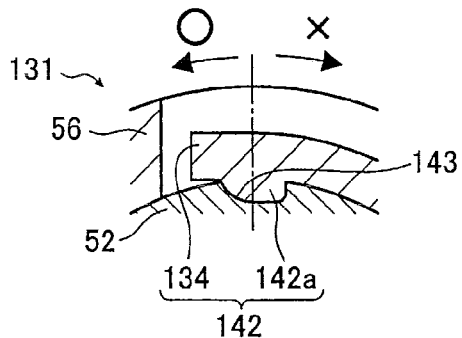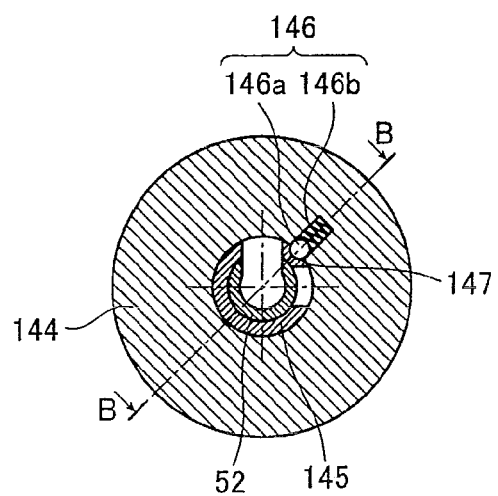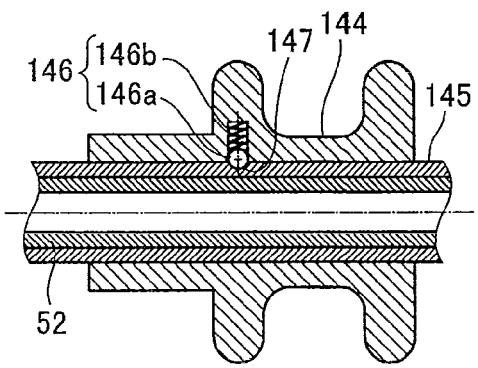

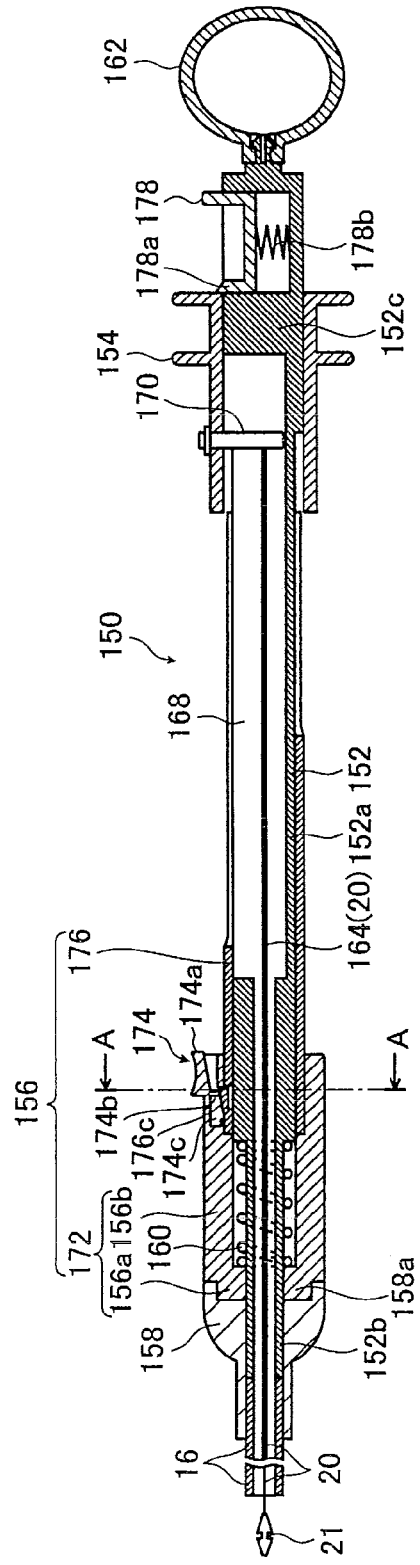
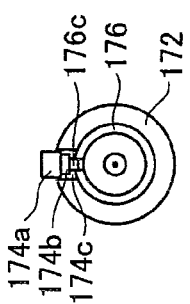
FIG.21A
FIG.21B

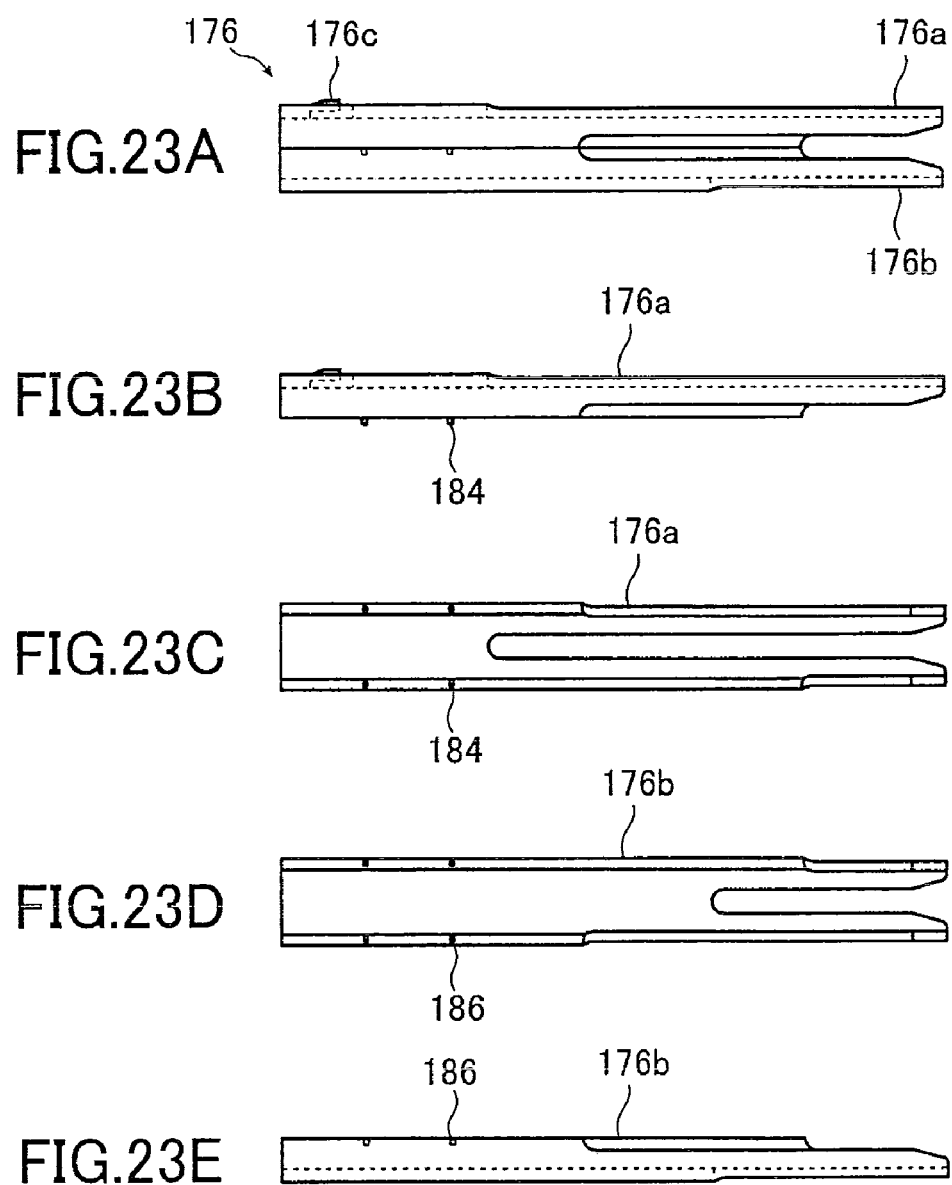

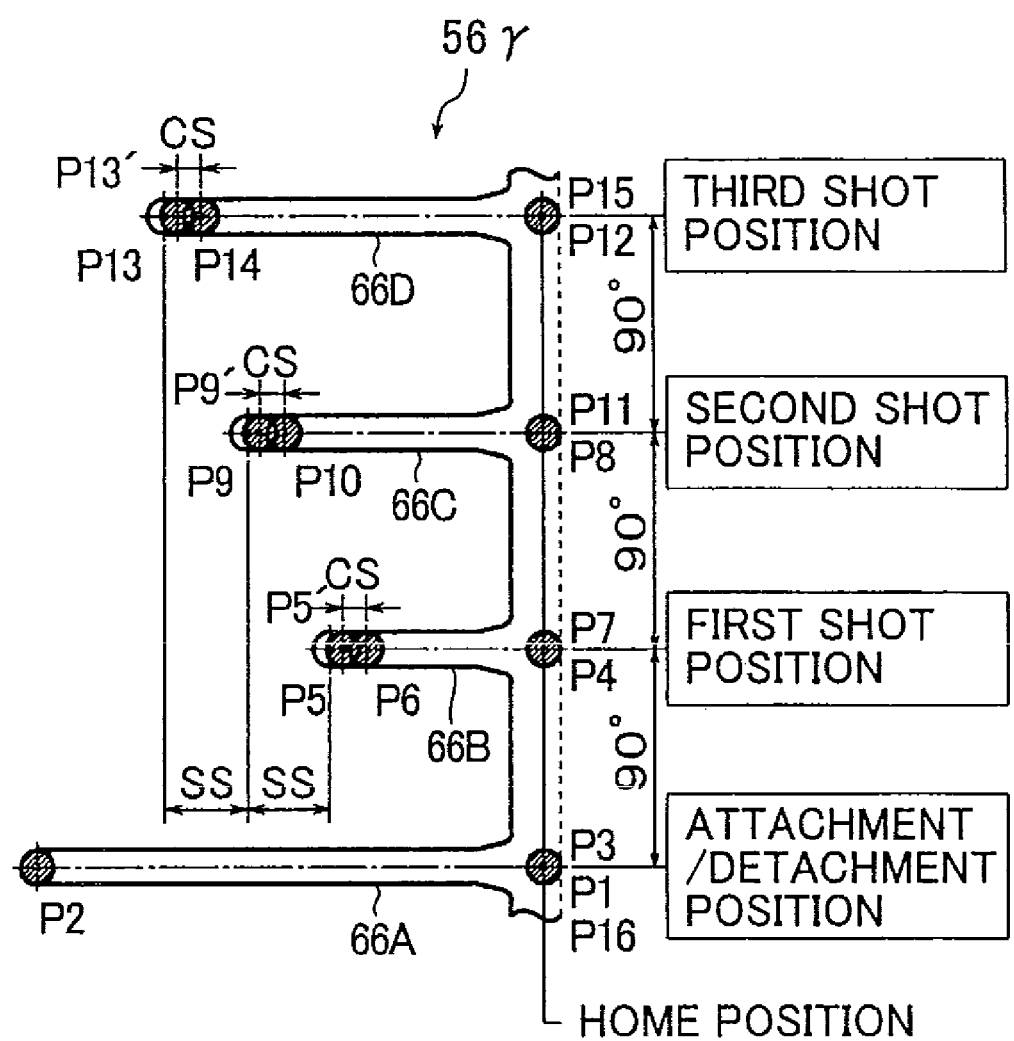

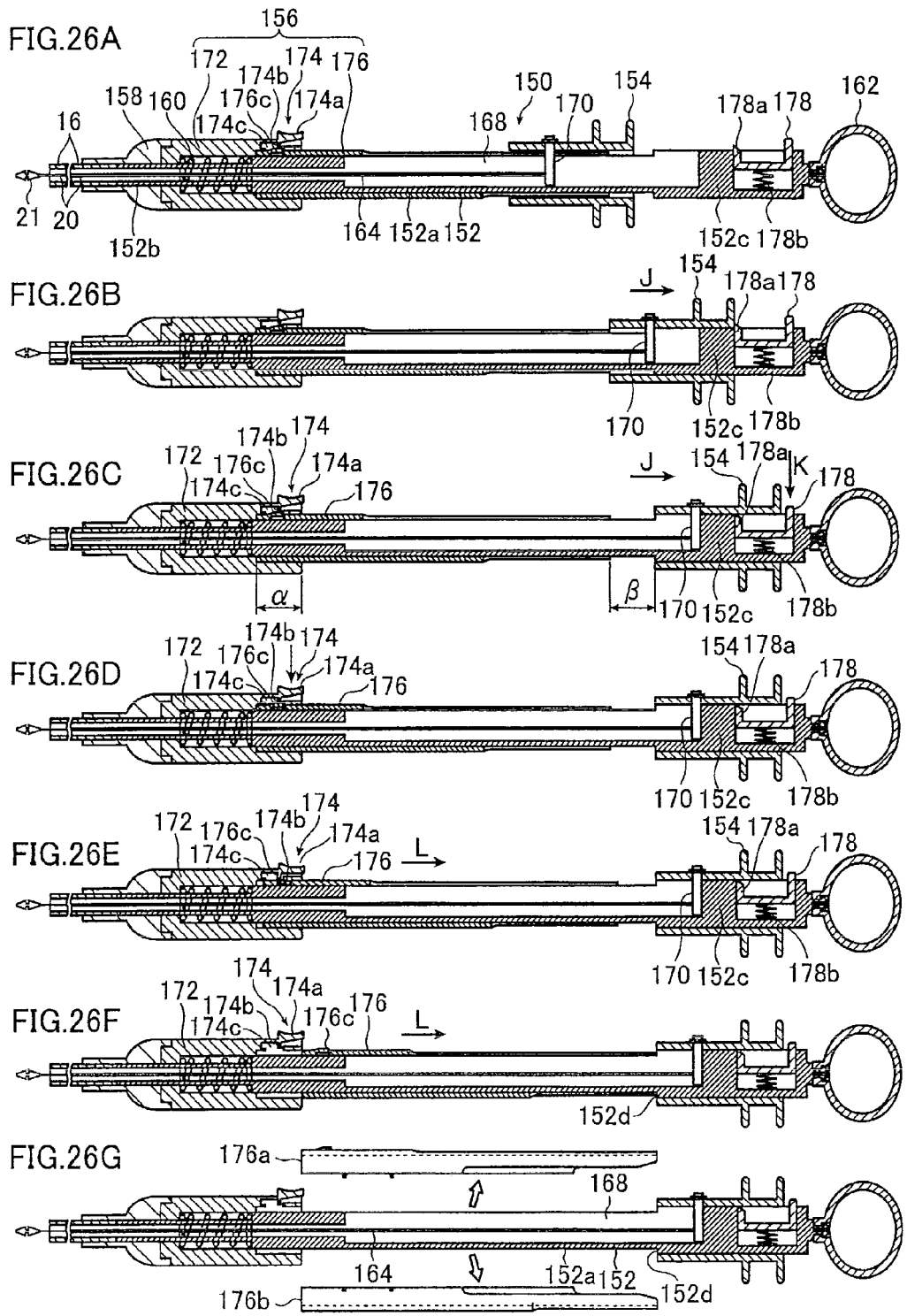

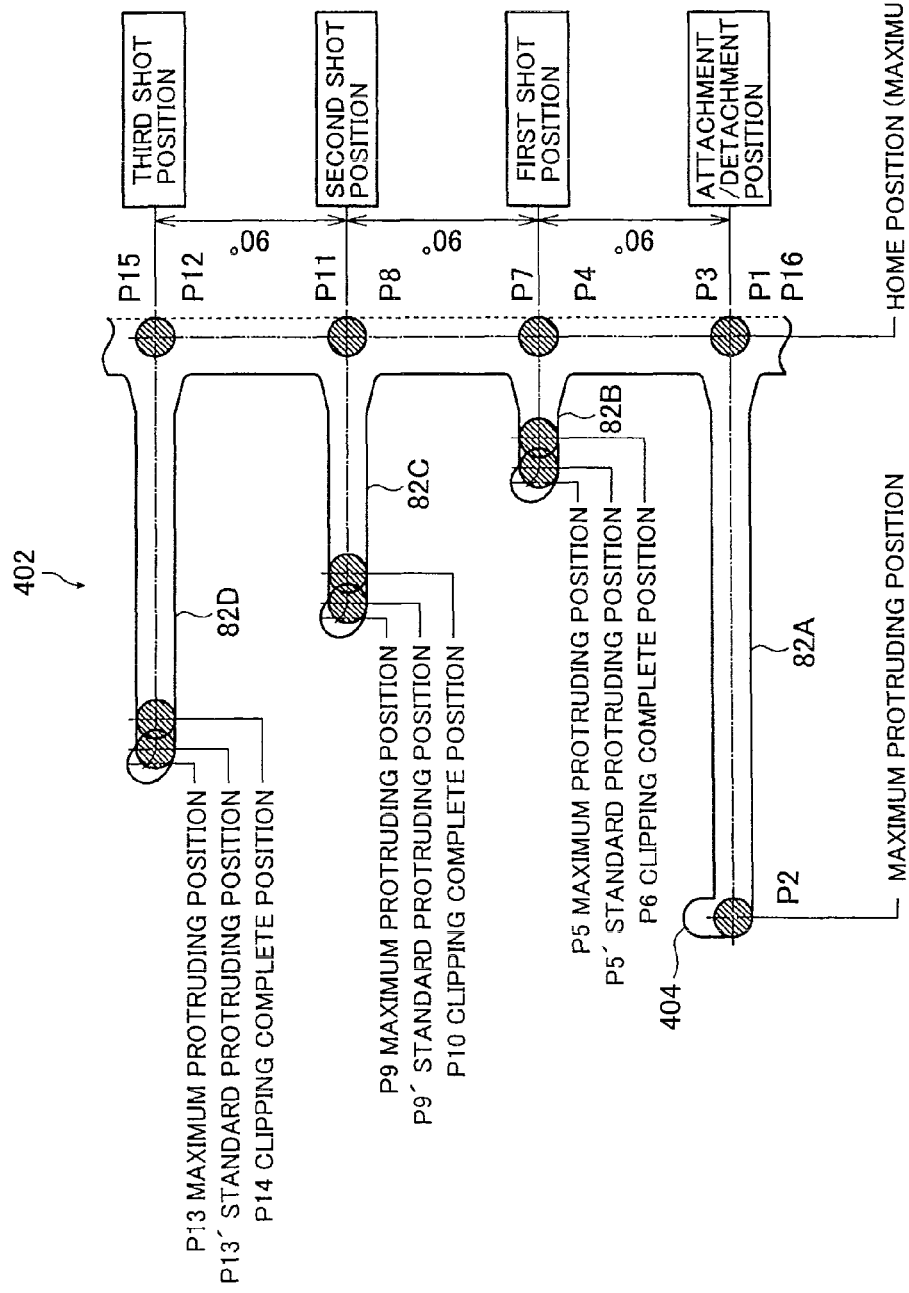

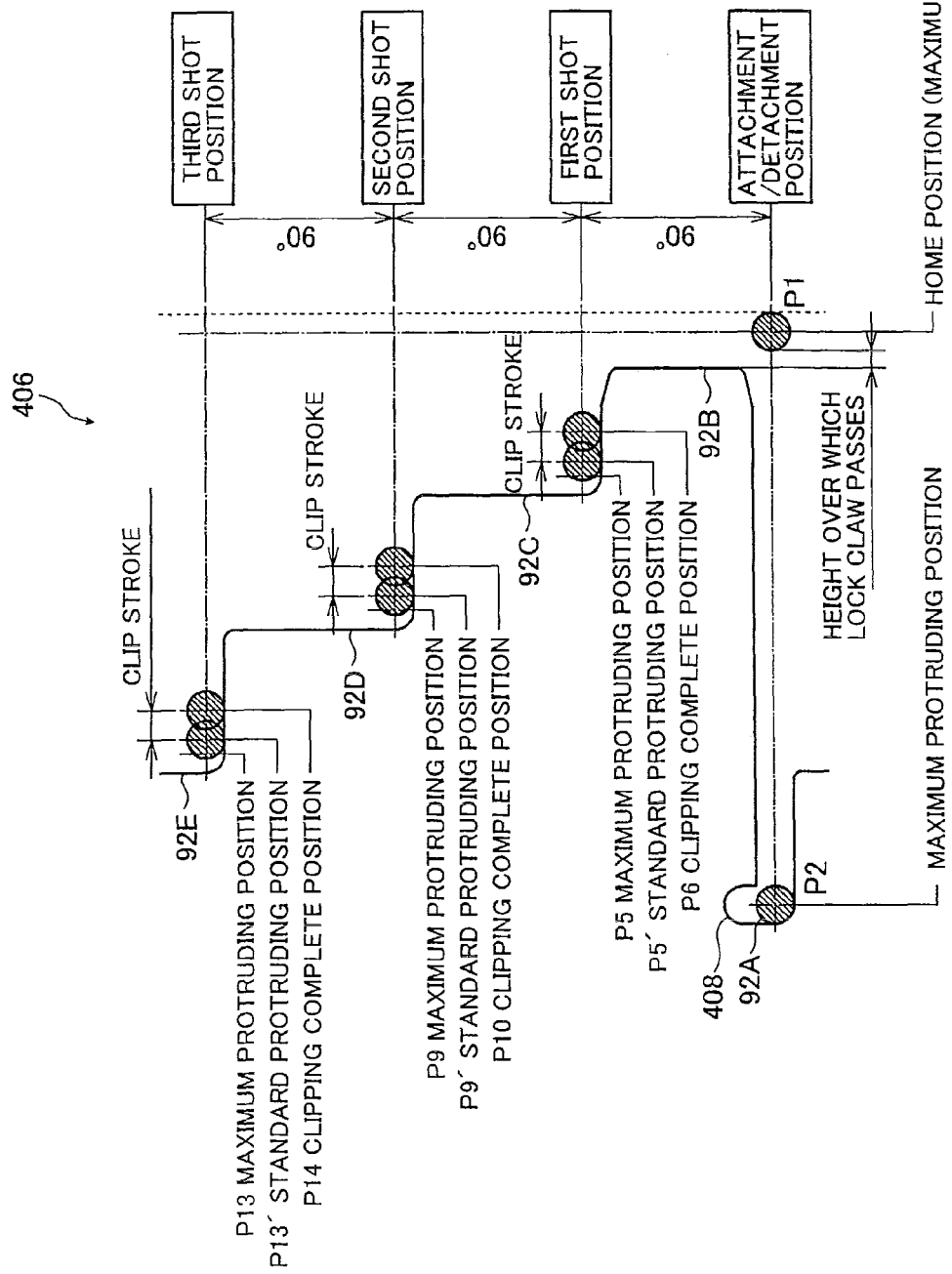

MANIPULATING HANDLE FOR SUCCESSIVE CLIPPING DEVICE, SUCCESSIVE CLIPPING DEVICE, MANIPULATING HANDLE FOR CLIPPING DEVICE, AND CLIPPING DEVICE

BACKGROUND OF THE INVENTION

The present invention relates to a technical field of an endoscopic clipping device used for stopping bleeding, suturing or closing a wound, or the like in a living body or the like. More particularly, the present invention relates to a manipulating handle for a successive clipping device which allows a plurality of clips to be used in succession, and a successive clipping device using such a manipulating handle as well as a manipulating handle for a clipping device using a single clip, and a clipping device using such a manipulating handle.

Recently, an endoscopic clipping device is used for causing a clip to protrude from the forward end of an endocope inserted into a living body to pinch a bleeding portion or a portion to be treated after removal of a lesion tissue with the clip, thereby stopping the bleeding, suturing or closing the wound. In a conventionally used endoscopic clip, a single clip is detachably attached to the forward end of a manipulating wire, and each time clipping is effected, the entire sheath is pulled out of the endoscope, and the sheath is loaded with the next clip before being inserted into the endoscope again for the next clipping. In this way, the conventional clipping device involves a rather bothersome operation.

In view of this, JP 2002-272751 A describes a clipping device for a living tissue in which a plurality of clips is arranged in a single sheath. Specifically, there is described a clipping device for a living tissue which includes an introduction tube insertable into a living body cavity, at least two manipulating wires inserted through the introduction tube to be capable of advancing and retreating therein, and at least two clips each having a proximal end portion, and arm portions which extend from the proximal end portion and have pinching portions formed at the forward ends thereof. In the clipping device for a living tissue, the plurality of clips is arranged in series in the introduction tube, and the clips and the manipulating wires are engaged with each other.

Further, JP 2002-272751 A also describes a mechanism as a manipulating portion of the clipping device, which effects clipping by connecting the individual manipulating wires to the individual clips, providing the manipulating portion with knobs connected to the manipulating wires, and individually manipulating the knobs. The knobs are each engaged with a slider provided in the manipulating portion. Further, the slider has a ratchet mechanism which allows the slider to be axially movable with respect to the proximal portion.

By arranging a plurality of clips within a single introduction tube (hereinafter referred to as sheath) as in the clipping device (hereinafter referred to also as clipping device) for a living tissue described in JP 2002-272751 A, it is possible to effect clipping (i.e., clipping manipulation) of a plurality of portions without pulling the entire sheath out of the endoscope.

However, in the clipping device described in JP 2002-272751 A, the wires are attached to the grips on a one-by-one basis to result in an increase in the number of components, which leads to the problem of higher cost of the device, and the problem of a large number of production steps.

In addition, because the amount of sliding of the slider is not restricted, a manipulator (operator) needs to perform an operation of protruding the clip from the forward end of the sheath, while checking the amount of sliding. When the amount of sliding of the slider increases to cause even the forward end of the next clip to protrude, the manipulation of the clip becomes difficult.

Moreover, the knobs are provided correspondingly to the individual clips, and hence the order of manipulations may be mistaken and, when an unintended clip is pulled, the clip or the sheath may be broken.

Thus, due to the complexity of slider manipulation and such manipulation as pulling of the wires with the knobs, the problems of poor manipulating properties, and a high risk of faulty manipulation also arise.

On the other hand, JP 2002-191609 A describes an example of a clipping device capable of being attached, and effecting ligating manipulation only by advancing and retreating a manipulating member. The clipping device has a clip, a presser tube as a clamping ring fitted over the clip to close it, a connection member insertable into the presser tube to be engaged with the clip, a sheath portion capable of accommodating therein the clip and the presser tube, a manipulating wire inserted through the sheath portion to be capable of advancing and retreating therein, and a hook portion provided in at least one of the presser tube and the sheath portion so as to engage the sheath portion with the presser tube when the clip and the presser tube protrude forward of the sheath portion, and inhibit the presser tube from being accommodated again in the sheath portion.

As described in JP 2002-191609 A, by axially inserting and engaging the hook formed at the forward end of the manipulating wire with respect to the connecting member on the proximal-end side of the clip, the clip can be attached to the manipulating wire by merely moving the manipulating wire in a front-rear direction.

However, when the connecting member of the clip and the connected member provided at the forward end of the manipulating wire are attached in a direction orthogonal to the center axes of the sheath and the clip, if the amount of protrusion of the manipulating wire from the forward end of the sheath changes, the problem of difficult attachment of the connecting member and the connected member arises.

As a result, in the case with the manipulating handle described in JP 2002-191609 A, if a slider moves at the attachment of the clip to the manipulating wire, the amount of protrusion of the manipulating wire from the forward end of the sheath changes, i.e., the position of the connecting member at the forward end of the manipulating wire changes. Consequently, the attachment of the clip to the manipulating wire may be difficult, and the shifted position may cause the deformation of the manipulating wire.

SUMMARY OF THE INVENTION

It is therefore an object of the present invention to solve the above-mentioned problems associated with the prior art technologies, and provide a manipulating handle for a successive clipping device which is high in manipulating properties, producible at low cost, and capable of effecting clipping of a plurality of portions without pulling the entire sheath out of an endoscope, and a successive clipping device using such a manipulating handle.

It is another object of the present invention to provide a manipulating handle for a clipping device which allows reliable and easy attachment of clips to a manipulating wire, and a clipping device using such a manipulating handle.

A manipulating handle for a successive clipping device according to the present invention comprises: a sheath; a manipulating wire, which is arranged in an interior of the sheath, and has a forward end to which a plurality of clips are connected; a cylindrical handle main body connected to the sheath, with the manipulating wire extending from the sheath being arranged in an interior thereof; a slider, which is attached onto an outer circumferential surface of the handle main body to be movable in an axial direction thereof, and engaged with the manipulating wire, for moving the manipulating wire in the axial direction of the handle main body; and a slider-movement-amount regulating member attached onto the outer circumferential surface of the handle main body so as to be rotatable in a circumferential direction of the handle main body, for regulating, according to a rotational position in a circumferential direction thereof, an amount of movement of the slider in the axial direction of the handle main body to one of a plurality of different amounts of movement required for respective clipping manipulations using the plurality of clips connected to the manipulating wire, wherein the slider is moved in the axial direction of the handle main body so as to move the manipulating wire arranged in the interior of the sheath in an extending direction of the sheath, to thereby move the plurality of clips connected to the manipulating wire.

A successive clipping device according to the present invention comprises: such a manipulating handle for the successive clipping device; a plurality of clips loaded in an interior of a forward end of the sheath each in a state of being engaged with another of the clips arranged in a front-rear direction; and a connecting member connected to the rearmost one of the plurality of clips, wherein a forward end of the manipulating wire is detachably connected to the connecting member in the sheath.

A manipulating handle for a clipping device according to the present invention comprises: a sheath; a manipulating wire, which is arranged in an interior of the sheath, and has a forward end to which at least one clip is connected; a cylindrical handle main body connected to the sheath, with the manipulating wire extending from the sheath being arranged in an interior thereof; a slider, which is attached onto an outer circumferential surface of the handle main body so as to be movable in an axial direction thereof, and engaged with the manipulating wire, for moving the manipulating wire in the axial direction of the handle main body; and a wire position fixing mechanism for temporarily fixing the manipulating wire with respect to the sheath in a state in which a forward end of the manipulating wire is protruding from the forward end of the sheath by a given length, wherein the slider is moved in the axial direction of the handle main body so as to move the manipulating wire arranged in the interior of the sheath in an extending direction of the sheath so that the at least one clip connected to the manipulating wire is moved.

A clipping device according to the present invention comprises: such a manipulating handle for the clipping device; a clip loaded in the interior of the forward end of the sheath; and a connecting member connected to the clip, wherein a forward end of the manipulating wire is detachably connected to the connecting member in the sheath.

BRIEF DESCRIPTION OF THE DRAWINGS

FIG. 13 is a cross-sectional view illustrating a position regulating mechanism used in Embodiment 4;

FIGS. 14A and 14B are a lateral cross-sectional view and a partial vertical cross-sectional view, respectively, each illustrating a position regulating mechanism used in a modification of Embodiment 4;

FIGS. 15A and 15B are a lateral cross-sectional view and a partial vertical cross-sectional view, respectively, each illustrating a position regulating mechanism used in another modification of Embodiment 4;

FIGS. 16A and 16B are a lateral cross-sectional view and a partial vertical cross-sectional view, respectively, each illustrating a position regulating mechanism used in still another modification of Embodiment 4;

FIGS. 17A to 17D are partial cross-sectional views illustrating the positional regulating mechanisms used in the respective modifications of Embodiment 4;

FIGS. 18A and 18B are a lateral cross-sectional view and a partial vertical cross-sectional view, respectively, each illustrating the relationship between a slider and a slider guide in Embodiment 5;

FIG. 21A is a cross-sectional view illustrating the manipulating handle of Embodiment 6;

FIG. 21B is a cross-sectional view along the line A-A of FIG. 21A;

FIG. 23A is a front view illustrating a slider guide attachment/detachment portion in Embodiment 6;

FIGS. 23B and 23C are a front view and a bottom view, respectively, each illustrating one split piece of the slider guide attachment/detachment portion;

FIGS. 23D and 23E are a plan view and a front view, respectively, each illustrating the other split piece of the slider guide attachment/detachment portion;

FIGS. 25A to 25C are partial developed views of the slider guide during an operation of clipping manipulation, which correspond to FIGS. 24A to 24C, respectively;

FIGS. 26A to 26G are cross-sectional views progressively illustrating the states of the manipulating handle during the replacement of the slider guide attachment/detachment portion in Embodiment 6;

FIG. 39 is a partial developed view of the outer circumferential surface of a slider guide used in Embodiment 9; and FIG. 40 is a partial developed view of the outer circumferential surface of a slider guide used in a modification of Embodiment 9.

DETAILED DESCRIPTION OF THE INVENTION

A manipulating handle for a successive clipping device, and a successive clipping device using such manipulating handle as well as a manipulating handle for a clipping device, and a clipping device using such a manipulating handle each according to the present invention are described in detail based on the embodiments thereof illustrated in the accompanying drawings.

Embodiment 1

Figure 1:
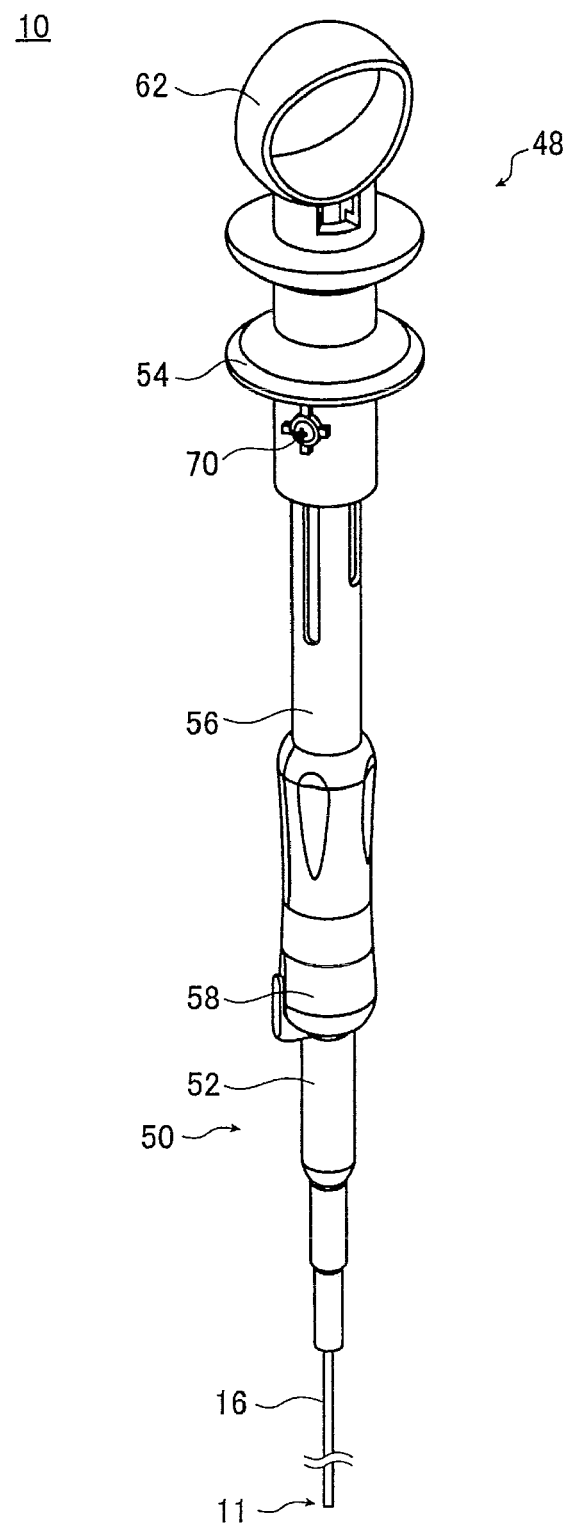
FIG. 1 is a perspective view illustrating a schematic configuration of a successive clipping device using a manipulating handle according to Embodiment 1 of the present invention.

FIG. 1 illustrates a schematic configuration of a successive clipping device (hereinafter also referred to simply as "clipping device") 10 using a manipulating handle according to Embodiment 1 of the present invention. The clipping device 10 includes a manipulation operating portion 11 and a manipulating portion 50.

Figure 2A:
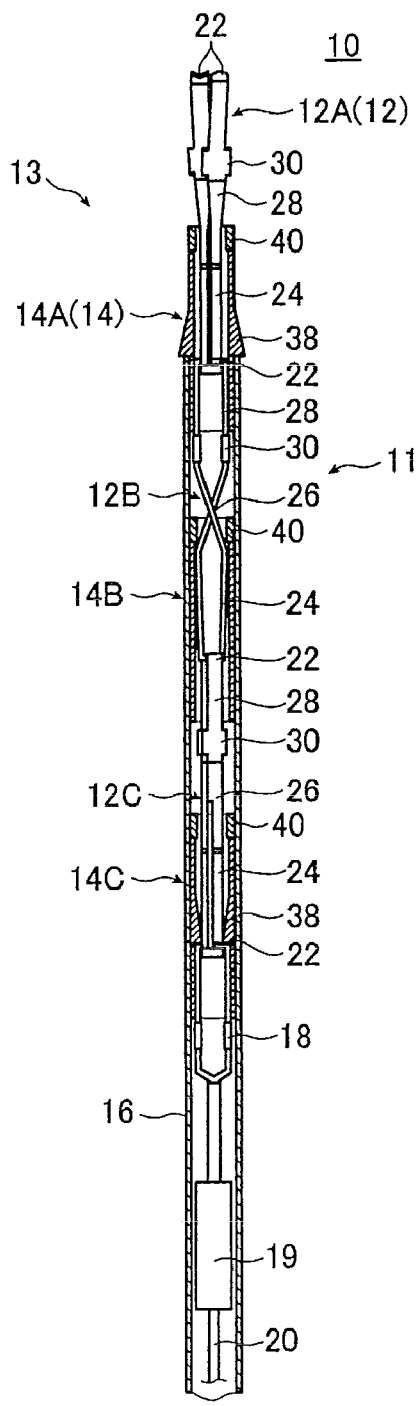
FIGS. 2A and 2B are enlarged cross-sectional views each illustrating a forward end portion of the clipping device illustrated in FIG. 1.
Figure 2B:
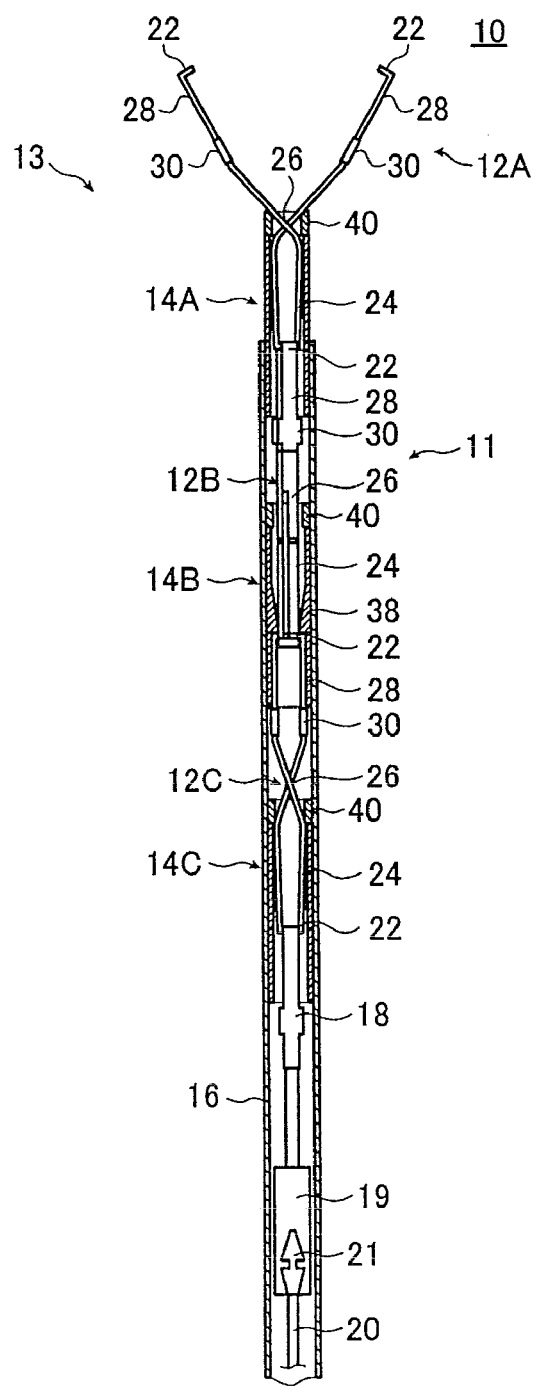

FIG. 2A is a cross-sectional view illustrating a schematic configuration of the manipulation operating portion 11 of the successive clipping device 10. FIG. 2B is a cross-sectional view of the manipulation operating portion 11 when viewed at an angle 90-degree different from the viewing angle of FIG. 2A.

In the following description, a lower end portion (on the side with the manipulation operating portion 11) in FIG. 1, and an upper end portion in each of FIGS. 2A and 2B are each called a "forward end", and a lower end portion in each of FIGS. 2A and 2B, and an upper end portion (on the side with the manipulating portion 50) of FIG. 1 are each called a "proximal end".

As illustrated in FIGS. 2A and 2B, the manipulation operating portion 11 of the clipping device 10 includes a plurality of clips 12 (12A, 12B, and 12C), connection rings 14 (14A, 14B, and 14C) that cover the engagement portions of the adjacent clips 12 to maintain the connection states of the clips 12, a sheath 16 into which the clips 12 and the connection rings 14 are fitted, a dummy clip 18 connected to the rearmost third clip 12C, and a manipulating wire 20 connected to the dummy clip via a connecting member 19. The sheath 16 and the manipulating wire 20 (including a connected member (hook) 21 at the forward end thereof) of the manipulation operating portion 11, and the manipulating portion 50 constitute a manipulating handle 48 of the present invention. The plurality of clips 12 (12A, 12B, and 12C), the connection rings 14 (14A, 14B, and 14C), the rearmost dummy clip 18, and the connecting member 19 of the manipulation operating portion 11 constitute a clip series (connected clip unit) 13. The dummy click 18 is a member for connecting the manipulating wire 20 and the plurality of clips 12 via the connecting member 19.

Thus, as illustrated in FIGS. 1, 2A, and 2B, the clipping device 10 of the present invention includes the clip series 13 and the manipulating handle 48 of the present invention.

FIGS. 2A and 2B illustrate an initial state (standby state) immediately before an operation of clipping manipulation using the foremost clip 12A is started.

One of the clips 12 and the corresponding one of the connection rings 14 including a clamping ring 40 described later constitute an endoscopic bleeding stop clip member. The manipulation operating portion 11 of the clipping device includes a plurality of such bleeding stop clip members loaded inside the forward end of the elongated sheath 16.

The terminal end of the consecutive bleeding stop clip members are engagedly connected to the dummy clip 18 as a member for connecting the clip series 13 and the manipulating wire 20. The dummy clip 18 is connected to the manipulating wire 20 via the connecting member 19. The manipulating wire 20 extends to the proximal end portion of the sheath 16, and connected to the manipulating portion 50 (see FIG. 1) described later.

By pulling the manipulating wire 20 from the manipulating portion 50 by a predetermined pulling length, and moving the dummy clip 18 in one direction by a predetermined distance, a series of the clips 12 move by equal amounts, and the foremost clip 12 is clamped by the clamping ring 40 at the forward end of the connection ring 14 retaining the foremost clip 12 to effect clipping manipulation (clipping) for stopping bleeding, marking, or the like by the foremost clip 12. After the clipping manipulation using the foremost clip 12 is completed, by pushing the manipulating wire 20 toward the forward end of the sheath 16 by a predetermined length, the next clip 12 is brought into a usable state (standby state) to allow clipping manipulation to be performed in succession.

FIGS. 2A and 2B are views of a state in which the foremost first clip 12A has protruded from the forward end of the sheath 16, but when the clips 12 and the like are loaded in the sheath 16, they are set with the foremost first clip 12A being completely contained in the sheath 16. Although FIGS. 2A and 2B illustrate the three clips 12, and a triple-shot clipping device, the number of the clips 12 may be any as long as it is not less than 2.

Figure 3:
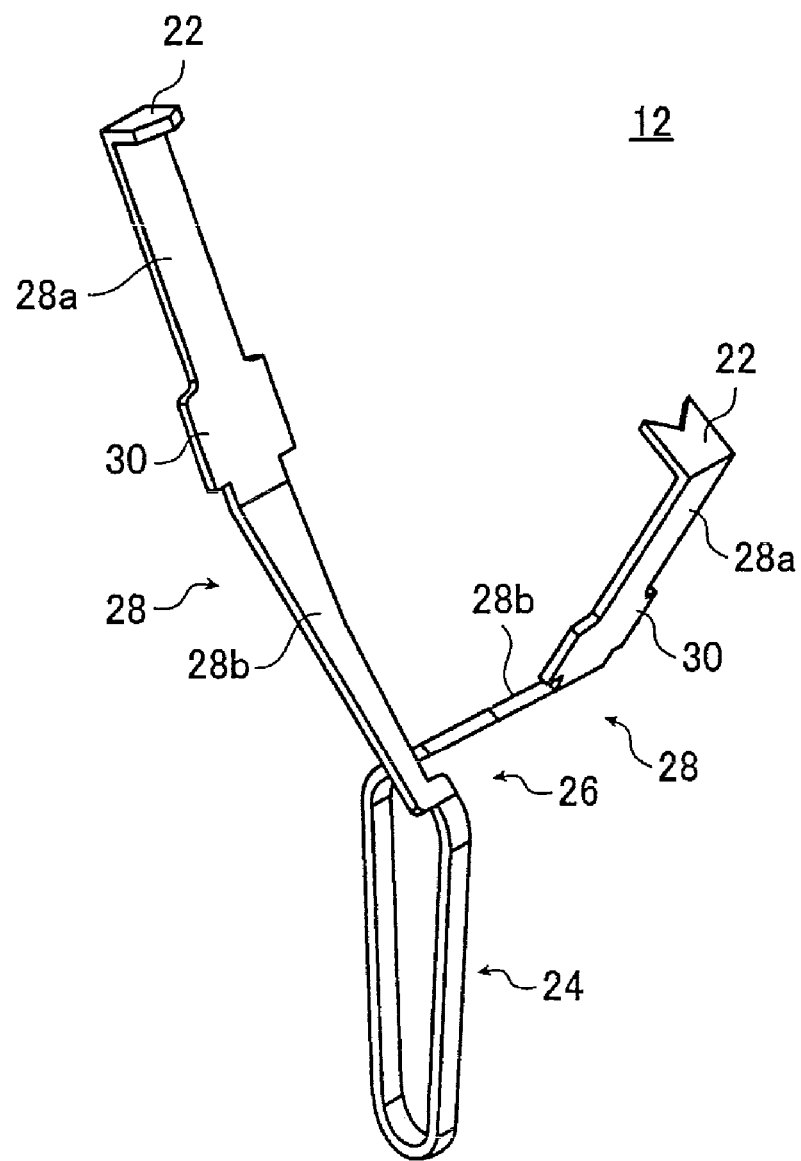
FIG. 3 is a perspective view illustrating a clip.

FIG. 3 is a perspective view illustrating a schematic configuration of each of the clips 12. The clip 12 is a closed clip including a turned portion 24 which is 180-degree turned with respect to claw portions 22. That is, the clip 12 has a shape obtained by bending a single elongated plate by 180 degrees to form a closed end, crossing the both ends thereof, and bending the end portions into opposing relation to form the claw portions 22 at two open ends. On the open-end side of the resulting crossing portion 26, there are arm portions 28, while there is the turned portion 24 on the closed-end side thereof. In the respective center portions of the arm portions 28, partially widened projections 30 are formed. Each of the arm portions 28 is divided by the projection 30 into a distal portion 28a closer to the claw portion 22, and a proximal portion 28b closer to the crossing portion 26. For the clips 12, a metal with biocompatibility is preferably used. For example, it is possible to use SUS 630 or SUS 631, which is a precipitation-hardening stainless steel.

The clamping ring 40 fixed to the forward end portion of the connection ring 14 fitted over the crossing portion 26 of the clip 12 moves by a predetermined amount toward the claw portions 22 (toward the projections 30), while pressing the proximal portions 28b of the arm portions 28, whereby the arm portions 28 and the claw portions 22 are closed, with the claw portions 22 exerting a predetermined fit-engagement force (gripping force).

To reliably pinch a target portion such as a bleeding portion or a portion to be subjected to manipulation after the removal of a lesion tissue, the claw portions 22 are formed into a V-shaped male type and a female type.

The widths of the distal portions 28a of the arm portions 28 of the clips 12 remain constant and invariable from the claw portions 22 to the projections 30, while the widths of the proximal portions 28b thereof gradually increase from the crossing portion 26 toward the projections 30 to be constant in the vicinities of the projections 30. This facilitates and ensures the movement of the clamping ring 40 as well as the opening, closing, and fit-engagement of the claw portions 22, thereby facilitating and ensuring the stopping of bleeding, the suture or closing of a wound, and the like in a living body or the like.

The projections 30 have widths larger than the respective inner diameters of a forward-end-side opening (see a hole 41 of the clamping ring 40 in FIG. 4B, which is described later) of the connection ring 14 and a proximal-end-side opening (a hole 43 in a retaining portion 42 described later) thereof, i.e., larger then the widths of portions which come in contact with the projections 30. As a result, the portions of the clip 12 other than the projections 30 can enter the interior of the connection ring 14, but the projections 30 cannot enter the interior either from the forward-end side or proximal-end side of the connection ring 14.

As illustrated in FIGS. 2A and 2B, the claw portions 22 of the second clip 12B are engaged with the turned portion 24 of the first clip 12A, and retained in a closed state by the connection ring 14A, whereby the first clip 12A and the second clip 12B are brought into a connection state. As illustrated in FIG. 2A, the claw portions 22 of the second clip 12B orthogonally mesh with the turned portion 24 of the first clip 12A to be connected thereto, and hence the first clip 12A and the second clip 12B are connected in 90-degree different orientations. Likewise, the second clip 12B and the third clip 12C are also connected in 90-degree different orientations. That is, the first clip 12A and the third clip 12C are arranged in the same orientation.

Figure 4A:
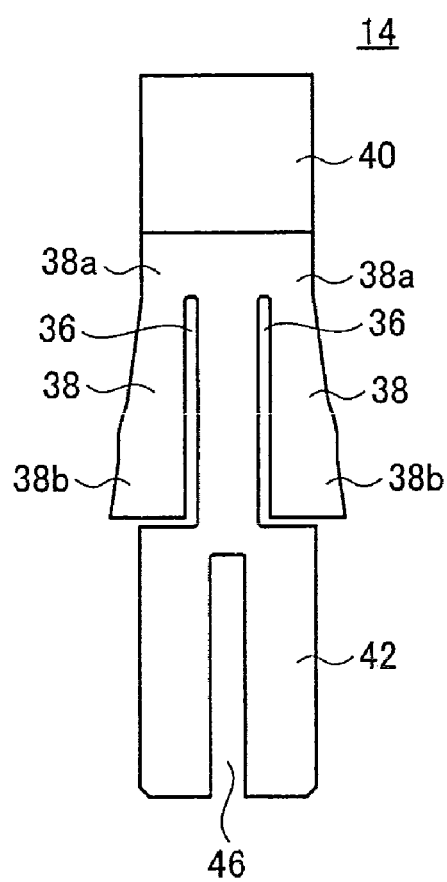
FIGS. 4A to 4C are a front view, a cross-sectional view, and a bottom view, respectively, each illustrating a connection ring.
Figure 4B:
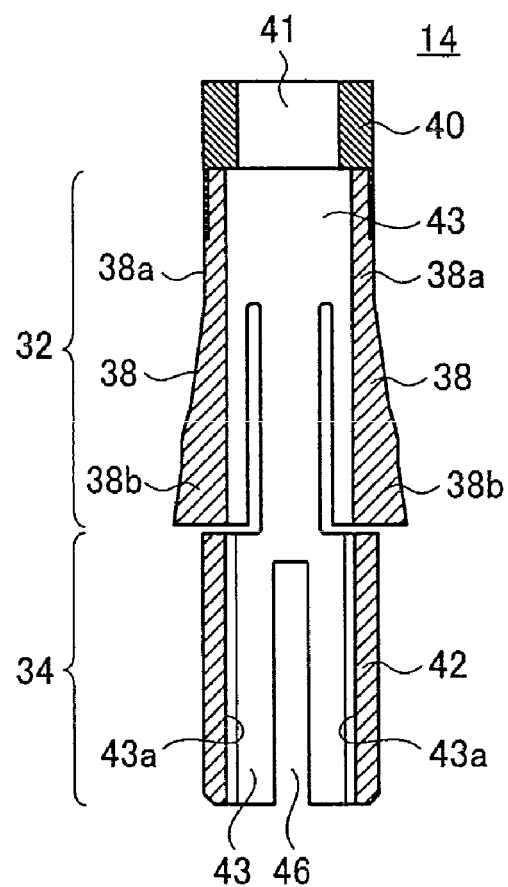
Figure 4C:
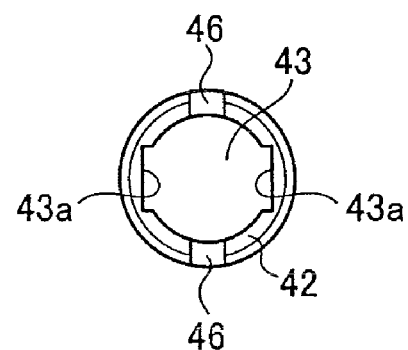

Each of the connection rings 14 is fitted into the sheath 16 so as to be capable of advancing and retreating, while covering the engagement portion between the two preceding and subsequent clips 12, and maintaining a connection state therebetween. That is, the outer diameter of the connection ring 14 is slightly smaller than the inner diameter of the sheath 16 to allow the connection ring 14 to smoothly advance and retreat in the sheath 16 with the movement of the clips 12. FIGS. 4A to 4C illustrate a schematic configuration of an embodiment of the connection ring, of which FIG. 4A is a front view of the connection ring 14, FIG. 4B is a cross-sectional view thereof, and FIG. 4C is a bottom view thereof.

As illustrated in FIGS. 4A to 4C, each of the connection rings 14 includes the clamping ring 40, and the retaining portion 42. The connection ring 14 has the clamping ring 40 made of metal, and fastened to the forward end of the retaining portion 42 made of resin to integrally include the two members. The retaining portion 42 made of resin serves to maintain the connection state, and retain the clip 12 in the connection ring 14, while the clamping ring 40 made of metal serves to clamp the clip 12. The connection ring 14 may be formed of a single member as long as it can perform the respective functions of both the clamping ring 40 and the retaining portion 42.

The clamping ring 40 is a cylindrical (ring-shaped) metal component mounted on the forward end of the connection ring 14, and has the hole 41 whose inner diameter is larger than the width of the clip 12 in the vicinity of the crossing portion 26, and smaller than the width of each of the projections 30. As a result, the clamping ring 40 can move in the vicinity of the crossing portion 26 of the clip 12 retained thereby, but cannot go beyond the projections 30 toward the forward end of the clip 12. That is, the projections 30 function as a stopper which determines the movement limit of the connection ring 14 advancing with respect to the clip 12.

The clamping ring 40 is set at a predetermined position in the vicinity of the crossing portion 26 of the clip 12. The clamping ring 40 moves from the initial position thereof, i.e., from the crossing portion 26 toward the projections 30, with the arm portions 28 of the clip 12 increasing in width, so as to perform a clamping function of closing both the diverged arm portions 28 of the clip 12, and fixing them. For the clamping ring 40, a metal with biocompatibility is used. For example, a stainless steel SUS 303 or SUS 304, a titanium alloy, or the like can be used. By forming the clamping portion 40 of metal, a frictional force serving as a claming force can be exerted on the metal clip 12.

The retaining portion 42 is a substantially cylindrical (ring-shaped) component formed by resin molding. The retaining portion 42 has a first region 32 retaining the preceding clip 12, and a second region 34 which is a connection retaining region for retaining the subsequent clip 12 in a state connected to the preceding clip. The retaining portion 42 has the hole 43 connecting to the hole 41 of the clamping ring 40, and extending through the first region 32 and the second region 34.

The first region 32 is provided with the circular hole 43 capable of accommodating the turned portion 24 of the clip 12, and the proximal portions 28b of the arm portions 28 thereof, and larger than the hole 41 of the clamping ring 40. The outer surface of the forward end portion of the first region 32 is provided with a stepped portion for allowing the clamping ring 40 to be fitted. The clamping ring 40 and the retaining portion 42 are fit-engaged by such close fit as to prevent disengagement therebetween in a state in which they are loaded in the sheath 16 and during clipping manipulation.

The first region 32 has a skirt portion 38 which inclinedly diverges into a skirt-like configuration with respect to the axis of the main body of the connection ring 14.

In the skirt portion 38, the forward-end side, i.e., an upper base portion 38a in FIGS. 4A and 4B is connected to a main body 42a of the retaining portion 42, and a lower diverging portion 38b is partially disconnected from the main body 42a by a cut 36 formed in the main body 42a to be radially diverged or closed. The skirt portion 38 includes two skirt portions formed at two locations on both sides which are apart from each other by 180 degrees and at the same position in the pulling direction of the clips 12, i.e., in the vertical direction of FIGS. 4A and 4B.

As illustrated in FIG. 4A, in a natural state in which no external force is imparted thereto, both the skirt portions 38 are diverged into a skirt-like configuration. At this time, the interior of the first region 32 of the retaining portion 42 forms a columnar space, as illustrated in FIG. 4B. On the other hand, when the connection ring 14 is loaded into the sheath 16, as in the case with, e.g., the second connection ring 14B illustrated in FIG. 2B, the skirt portions 38 (diverging portions 38b thereof) are inwardly pushed to enter the internal space, and the inner-circumferential-side portions of the skirt portions 38 (diverging portions 38b thereof) press the side surface (edge portion) of the turned portion 24 of the second clip 12B retained by the first region 32 to retain and keep the second clip 12B from moving in a rotating direction and an advancing/retreating direction within the connection ring 14B. The skirt portions 38 may press and retain the clip retained by the second region 34, i.e., the rear-side clip.

As in the case with the first connection ring 14A illustrated in FIG. 2A, on coming out from the forward end of the sheath 16, the skirt portions 38 are simultaneously opened due to their own elasticity, thus releasing the first clip 12A from retention, and becoming wider than the inner diameter of the sheath 16 to prevent the connection ring 14A from retreating into the sheath 16. In this state, the manipulating wire 20 is pulled, and the first clip 12A retreats, whereby the connection ring 14A advances relatively to the first clip 12A to clamp the first clip 12A with the clamping ring 40 integrally fastened to the connection ring 14A.

Therefore, it is necessary for the skirt portions 38 to have elasticity so as to be capable of being inwardly closed within the sheath 16, and diverged into a skirt-like configuration when they get out of the forward end of the sheath 16 and released from an external force. At the same time, it is also necessary for the skirt portions 38 to have rigidity which enables the clip 12 to be retained within the sheath 16, and rigidity which withstands the repulsive force of the clamping force of the clip 12 at the forward end of the sheath 16.

From those viewpoints, for the retaining portion 42, a material having biocompatibility and providing elasticity and rigidity each required of the skirt portions 38 is used. In addition, the shape thereof is determined so as to provide elasticity and rigidity required of the skirt portions 38. Examples of a material that can be used for the retaining portion 42 include polyphenylsulfone (PPSU), aromatic nylon, and the like. In terms of ease of production, the retaining portion 42 is preferably molded integrally.

The second region 34 is provided on the proximal-end side of the first region 32. The second region 34 retains the next clip 12 engaged with the clip 12 retained by the first region 32, specifically the claw portions 22 and the distal portions 28a of the arm portions 28 in a state in which the claw portions 22 are closed with the closed end (tail portion) of the turned portion 24 of the preceding clip 12 being held therebetween.

The second region 34 has a length which is substantially equal to the movement distance required for the clamping ring 40 set at the initial position with respect to the clip 12 to move till completing the clamping of the clip 12 as a region length. That is, while the clip 12 retreats relatively to the connection ring 14 to be clamped, the second region 34 of the connection ring 14 maintains the connection between the two clips 12 retained therein to allow the pulling force of the rear clip 12 to be transmitted to the forward-end-side clip 12 and, when the clamping by the clamping ring 40 is completed, the engagement portion of the two clips 12 exits the second region 34, thereby disconnecting the clips 12.

As illustrated in FIGS. 4B and 4C, the second region 34 is provided with the hole 43 having the same inner diameter as in the first region 32, and extending therethrough from the first region 32. The second region 34 further has two grooves (recesses) 43a formed in the two opposing portions thereof. The second region 34 also has two slits 46 that are cut from the proximal end thereof.

The grooves 43a can accommodate therein the distal portions 28a of the arm portions 28 of the clip 12 retained by the second region 34, with the claw portions 22 being closed.

The grooves 43a are provided at two positions on both sides in the direction in which the claw portions 22 of the clip 12 retained by the second region 34 are opened and closed (lateral direction in FIG. 4B). Plate surfaces of the distal portions 28a of the arm portions 28 of the clip 12 retained by the second region 34 come in contact with inner walls of the grooves 43a. The width (opening width) of each of the grooves 43a is slightly larger than the maximum width of the distal portion 28a of each of the arm portions 28 of the clip 12. The distance from the wall surface of one of the grooves 43a to the wall surface of the other groove 43a is substantially equal to the sum total of the lengths (lengths in the diverging direction) of the two claw portions 22 of the clip 12. The width of the groove 43a is smaller than the width of each of the projections 30 formed in the arm portions 28. Therefore, the projections 30 of the clip 12 retained by the second region 34 cannot enter the grooves 43a.

The arrangement can prevent the subsequent clip 12 (e.g., 12C) from overlapping the preceding clip 12 (e.g., 12B) from behind. As a result, it is possible to (1) maintain the relative positions of the anterior and posterior (preceding and subsequent) clips 12, and (2) maintain a manipulation of pushing out the clip 12 by the manipulating wire 20 (see slider 54 in FIG. 5).

(1) When the overlapping of the subsequent clip 12 from behind occurs, a manipulation stroke of the manipulating wire 20 changes disadvantageously. However, it is possible to prevent such overlapping and maintain the relative positions of the preceding and subsequent steps 12, and hence the manipulation stroke can be maintained.

In addition, the bending rigidity of the second region 34 has been reduced by the slit 46 provided in the connection ring 14, and angle suitability has been provided by chain-like connection between the clips 12. When the posterior clip 12 excessively comes into the anterior connection ring 14, flexibility decreases to degrade the angle suitability. However, it is possible to prevent the overlapping from behind and maintain the relative positions of the preceding and subsequent clips 12, and hence the angle suitability can be maintained.

(2) The manipulation of pushing out the clip 12 by the manipulating wire 20 can be maintained.

<Manipulation of Pushing Out Clip 12 by Manipulating Wire 20>

The projections 30 of the dummy clip 18 push the proximal-end side (the end portion of the retaining portion 42) of the connection ring 14C of the third clip 12C.

In the sheath 16, the third clip 12C has been integrated with the connection ring 14C by frictional contact so that the pushing force transmitted to the connection ring 14C is transmitted to the clip 12C (At this time, in the third clip 12C, the diverging portions 38b of the skirt portions 38 of the connection ring 14C are inwardly deformed to retain the turned portion 24 of the third clip 12C).

The projections 30 of the third clip 12C push the proximal-end side (the end portion of the retaining portion 42) of the connection ring 14B of the second clip 12B.

In the sheath 16, the second clip 12B has been integrated with the connection ring 14B by frictional contact so that the pushing force transmitted to the connection ring 14B is transmitted to the clip 12B.

The projections 30 of the second clip 12B push the proximal-end side (the end portion of the retaining portion 42) of the connection ring 14A of the first clip 12A.

In the sheath 16, the first clip 12A has been integrated with the connection ring 14A by frictional contact so that the pushing force transmitted to the connection ring 14A is transmitted to the clip 12A to push it out.

The pulling force of the manipulating wire 20 is directly exerted on the clip 12, and hence it is not particularly affected by the overlapping from behind.

<Transmission of Pulling Manipulation by Manipulating Wire 20 Effected by Clip 12>

The forward end (claw portions 22) of the dummy clip 18 pulled by the manipulating wire 20 pulls the proximal end (turned portion 24) of the third clip 12C.

The forward end (claw portions 22) of the third clip 12C pulls the proximal end (turned portion 24) of the second clip 12B.

The forward end (claw portions 22) of the second clip 12B pulls the proximal end (turned portion 24) of the first clip 12A.

The distance between the respective wall surfaces of the two grooves 43a may be adjusted appropriately to a dimension which does not cancel the engagement between the turned portion 24 of the preceding clip 12 and the claw portions 22 of the next clip 12, and the distance may be set smaller than the sum total of the lengths of the two claw portions 22 and the width of the portion of the turned portion 24 engaged with the claw portions 22.

For example, the claw portions 22 of the clip 12 retained by the second region 34 may be in a slightly overlapping state, or the connection of the clip with the preceding clip 12 may be maintained in a state in which the claw portions 22 have a slight gap therebetween.

The engagement portion between the two clips 12 is retained by the portion of the second region 34 close to the boundary between the second region 34 and the first region 32. Inside the sheath 16, the turned portion 24 of the preceding clip 12 (e.g., the second clip 12B in the connection ring 14B of FIG. 2B) is retained by the closed skirt portions 38 in the first region 32 so that the advancing/retreating movement and the rotating movement of the clip are restrained. The next clip 12 (e.g., the third clip 12C in the connection ring 14B of FIG. 2B) engaged with the preceding clip 12 is retained by the grooves 43a of the second region 34 in a direction 90-degrees different from the direction in which the preceding clip is retained, whereby the rotating movement thereof is restrained. The next clip 12 is also engaged with the preceding clip 12 whose advancing/retreating movement has been restrained, whereby the advancing/retreating movement thereof is restrained. That is, the engagement portion between the preceding and subsequent clips is retained in a state with very little play by the connection ring 14.

The slits 46 are formed at two positions 90-degree shifted from the skirt portions 38 so as to be shallower than the upper end of the second region 34. In other words, the slits 46 are provided at positions 90-degree shifted from the diverging direction of the clips 12 retained by the second region 34.

The provision of the slits 46 can improve the flexibility of the connection ring 14 to allow the clipping device 10 to pass through a curved portion with small curvature. The provision of the slits 46 also allows a bottom edge (proximal end portion) of the connection ring 14 to be partially turned up. Therefore, when the preceding and subsequent clips 12 are connected together prior to the loading of the clips 12 into the sheath 16, easy connection can be made advantageously by turning up the bottom edge of the connection ring 14.

The depths of the slits 46 are restricted to positions within the second region 34 not reaching the skirt portions 38 of the first region 32, thereby preventing a significant reduction in the strength of the connection ring 14. The depths of the slits 46 are also restricted to positions shallower than the position of the rear end of the clip 12 retained by the first region 32, i.e., to positions shallower than the engagement position of the clips 12. As a result, also in the connection clip unit before being loaded into the sheath 16, it is possible to maintain the retention of the clip 12 by the second region 34 of the connection ring 14.

As illustrated in FIGS. 2A and 2B, the claw portions 22 of the second clip 12B are engaged with the turned portion 24 of the first clip 12A, and the resulting engagement portion is retained by the connection ring 14A. The claw portions 22 of the second clip 12B are retained in the closed state by the inner wall of the connection ring 14A (the second region 34 thereof). As a result, the connection state between the first clip 12A and the second clip 12B is maintained. Likewise, the connection state between the second clip 12B and the third clip 12C is maintained by the connection ring 14B, and the connection state between the third clip 12C and the dummy clip 18 is maintained by the connection ring 14C.

The rearmost third clip 12C is engaged with the dummy clip 18, which is not used for clipping manipulation. The dummy clip 18 includes, at the forward end portion thereof, a resilient portion having a shape similar to that of the open-end-side half portion of the clip 12 extending from the crossing portion 26. That is, the resilient portion of the dummy clip 18 has a shape in which the arm portions including the two claw portions are connected at the crossing portion. The dummy clip 18 is engaged with the turned portion of the third clip 12C with the claw portions being closed, and releases the third clip 12C when the claw portions are opened. In the arm portions of the dummy clip 18 in the illustrated example, projections are not provided, but projections may also be provided therein. To the proximal end portion of the dummy clip 18, the connecting member 19 is attached. The connecting member 19 is detachably connected to the hook-shaped connected member (hook) 21 at the forward end of the manipulating wire 20, which is described later.

For example, the sheath 16 is a flexible coil sheath formed of a tightly wound metal wire. The sheath 16 allows the clip 12 to be movably fitted therein on the forward-end side to accommodate therein the manipulating wire 20 connected to the clip 12 via the dummy clip 18 and the connecting member 19. The sheath 16 is connected to the manipulating portion 50 on the proximal-end side. The inner diameter of the sheath 16 is adjusted to a dimension which allows canceling of the engagement between the turned portion 24 of the preceding clip 12 and the claw portions 22 of the next clip 12. That is, the inner diameter of the sheath 16 is larger than the sum total of the lengths of the two claw portions 22 and the width of the portion of the turned portion 24 engaged with the claw portions 22.

The manipulating wire 20 causes the plurality of clips 12 to advance or retreat in a series of clipping manipulations. The manipulating wire 20 is formed of, e.g., a metal wire, accommodated in the sheath 16, and includes the connected member 21 provided at the forward end portion thereof (the end portion on the opposite side of the manipulating portion 50). The forward end portion of the manipulating wire 20 is connected by the connected member 21 to the clip 12 via the connecting member 19 and the dummy clip 18, while the proximal end portion thereof to which the connected member 21 is not attached is connected to the manipulating portion 50. As described above, the proximal end portion of the sheath 16 is also attached, together with the manipulating wire 20, to the manipulating portion 50 described later.

The connected member 21 of the manipulating wire 20 and the connecting member 19 of the dummy clip 18 have shapes which allow one of the members to be fitted into the other member, and prevent disengagement therebetween when the clip 12 and the manipulating wire 20 perform an advancing/retreating operation, i.e., when they move in the sheath 16. Specifically, the connected member 21 of the manipulating wire 20 has a protruding shape (a conical shape having a protrusion on the forward-end side in this embodiment) larger in diameter than the manipulating wire 20, while the connecting member 19 has a shape in which a space substantially equal to or slightly larger than the connected member 21 is formed, and includes an opening having a diameter smaller than that of the space, and larger than that of the manipulating wire 20 is formed on the side of the space closer to the manipulating portion 50. It is to be noted that the space formed in the connecting member 19 has a shape which does not entirely circumferentially cover the side surface (surface facing the inner circumferential surface of the sheath 16) of the connected member 21. The space is opened in one direction or two opposing directions of four circumferential directions.

By thus forming the connected member 21 into a shape to be fitted into the connecting member 19, and fitting the connected member 21 into the space of the connecting member 19, even when the manipulating wire 20 is pulled toward the manipulating portion 50, the surface of the connected member 21 closer to the manipulating portion 50 is supported by the surface of the connecting member 19 provided with the opening. Therefore, it is possible to prevent the connected member 21 from being disengaged from the connecting member 19.

Next, the manipulating handle is described in detail.

Figure 5:
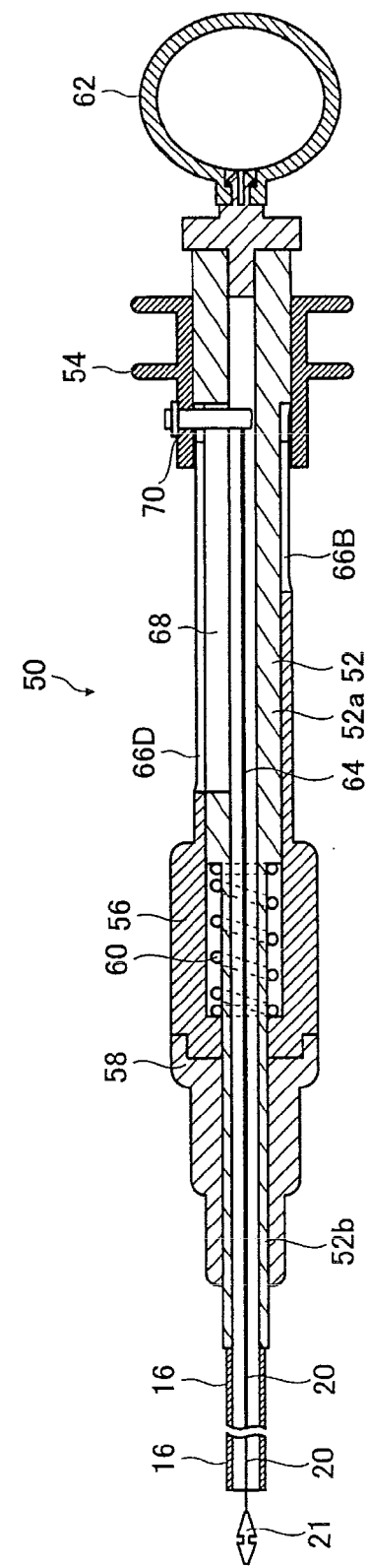
FIG. 5 is a cross-sectional view illustrating a schematic configuration of the manipulating handle illustrated in FIG. 1.
Figure 6:
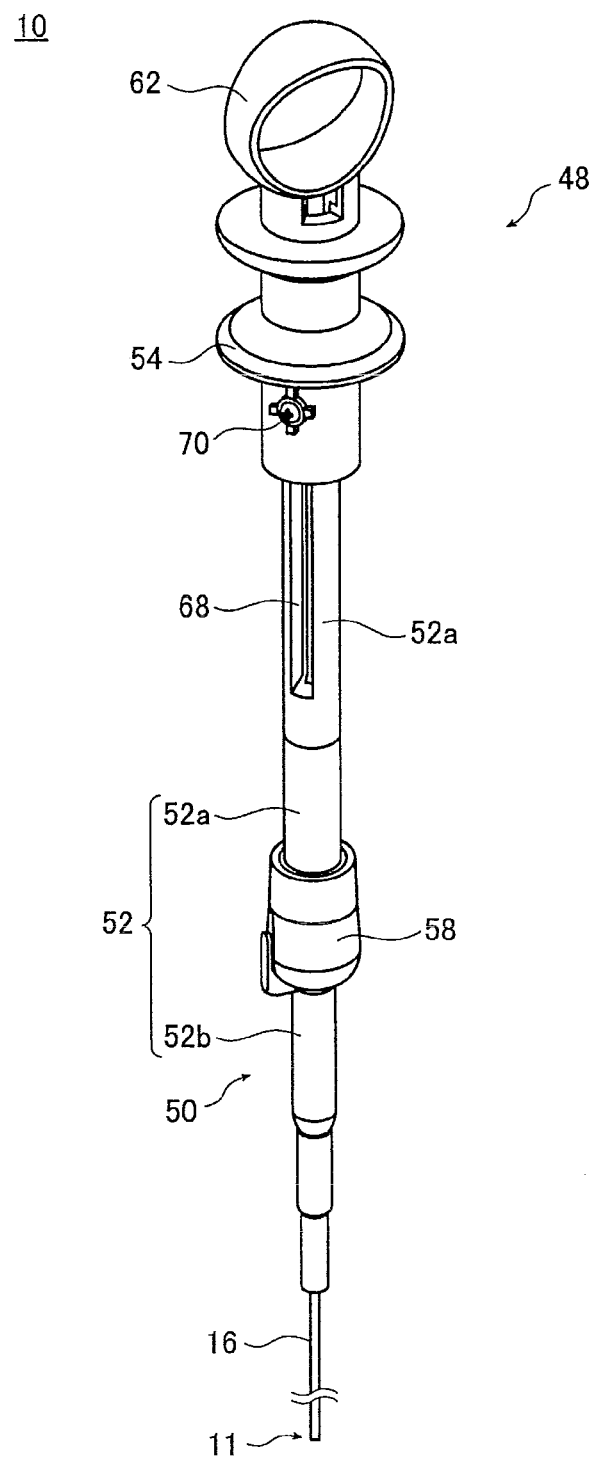
FIG. 6 is a perspective view illustrating a state in which a slider guide has been detached from the manipulating handle illustrated in FIG. 1.
Figure 7A:
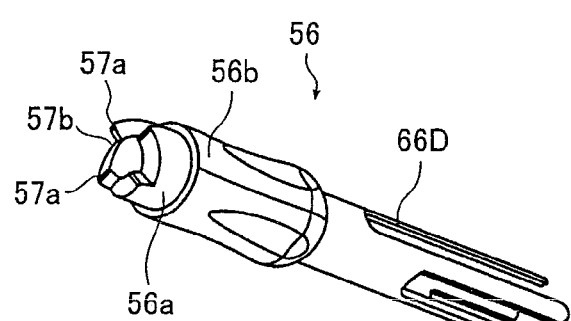
FIG. 7A is a perspective view illustrating the slider guide.
Figure 7B:
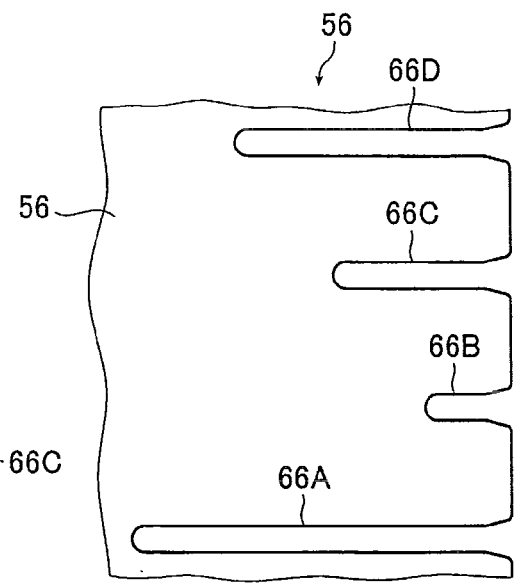
FIG. 7B is a partial developed view of an outer circumferential surface of the slider guide.
Figure 8:
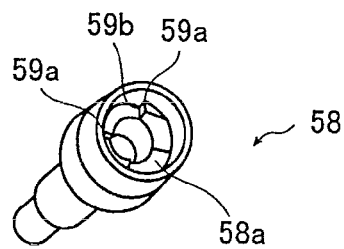
FIG. 8 is a perspective view illustrating a position regulating member.

FIG. 5 is a cross-sectional view diagrammatically illustrating a schematic configuration of the manipulating handle illustrated in FIG. 1. FIG. 6 is a perspective view illustrating the schematic configuration in a state in which a slider guide has been detached from the manipulating handle illustrated in FIG. 5. FIG. 7A is a perspective view illustrating a schematic configuration of the slider guide illustrated in FIG. 5. FIG. 7B is a partial developed view of the outer circumferential surface of the slider guide illustrated in FIG. 7A. FIG. 8 is a perspective view illustrating a schematic configuration of the position regulating member illustrated in FIG. 5.

As illustrated in FIG. 5, the manipulating handle 48 of the present invention includes the manipulating portion 50, the sheath 16, the manipulating wire 20, and the hook-shaped connected member (hook) 21 attached to the forward end of the manipulating wire 20. The manipulating portion 50 includes a handle main body 52, the slider 54, a slider guide 56, a position regulating member 58, a biasing spring 60, and a finger hook ring 62.

As illustrated in FIGS. 5 and 6, the handle main body 52 is a member in the form of a stepped circular tube including two cylindrical portions with different outer circumferential diameters. The cylindrical portion (larger-diameter portion) 52a with a larger outer circumferential diameter is provided with a groove (engagement groove) 68 extending in a center axis direction. In the handle main body 52, the forward end portion of the cylindrical portion (smaller-diameter portion) 52b with a smaller outer circumferential diameter is connected to the proximal end of the sheath 16. In the inside thereof, i.e., in the insides of the two cylindrical portions, the manipulating wire 20 inserted through the sheath 16 has been inserted to extend therethrough.

The slider 54 is a circular tubular member arranged around the outer circumference of the handle main body 52 so as to be movable over the outer circumferential surface of the handle main body 52 in the axial direction thereof. The slider 54 has a spool-like shape so as to be caught by a manipulator with a hooked finger, and easily moved in the advancing/retreating direction. The slider 54 includes a slider pin 70 attached to a part of the inner circumferential surface of the cylindrical member so as to protrude toward the center axis. The slider pin 70 is engaged with the groove 68 to fix the manipulating wire 20 inserted in and through the handle main body 52. The slider pin 70 is an engagement member fixed to the slider 54, and engaged with the groove 68 of the handle main body 52 for engagement.

By moving the slider 54 with respect to the handle main body 52 in the axial direction thereof, it is possible to move the manipulating wire 20 fixed to the slider 54 with respect to the sheath 16 in the axial direction thereof, and move the clip 12 connected to the forward end of the manipulating wire 20 with respect to the sheath 16.

As illustrated in FIGS. 5, 7A, and 7B, the slider guide 56 is a cylindrical member arranged to be circumferentially rotatable over the outer circumferential surface of the handle main body 52, and regulate the amount of movement of the slider 54 in the axial direction of the handle main body 52. The slider guide 56 is arranged over the outer circumferential surface of the handle main body 52 to be closer to the sheath 16 (the forward end of the sheath 16) than the slider 54. The slider guide 56 has a forward-end-side projecting joint portion 56a. The forward-end-side projecting joint portion 56a is fitted in a rotatable state into a proximal-end-side recessed joint portion 58a of the position regulating member 58 for regulating the position of the slider guide 56 described later, particularly the rotational position thereof, while being supported in a rotatable state by the handle main body 52.

The inner diameter of the forward end portion (joint portion 56a) of the slider guide 56 is substantially equal to the outer diameter of the smaller-diameter portion 52b of the handle main body 52 which is inserted through the slider guide 56. The slider guide 56 is supported by the handle main body 52, more specifically by the larger-diameter portion 52a and the smaller-diameter portion 52b thereof to be slidable in the circumferential (rotating) direction and the axial direction thereof. The outer diameter of the proximal-end-side portion of the slider guide 56 is slightly smaller than the inner diameter of the slider 54 to allow the proximal-end-side portion of the slider guide 56 to enter the interior of the slider 54 when the slider 54 moves toward the forward end. The slider guide 56 is manipulated by the manipulator to rotationally move with respect to the position regulating member 58 at the forward end thereof. Thus, the forward-end-side portion (the portion on the proximal-end side of the joint portion 56a) thereof is provided with the larger-diameter portion 56b larger in outer diameter than that of the proximal-end-side portion, and the outer surface of the larger-diameter portion 56b is provided with an inclined surface and depressions/protrusions in accordance with a finger, for easy gripping by the manipulator.

The slider guide 56 is provided with four slider guide grooves (position regulating grooves) 66A, 66B, 66C, and 66D extending along the center axis of the handle main body 52, and having different axial lengths for regulating the amount of movement of the slider by switching it among a plurality of stages, i.e., for regulating the amount of movement of the slider to two or more different amounts. The four slider guide grooves 66A, 66B, 66C, and 66D are formed at 90-degree intervals in the circumferential direction of the slider guide 56. The four slider guide grooves 66A, 66B, 66C, and 66D are also arranged such that, as the slider guide 56 is rotated, they have an overlapping positional relationship with the groove 68 of the handle main body 52 in the order of the slider guide groove 66A, the slider guide groove 66B, the slider guide groove 66C, the slider guide groove 66D, and the slider guide groove 66A again.

As illustrated in FIG. 7B, the four slider guide grooves 66A, 66B, 66C, and 66D have different lengths (i.e., the end portions (forward ends) thereof closer to the sheath 16 are at different positions). Specifically, the slider guide groove 66A is the longest, and the slider guide grooves 66D, 66C, and 66B are progressively shorter in this order.

The in-coming side (side with the slider 54) of each of the four slider guide grooves 66A, 66B, 66C, and 66D has been subjected to chamfering for allowing the slider pin 70 to easily enter each of the grooves without being caught by the other portion of the slider guide 56.

As the slider guide 56 is rotated into a predetermined orientation, the slider guide grooves 66A, 66B, 66C, and 66D in tern overlap the groove 68 of the handle main body 52.

The slider guide 56 regulates the movement limit position of the slider pin 70 moving along the groove 68 in the direction toward the sheath 16 moving in the axial direction of the handle main body 52 by the slider guide grooves 66A, 66B, 66C, and 66D overlapping the groove 68. That is, the slider pin 70 also functions as an engagement portion engaged with the slider guide groove for positional regulation.

As is described later in detail, as the slider guide 56 is rotated, the slider guide grooves 66A, 66B, 66C, and 66D overlap the groove 68 of the handle main body 52 in the order of the slider guide groove 66A, the slider guide groove 66B, the slider guide groove 66C, the slider guide groove 66D, and the slider guide groove 66A again.

The projecting joint portion 56a of the slider guide 56 has four indented projections 57a each formed at the contact surface (i.e., the surface of the slider guide 56 coming in contact with the position regulating member 58) thereof coming in contact with the recessed joint portion 58a of the position regulating member 58 to protrude toward the forward end in a direction parallel with the center axis of the handle main body 52, and have two tooth surfaces at different inclination angles in the circumferential direction with respect to the contact surface. The four projections 57a have the same shape of saw teeth. Each of the projections 57a has an indented shape, i.e., a triangular cross-sectional shape such that one of the tooth surfaces has a tapered shape at a gentle tilt angle, while the other tooth surface is at an inclination angle forming a substantially perpendicular step. The connection portions between the adjacent projections 57a serve as recesses 57b, and hence the four recesses 57b are formed.

On the other hand, as illustrated in FIGS. 5, 7A, and 8, the position regulating member 58 is a stepped cylindrical member for regulating the position of the slider guide 56, particularly the rotational position thereof. Through a through hole in the interior of the position regulating member 58, the smaller-diameter portion 52b of the handle main body 52 is inserted, and the inner circumferential surface of the through hole is fixed to the smaller-diameter portion 52b of the handle main body 52, whereby the position regulating member 58 is fixed to the handle main body 52 on the forward-end side of the slider guide 56. The position regulating member 58 includes, on its proximal-end side, the recessed joint portion 58a into which the forward-end-side projecting joint portion 56a of the slider guide 56 is fitted in a rotatable state.

The recessed joint portion 58a of the position regulating member 58 has four indented projections 59a which are each formed at the contact surface (i.e., the surface of the position regulating member 58 coming in contact with the slider guide 56) thereof coming in contact with the projecting joint portion 56a of the slider guide 56 to protrude toward the proximal end in a direction parallel with the center axis of the handle main body 52, and have two tooth surfaces at different inclination angles in the circumferential direction with respect to the contact surface. The four projections 59a have the same shape. Each of the projections 59a has an indented shape, i.e., a triangular cross-sectional shape such that one of the tooth surfaces has a tapered shape at a gentle inclination angle, while the other tooth surface is at an inclination angle forming a substantially perpendicular step. The connection portions between the adjacent projections 59a serve as recesses 59b so that the four recesses 59b are formed.

As described above, the joint portion 56a of the slider guide 56 also has the depressions/protrusions (the four recesses 57b and the four projections 57a) corresponding to the depressions/protrusions (the four recesses 59b and the four projections 59a) of the joint portion 58a of the position regulating member 58 which are formed at the contact surface with the position regulating member 58 such that the inclination angles of the tooth surfaces on both sides of the projections are reversed between the joint portion 56a and the joint portion 58a.

Therefore, the joint portion 58a of the position regulating member 58 is formed to regulate the positions of the slider guide 56 in the rotating direction and the axial direction such that any one of the four slider guide grooves 66A, 66B, 66C, and 66D of the slider guide 56 overlaps the groove 68 of the handle main body 52 when the joint portion 58a comes to a position where the depressions/protrusions thereof mesh with (are fit-engaged with) the depressions/protrusions of the joint portion 56a of the slider guide 56, i.e., when the projections 59a and the projections 57a have been fitted into the recesses 57b and the recesses 59b, respectively.

Thus, the position regulating member 58 and the slider guide 56 are capable of regulating the position of the slider guide 56 in at least one of the rotating direction and axial direction with the tapered shapes and the steps each provided at the contact surfaces thereof.

In addition, the position regulating member 58 and the slider guide 56 are fit-engaged with the indented depressions/protrusions of the two joint portions 58a and 56a. Thus, the slider guide 56 rotates only in one direction, specifically the direction in which the tooth surfaces (steps) at a sharp inclination angle of the projections 57a of the joint portion 56a of the slider guide 56 separate from the tooth surfaces (steps) at a sharp inclination angle of the projections 59a of the joint portion 58a of the position regulating member 58 in contact with the sharply inclined tooth surfaces of the projections 57a. That is, e.g., the projections 57a of the joint portion 56a of the slider guide 56 rotates, against the biasing force of the biasing spring 60 described later, in the direction from the recesses 59a of the joint portion 58a of the opposing position regulating member 58 toward the projections 59a thereof along the tooth surfaces (tapered surfaces) at a gentle inclination angle of the joint portion 58a. After that, the projections 57a move from the projections 59a to the next recesses 59b along the tooth surfaces (steps) at a sharp inclination angle so that the recesses 59a and the projections 57a mesh with each other.

The depressions/protrusions formed at each of the joint portion 58a of the position regulating member 58 and the joint portion 56a of the slider guide 56, and the tapered shapes and the steps formed in each of the contact surfaces of the position regulating member 58 and the slider guide 56 constitute a position regulating mechanism which regulates the position of the slider guide 56 in at least one of the rotating direction and the axial direction.

The biasing spring 60 is arranged to be wound around the outer periphery of the smaller-diameter portion 52b of the handle main body 52, and has one end portion in contact with the slider guide 56, and the other end portion in contact with the boundary surface (surface orthogonal to the center axis) between the smaller-diameter cylinder of the handle main body 52 and the larger-diameter cylinder thereof. The biasing spring 60 is a compression spring biasing the slider guide 56 toward the position regulating member 58.

Thus, by biasing the slider guide 56 toward the position regulating member 58 with the biasing spring 60, the slider guide 56 with the recesses and the projections meshing with those of the position regulating member 58 does not rotate with respect to the position regulating member 58 when an external force from the operator or the like is not exerted thereon.

The finger hook ring 62 is a ring-shaped member attached to the proximal end of the handle main body 52, i.e., attached to the end portion opposite to the end thereof connected to the sheath 16. The finger hook ring 62 is supported to be circumferentially rotatable with respect to the handle main body 52 around the center axis thereof. When manipulating the slider 54, the manipulator hooks his/her finger into the finger hook ring 62, and pulls the slider 54 toward the finger hook ring 62, thereby enabling adjustment of the amount of pulling the manipulating wire 20.

The portion of the manipulating wire 20 inserted in and through the manipulating portion 50 is fit-engaged with a reinforcing tube 64. The reinforcing tube 64 reinforces the manipulating wire 20 so that the manipulating wire 20 is not bent or curved, or does not break inside the handle main body 52 when it is moved by the slider 54.

The manipulating handle 48 and the manipulating portion 50 thereof are basically configured as described above.

When the groove 68 is overlapped by the slider guide groove 66A, if the slider 54 is moved till the slider pin 70 comes in contact with the end portion of the slider guide groove 66A closer to the sheath 16, the connected member 21 at the forward end of the manipulating wire 20 is caused to protrude from the forward end of the sheath 16. When the groove 68 is overlapped by the slider guide groove 66B, if the slider 54 is moved till the slider pin 70 comes in contact with the end portion of the slider guide groove 66B closer to the sheath 16, the first clip 12A is caused to protrude from the sheath 16 to such a position where it does not fall out of the sheath 16. This brings the first clip 12A into a clipping-manipulation capable state. Likewise, when the groove 68 is overlapped by the slider guide groove 66C, if the slider 54 is moved till the slider pin 70 comes in contact with the end portion of the slider guide groove 66C closer to the sheath 16, the second clip 12B is caused to protrude from the sheath 16 to such a position where it does not fall out of the sheath 16. This brings the second clip 12B into a clipping-manipulation capable state. Likewise, when the groove 68 is overlapped by the slider guide groove 66D, if the slider 54 is moved till the slider pin 70 comes in contact with the end portion of the slider guide groove 66D closer to the sheath 16, the third clip 12C is caused to protrude from the sheath 16 to such a position where it does not fall out of the sheath 16. This brings the third clip 12C into a clipping-manipulation capable state.

Preferably, each of the components of the manipulating handle 48 is formed of the following materials.

Metal members such as the sheath 16, the manipulating wire 20, and the slider pin 70 are preferably formed of an austenitic stainless steel (such as SUS 303, SUS 304, or SUS 316), or a precipitation-hardening stainless steel (such as SUS 630 or SUS 631). In terms of abrasion resistance, such metal members are more preferably formed of a precipitation-hardening stainless steel.

Resin components such as the slider 54, the handle main body 52, and the slider guide 56 are preferably formed of a resin with sterilizability such as polyphenylsulfone (PPSU), polysulfone (PSU), polyetherimide (PEI), polyetheretherketone (PEEK), polyphenylenesulfide (PPS), polyethersulfone (PES), or polyarylsulfone (PASF).

Preferably, the respective end surfaces of the slider pin and the slider guide grooves are formed of materials with excellent slidability and abrasion resistance because they contact each other, and a given level of force is exerted thereon. By forming the end surfaces of the slider pin and the slider guide grooves of such materials, it is possible to restrain the abrasion of the end surfaces thereof.

It is also preferable to deposit films of a fluorine resin or diamond-like carbon (DLC) on the end surfaces of the slider pin and the slider guide grooves. By depositing films of the compositions mentioned above, it is possible to improve abrasion resistance and slidability. In particular, by depositing DLC films, frictional resistance ($\mu$) is reduced, and surface hardness is increased to allow a significant improvement in abrasion resistance compared with the case where no film is deposited for the slider pin and the slider guide grooves.

The manipulating handle 48 is cleaned and sterilized upon each manipulation, it is preferably formed of a material with $\gamma$-line sterilizability, and therefore EOG sterilizability (resistance to ethylene oxide gas), and autoclave sterilizability (resistance to heat and vapor). When the manipulating handle 48 is designed to be disposable, it may also be formed of a material not having the properties mentioned above.

Next, the function of the successive clipping device illustrated in FIGS. 1 to 8 is described.

Figure 9:
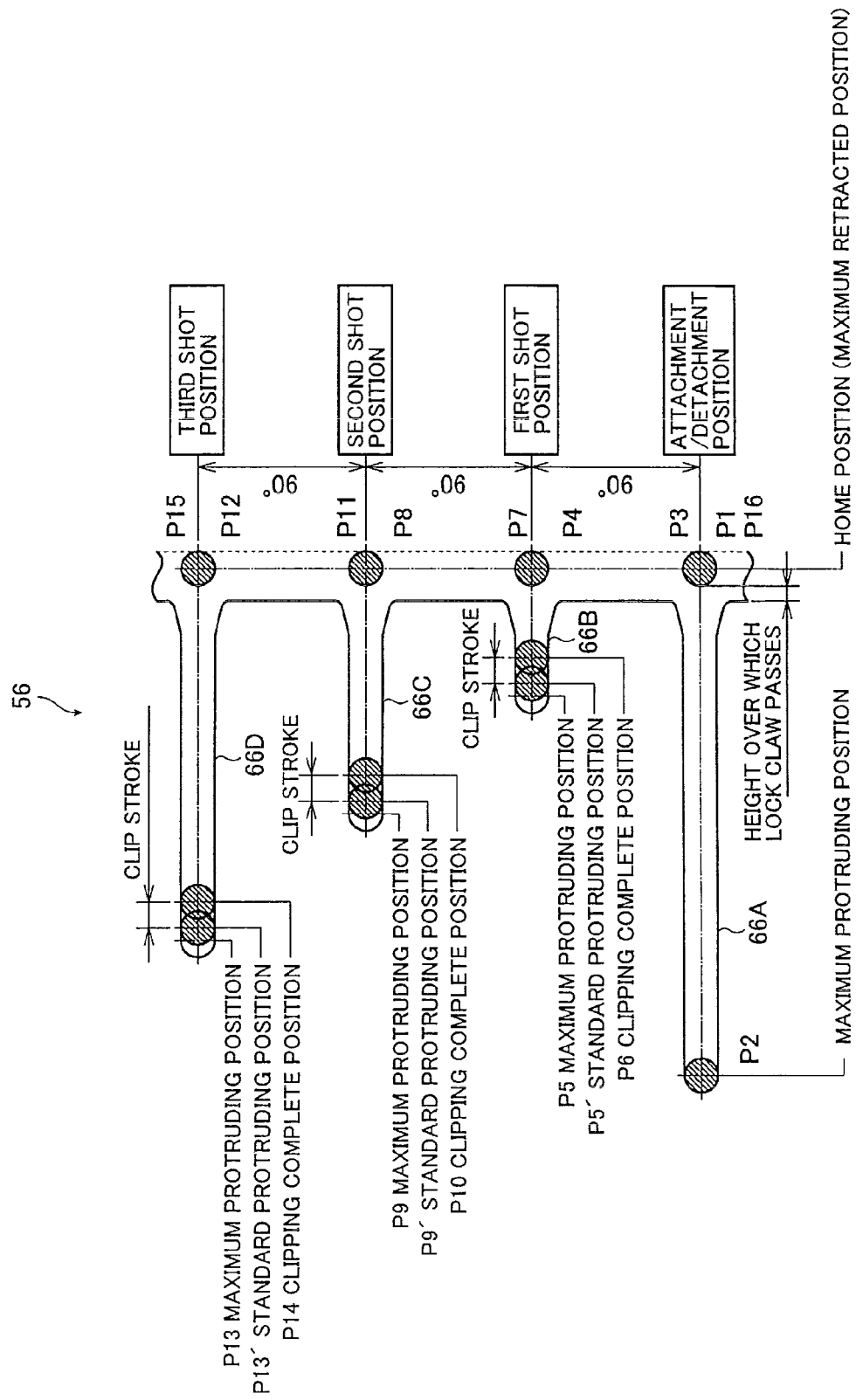
FIG. 9 is a partial developed view of the outer circumferential surface of the slider during an operation of clipping manipulation.

FIG. 9 is a partial developed view illustrating the positional relationship between the slider guide and the slider pin of the slider during an operation of clipping manipulation. FIGS. 10A to 10P are partial cross-sectional views progressively illustrating the states of the manipulation operating portion of the successive clipping device during the operation of clipping manipulation.

First, the slider guide 56 is oriented such that the slider guide groove 66A overlaps the groove 68, and the slider 54 is moved to the end portion of the movement region of the handle main body 52 which is closer to the finger hook ring 62 (the end portion of the movement region of the handle main body 52 which is closer to the finger hook ring 62 is hereinafter referred to as "home position"). That is, the slider pin 70 of the slider 54 is moved to the position P1 in FIG. 1. At this time, as illustrated in FIG. 10A, the manipulating wire 20 is in a state of being retracted within the sheath 16. This state is assumed to be an initial state.

Next, the slider 54 is moved to the end portion of the slider guide groove 66A closer to the sheath 16. That is, the slider pin 70 is moved to the position P2 in FIG. 9, and the connected member 21 of the manipulating wire 20 is caused to protrude from the forward end of the sheath 16, as illustrated in FIG. 10B.

After that, the connecting member 19 of the dummy clip 18 connected to the three clips is attached to the connected member 21 of the manipulating wire 20.

After the connecting member 19 of the dummy clip 18 connected to the three clips is attached to the connected member 21 of the manipulating wire 20, the slider 54 is moved to the home position. That is, the slider pin 70 is moved to the position P3 in FIG. 9 so that the clip series 13 including the three clips connected to the dummy clip 18 are stored in the sheath 16, as illustrated in FIG. 10C.

Then, the sheath 16 is inserted, from its forward end, into a forceps channel of an endoscope inserted in a living body or the like, and the forward end of the sheath is caused to reach the forward end of the inserted portion of the endoscope, and caused to protrude from the forward end of the endoscope.

After that, the slider guide 56 is rotated by 90° such that the slider guide groove 66B of the slider guide 56 overlaps the groove 68. As a result, the slider pin 70 is moved to the home position (position P4 in FIG. 9) on the extension line of the slider guide groove 66B.

Next, the slider 54 is moved to the end portion of the slider guide groove 66B closer to the sheath 16. That is, the slider pin 70 is moved to the position P5 in FIG. 9 and, as illustrated in FIG. 10D, the first clip 12A is caused to protrude from the forward end of the sheath 16 so that the skirt portions 38 of the first clip 12A are opened.

Here, a maximum protruding position is a position where the clip (which is the first clip 12A herein) does not fall out of the sheath 12, and the skirt portions 38 open to bring the clip into a usable state even when an amount of protrusion decreases due to variations in the dimensions of the components and to the difference between the inner and outer circumferences of the wire and the sheath.

After that, the slider 54 is moved toward the finger hook ring 62 to a standard protruding position. That is, the slider pin 70 is moved to the position P5' in FIG. 9 to bring the skirt portions 38 of the first clip 12A into contact with the forward end of the sheath 16, as illustrated in FIG. 10E. By pulling the slider pin 70 to the standard protruding position, even when the first clip 12A is excessively protruding, the skirt portions 38 can be brought into contact with the forward end of the sheath 16 to establish a state in which manipulation with the first clip 12A is possible.

Thus, the distance from the maximum protruding position to the standard protruding position serves as a buffer for variations in the dimensions of the components and for the difference between the inner and outer circumferences of the wire and the sheath. By causing the first clip 12A to temporarily protrude to the maximum protruding position, the skirt portions 38 can be opened irrespective of an error and, by subsequently pulling the slider pin 70 to the standard protruding position, the skirt portions 38 can be brought into contact with the forward end of the sheath 16 irrespective of an error.

After that, the clipping device 10 is moved to press the claw portions 22 of the diverged first clip 12A against an affected site such as a diseased site desired to be subjected to clipping manipulation, and the slider 54 is moved toward the finger hook ring 62 to a clipping complete position. That is, the slider pin 70 is moved to the position P6 in FIG. 9.

At this time, in the connection ring 14A protruding from the forward end of the sheath 16, the skirt portions 38 are opened, and the pressure retention of the clip 12A by the skirt portions 38 has been cancelled. Further, the skirt portion 38 is opened at the forward end of the sheath 16, and hence the connection ring 14A is prevented from retreating into the sheath 16. As a result, the foremost clip 12A retreats with respect to the connection ring 14A. The clamping portion 40 at the forward end of the connection ring 14A is pushed along the proximal portions 28b of the arm portions 28 of the first clip 12A from the crossing portion 26 to a position immediately under the projections 30, whereby the claw portions 22 clip the diseased site, and the clamping of the first clip 12A by the clamping ring 40 at the forward end of the connection ring 14A is completed.

At the same time, the engagement portion between the first clip 12A and the second clip 12B comes out of the rear end of the connection ring 14A. When the engagement portion between the first clip 12A and the second clip 12B exit the connection ring 14A, the arm portions 28 are diverged till abutting the inner wall of the sheath 16 by the resilient force of the second clip 12B, and the distance between the claw portions 22 increases to be larger than the width of the turned portion 24 of the first clip 12A so that the first clip 12A is disconnected from the second clip 12B. As a result, as illustrated in FIG. 10F, the first clip 12A and the connection ring 14A are capable of getting out of the sheath 16, and the clipping manipulation to the diseased site with the first clip 12A and the clamping ring 40 at the forward end of the connection ring 14A is completed.

On the other hand, the subsequent clips 12B and 12C are retained by the connection rings 14B and 14C whose skirt portions 38 are closed so as not to move with respect to the connection rings 14B and 14C in the rotating direction and in the advancing/retreating direction. Further, by the diverging force (biasing force) of the respective claw portions 22 of the clip 12B and the third clip 12C engaged with the clip 12B and of the claw portions of the dummy clip 18, the claw portions 22 have been pressed against the inner walls of the second regions 34 of the connection rings 14B and 14C, and therefore the frictional force between the clips 12B and 12C and the connection rings 14B and 14C have been increased. As a result, the connection rings 14B and 14C move with the movement of the clips 12B and 12C.

That is, the clips 12B and 12C and the connection rings 14B and 14C other than the foremost first clip 12A and the connection ring 14A retaining the first clip 12A integrally perform advancing/retreating movement with respect to the sheath 16, and the connection state between the clips 14B and 14C and the dummy clip 18 is maintained by the connection rings 14B and 14C.

When the clipping manipulation with the first clip 12A and the connection ring 14A is completed, the slider 54 is moved to the home position, i.e., the slider pin 70 is moved to the position P7 in FIG. 9. As a result, as illustrated in FIG. 10G, the clips 12B and 12C are brought into the state of being retracted within the sheath 16.

After that, the slider guide 56 is rotated by 90° such that the slider guide groove 66C of the slider guide 56 overlaps the groove 68. As a result, the slider pin 70 is moved to the home position (position P8 in FIG. 9) on the extension line of the slider guide groove 66C.

Next, the slider guide 54 is moved to the end portion of the slider guide groove 66C closer to the sheath 16. That is, the slider pin 70 is moved to the position P9 in FIG. 9 and, as illustrated in FIG. 10H, the second clip 12B is caused to protrude from the forward end of the sheath 16 so that the skirt portions 38 of the second clip 12B are opened.

Then, the slider 54 is moved toward the finger hook ring 62 to the standard protruding position. That is, the slider pin 70 is moved to the position P9' in FIG. 9 to bring the skirt portions 38 of the second clip 12B into contact with the forward end of the sheath 16, as illustrated in FIG. 10I.

After that, the clipping device 10 is moved to press the claw portions 22 of the diverged second clip 12B against the site desired to be subjected to clipping treatment, and the slider 54 is moved toward the finger hook ring 62 to the clipping complete position. That is, the slider pin 70 is moved to the position P10 in FIG. 9.

By moving the slider 54 to the clipping complete position, clamping by the second clip 12B is completed, and the second clip 12B is disconnected from the third clip 12C. As a result, as illustrated in FIG. 10J, the second clip 12B and the connection ring 14B are capable of getting out of the sheath 16, and the clipping manipulation to the diseased site with the second clip 12B and the clamping ring 40 at the forward end of the connection ring 14B is completed.

When the clipping manipulation with the second clip 12B and the connection ring 14B is completed, the slider 54 is moved to the home position, i.e., the slider pin 70 is moved to the position P11 in FIG. 9. As a result, as illustrated in FIG. 10K, the third clip 12C is brought into the state of being retracted within the sheath 16.

Then, the slider guide 56 is rotated by 90° such that the slider guide groove 66D of the slider guide 56 overlaps the groove 68. As a result, the slider pin 70 is moved to the home position (position P12 in FIG. 9) on the extension line of the slider guide groove 66D.

Next, the slider 54 is moved to the end portion of the slider guide groove 66D closer to the sheath 16. That is, the slider pin 70 is moved to the position P13 in FIG. 9 and, as illustrated in FIG. 10L, the third clip 12C is caused to protrude from the forward end of the sheath 16 so that the skirt portions 38 of the third clip 12C are opened.

Then, the slider 54 is moved toward the finger hook ring 62 to the standard protruding position. That is, the slider pin 70 is moved to the position P13' in FIG. 9 to bring the skirt portions 38 of the third clip 12C into contact with the front end of the sheath 16, as illustrated in FIG. 10M.

After that, the clipping device 10 is moved to press the claw portions 22 of the diverged third clip 12C to the site desired to be subjected to clipping manipulation, and the slider 54 is moved toward the finger hook ring 62 to the clipping complete position. That is, the slider pin 70 is moved to the position P14 in FIG. 9.

By moving the slider 54 to the clipping complete position, clamping by the third clip 12C is completed, and the third clip 12C is disconnected from the dummy clip 18. As a result, as illustrated in FIG. 10N, the third clip 12C and the connection ring 14C are capable of getting out of the sheath 16, and the clipping manipulation to the diseased site with the third clip 12C and the clamping ring 40 at the forward end of the connection ring 14C is completed.

When the clipping manipulation with the third clip 12C and the clamping ring 40 at the forward end of the connection ring 14C is completed, the slider 54 is moved to the home position, i.e., the slider pin 70 is moved to the position P15 in FIG. 9. As a result, as illustrated in FIG. 10O, the dummy clip 18 is brought into the state of being retracted within the sheath 16.

Then, the slider guide 56 is rotated by 90° such that the slider guide groove 66A of the slider guide 56 overlaps the groove 68. As a result, the slider pin 70 is moved to the home position (position P16 in FIG. 9) on the extension line of the slider guide groove 66A.

After that, the sheath 16 is pulled out of the endoscope.

After the sheath 16 is pulled out, the slider 54 is further moved to the end portion of the slider guide groove 66A closer to the sheath 16. That is, the slider pin 70 is moved to P2 in FIG. 9 and, as illustrated in FIG. 10P, the connected member 21, the dummy clip 18, and the connecting member 19 are caused to protrude from the forward end of the sheath 16.

After that, when the manipulation is completed, the dummy clip 18 and the connecting member 19 are detached, and the slider 54 is moved to the home position.

On the other hand, when clipping manipulation is performed with other clips, the dummy clip 18 and the connecting member 19 are detached, then the connecting member 19 of the dummy clip 18 connected to other three clips 12 is attached to the connected member 21, and the steps described above are repeatedly performed.

In this manner, the clipping manipulation using the clipping device 10 is performed with respect to the diseased site.

Thus, with the clipping device, it is possible to effect clipping a plurality of times without pulling out the sheath. By connecting the individual clips, and successively effecting clipping, it is possible to manipulate clipping with a plurality of clips with a single manipulating wire.

By providing the slider guide, and regulating the amount of movement of the slider which manipulates the advance/retreat of the clip in accordance with the clip (i.e., in accordance with whether the clip is the first clip, the second clip, or the like), it is possible to cause the clip to protrude from the sheath only by a proper distance without adjustment by the manipulator, and increase manipulating properties. In addition, it is possible to prevent the clip from falling out by excessively protruding, and prevent faulty manipulation.

In addition, clipping manipulation can be performed only by the manipulation of rotating the single slider guide and the manipulation of pulling the single slider, and hence it is possible, in this regard, to reduce the probability of the occurrence of faulty manipulation.

Moreover, the plurality of clips can be manipulated in succession with the single slider guide and the single slider, and hence it is possible to reduce the possibility of mistaking the order of the clips to be used.

Further, the plurality of clips can be manipulated with the single manipulation mechanism, and hence it is possible to reduce the number of items constituting the manipulating handle and the clipping device, device cost, and the number of production steps.

Embodiment 2

In the manipulating handle of Embodiment 1, the distance from the maximum protruding position to the standard protruding position of each of the slider guide grooves is used as the buffer for variations in the dimensions of the components and for the difference between the inner and outer circumferences of the wire and the sheath, and the skirt portions of the clip are shaped to open irrespective of an error. However, the region of the slider guide groove extending from the maximum protruding position to the standard protruding position may be curved in the rotating direction of the slider.

Figure 11:
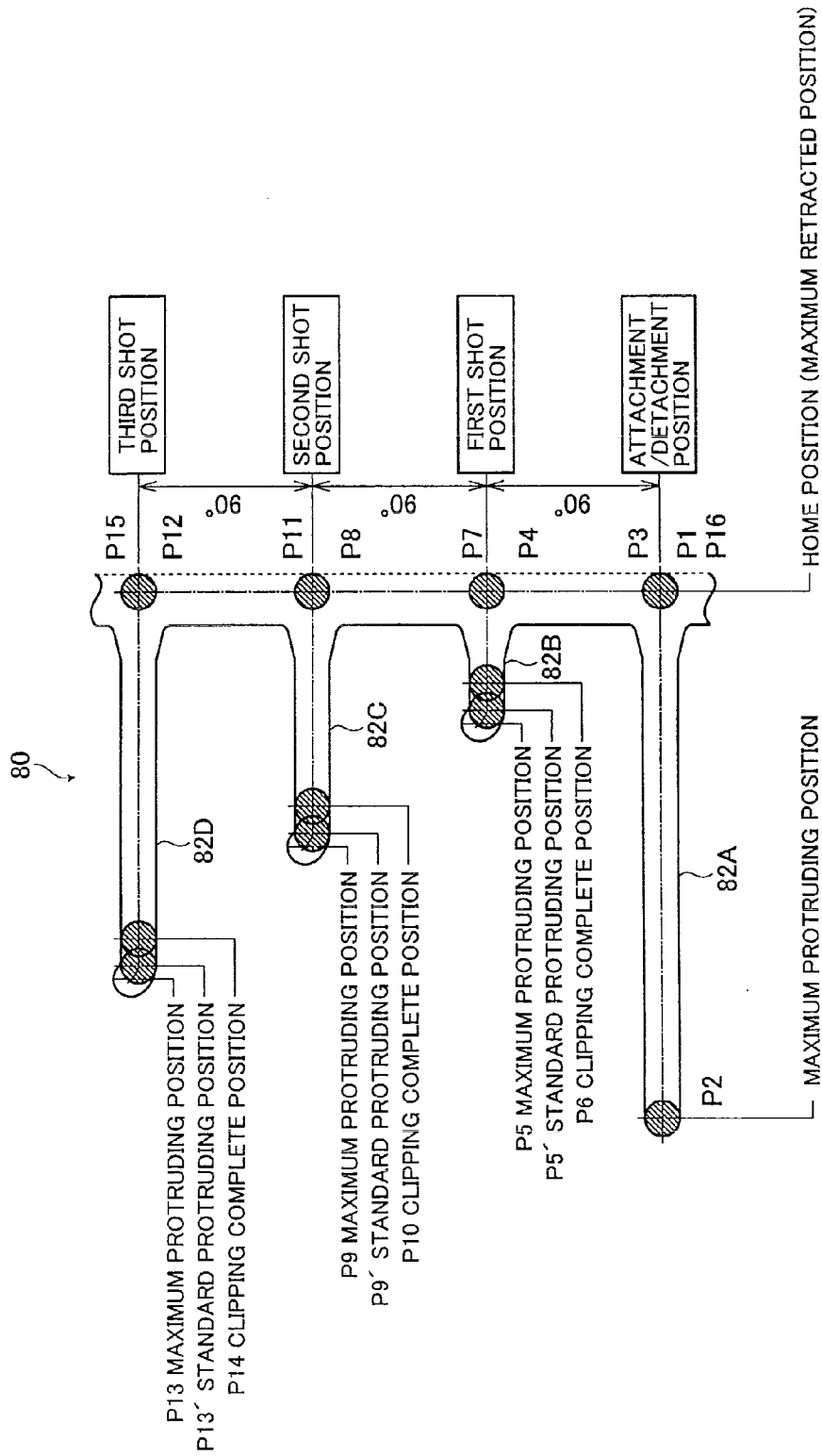
FIG. 11 is a partial developed view of the outer circumferential surface of a slider guide used in Embodiment 2.

FIG. 11 is a partial developed view of the outer circumferential surface of a slider guide used in a manipulating handle according to Embodiment 2.

Figure 10:
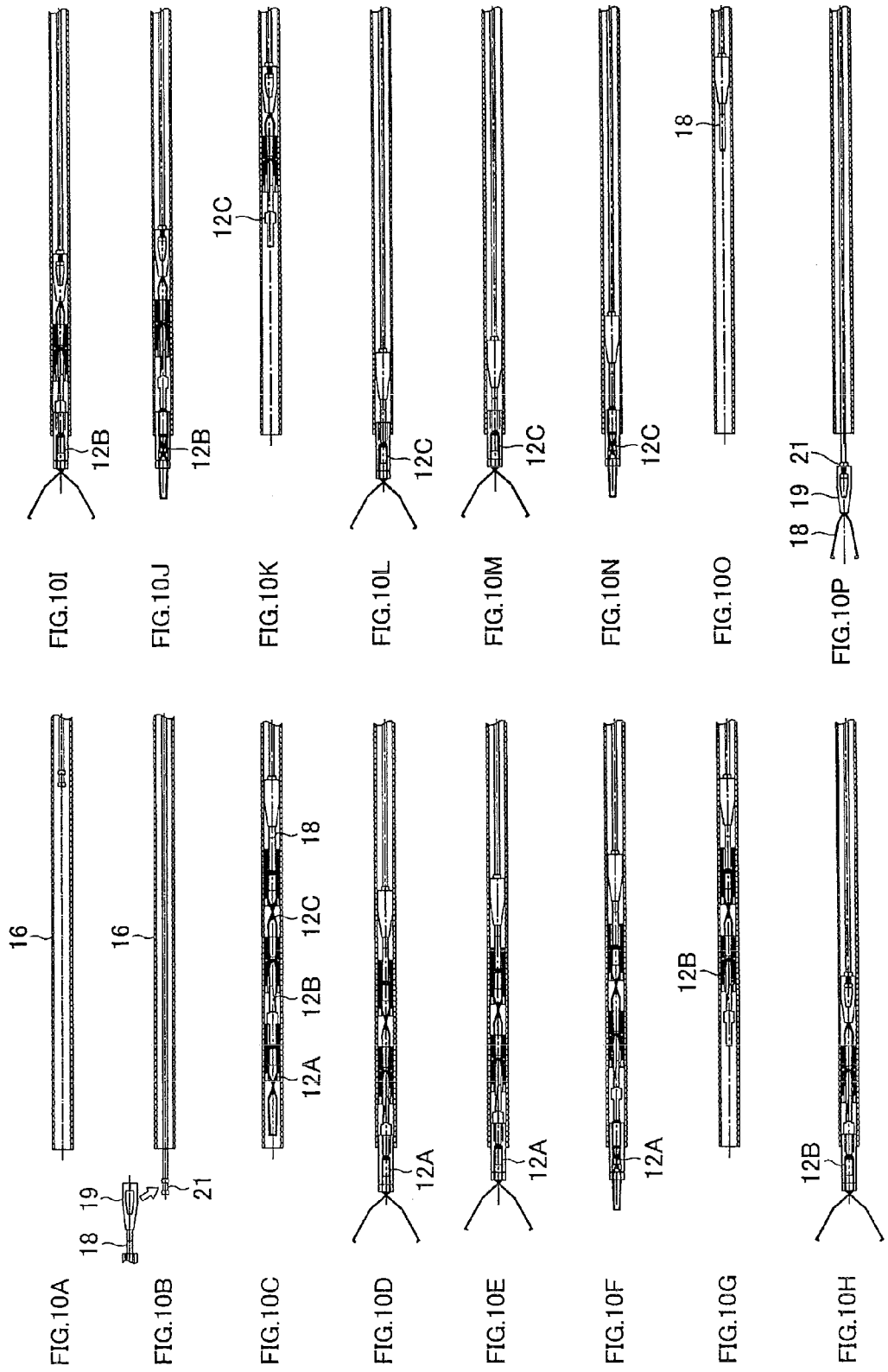
FIGS. 10A to 10P are partial cross-sectional views progressively illustrating the states of the successive clipping device of Embodiment 1 during the operation of clipping manipulation.

A slider guide 80 having slider guide grooves 82A, 82B, 82C, and 82D illustrated in FIG. 11 has the same configuration as that of the slider guide 56 having the slider guide grooves 66A, 66B, 66C, and 66D illustrated in FIGS. 7A, 7B, and 10 except for the shape of each of the grooves. Therefore, instead of the slider guide 56, the slider guide 80 can be used in the entirely same manner in the manipulating portion 50, the manipulating handle 48, and the clipping device 10 of the illustrated example.

As illustrated in FIG. 11, the slider guide grooves 82B, 82C, and 82D of the slider guide 80 have linear shapes from the respective end portions (P4, P8, and P12) on the home-position side to the respective standard protruding positions (P5', P9', and P13'), and shapes curved in the rotating direction (i.e., shapes curved at predetermined angles in the rotating direction with respect to the straight lines) from the respective standard protruding positions (P5', P9', and P13') to the respective maximum protruding positions (P5, P9, and P13).

By thus imparting the shapes curved in the rotating direction to the portions extending from the standard protruding positions to the maximum protruding positions, it is possible for the manipulator to clearly recognize each of the standard protruding positions from the state of the slider guide 80 and from the force acting on the slider 54.

In addition, even when the slider 54 has been moved to the maximum protruding position, it is possible to allow the slider 54 to automatically return to the standard protruding position under the restoring force of the slider guide 80. Therefore, the manipulator can move the slider 54 to the standard protruding position by temporarily moving the slider 54 to the maximum protruding position, and then merely releasing his/her hand from the slider 54.

It is also possible to move the slider 54 to the maximum protruding position only when the skirt portions 38 of the clips 12 do not open.

In the slider guide 80, each of the slider guide grooves is shaped such that the portion thereof extending from the standard protruding position to the maximum protruding position is curved in the rotating direction. However, the shape of the slider guide groove is not limited thereto. The slider guide groove may also be elongated beyond the maximum protruding position, have a linear shape from the home-position-side end portion to the maximum protruding position, and have a shape curved ahead of the maximum protruding position in the rotating direction.

In this case, if the skirt portions of the clip do not protrude from the forward end of the sheath even when the slider is moved to the maximum protruding position for such reasons that the deformation of the manipulating wire surpasses the range of an error, or the clip does not move in the sheath from any cause, the skirt portions of the clip may be caused appropriately to protrude from the forward end of the sheath by moving the slider to the portion curved ahead of the maximum projection portion in the rotating direction.

By thus providing the groove portion curved ahead of the maximum protruding position in the rotating direction, it is possible to respond to unexpected situations. In addition, by curving the groove portion ahead of the maximum protruding position in the rotating direction, the slider can be easily adjusted so as not to move ahead of the maximum protruding position during normal use.

Embodiment 3

In Embodiments 1 and 2, the slider guides provided with the slider guide grooves are used. However, it is also possible to form a slider guide with steps corresponding to the respective protruding positions of the individual clips instead of the slider guide grooves.

Figure 12:
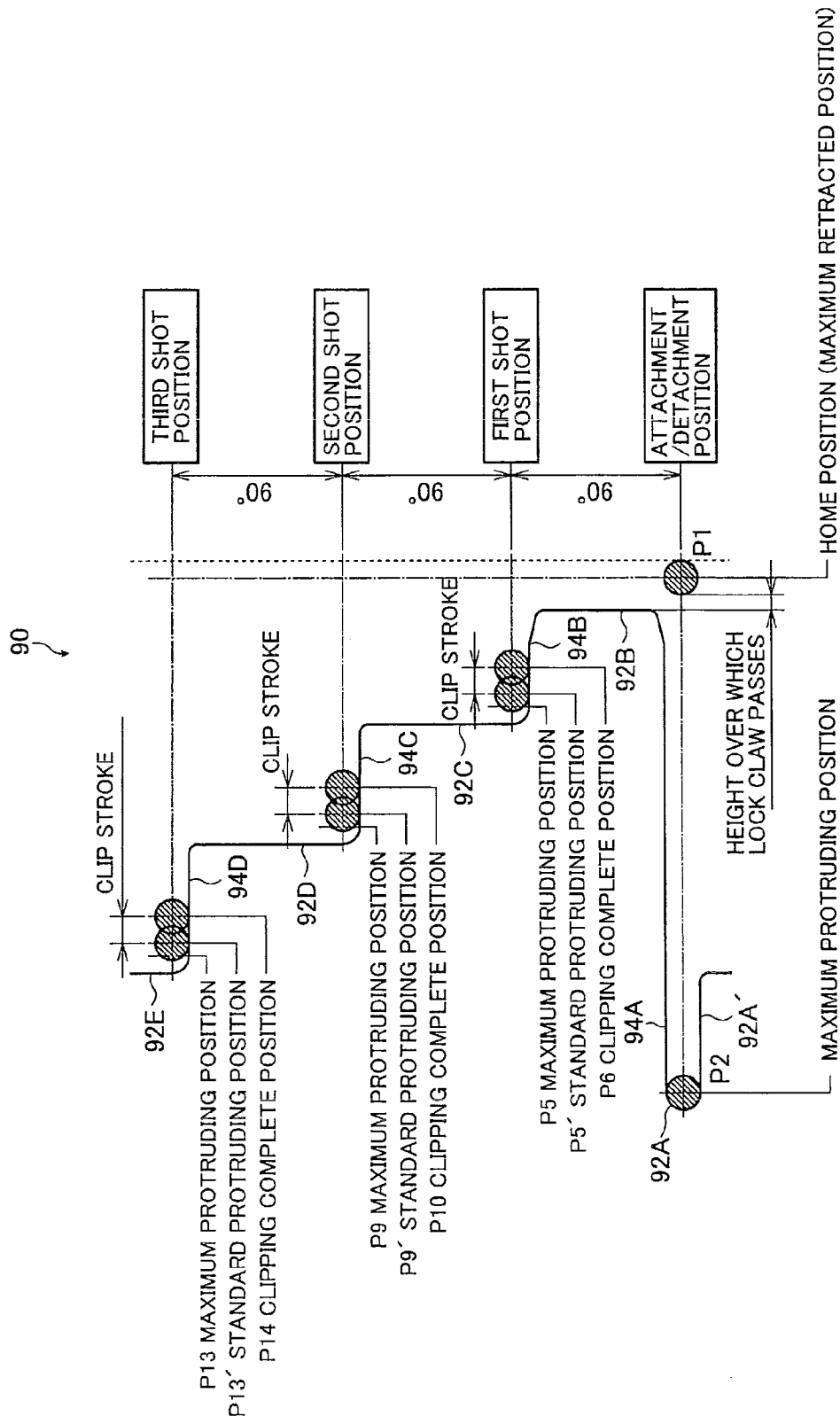
FIG. 12 is a partial developed view of the outer circumferential surface of a slider guide used in Embodiment 3.

FIG. 12 is a partial developed view of the outer circumferential surface of a slider guide used in a manipulating handle according to Embodiment 3.

A slider guide 90 illustrated in FIG. 12 has the same configuration as that of the slider guide 56 in FIGS. 7A, 7B, and 10 except for using the steps instead of the slider guide grooves. Therefore, instead of the slider guide 56, the slider guide 90 can be used in the entirely same manner in the manipulating portion 50, the manipulating handle 48, and the clipping device 10 of the illustrated example.

As illustrated in the developed view of FIG. 12, a slider guide 90 is provided with five short sides 92 (sides 92A, 92B, 92C, 92D, and 92E) closer to the finger hook ring 62 (closer to the proximal end thereof), which are basically parallel with a plane orthogonal to the center axis, and at different positions in the center axis direction of the handle main body 52. Among the five sides 92, the side 92A is closest to the forward end of the sheath, and the sides 92E, 92D, 92C, and 92B are progressively closer to the finger hook ring in this order. The five sides 92 are formed in the order of the sides 92A, 92B, 92C, 92D, and 92E in the rotating direction, with the sides 92E and 92A adjoining and linked to each other.

The position of the side 92A in the center axis direction of the handle main body is the same as that of the sheath-side (forward) end portion of the slider guide groove 66A. The position of the side 92B in the center axis direction of the handle main body is the position of the side between the slider guide grooves 66A and 66B. The position of the side 92C in the center axis direction of the handle main body is the same as that of the sheath-side end portion of the slider guide groove 66B. The position of the side 92D in the center axis direction of the handle main body is the same as that of the sheath-side end portion of the slider guide groove 66C. The position of the side 92E in the center axis direction of the handle main body is the position of the sheath-side end portion of the slider guide groove 66D.

A step 94A is formed between the sides 92A and 92B. A step 94B is formed between the sides 92B and 92C. A step 94C is formed between the sides 92C and 92D. A step 94D is formed between the sides 92D and 92E. Further, a step 94A' is formed between the sides 92E and 92A. The steps 94A, 94B, 94C, and 94D of the slider guide 90 illustrated in FIG. 12 correspond to the slider guide grooves 66A, 66B, 66C, and 66D of the slider guide 56 illustrated in FIG. 10, respectively.

By rotating the slider guide 90 having such steps to switch the step and the side which overlap the groove 68 of the handle main body 52, it is possible to regulate the position of the slider pin 70 in the center axis direction of the handle main body 52. That is, it is possible to individually set the movement limit position of the slider pin 70 for each of the sides (steps) of the slider guide 90, regulate the position of the slider 54 corresponding to the clip 12, and prevent the clip 12 from jumping out of the sheath 16 in the same manner as with the slider guide grooves of the slider guides 56 and 80.

In addition, by forming the slider guide into a stepped shape, it is possible to rotate the slider guide, and make preparations for clipping with the next clip without returning the slider to the home position. This allows a reduction in the amount of manipulation by the manipulator.

Embodiment 4

In the clipping device 10 of Embodiment 1, the position regulating member 58 is provided between the slider guide 56 and the handle main body 52 so that one of the slider guide grooves (66A to 66D) properly overlaps the groove 68 of the handle main body 52 so as to improve the manipulating properties. However, the present invention is not limited thereto. The position regulating member is not necessarily provided, though it is necessary for the manipulator to perform the manipulation of causing one of the slider guide grooves to overlap the groove 68 of the handle main body 52.

In addition, although the slider guide is caused to rotate only in one direction by the position regulating member 58, the present invention is not limited thereto. The slider guide may be caused to rotate bidirectionally.

In Embodiment 1, the position regulating member is provided with the function of regulating both of the stopping position of the slider guide and the rotating direction of the slider guide. However, the position regulating member may be provided with the function of regulating only one of them.

For example, in the case of providing the position regulating member with the function of regulating the rotating direction of the slider guide to one direction as the position regulating mechanism, the contact surfaces of the position regulating member and the slider guide may be provided with a configuration (i.e., a ratchet configuration) in which a plurality of indented depressions/protrusion are formed in the circumferential direction, irrespective of the positions of the slider guide grooves.

On the other hand, in the case of providing the position regulating member only with the function of regulating the stopping position of the slider guide, as the position regulating mechanism, it may be configured such that the slider guide is provided with recesses at intervals corresponding to the slider guide grooves, a biasing force toward the slider guide is imparted to one portion of the handle main body, movable projections are provided, and the recesses and the projections mesh with each other at the position where one of the slider guide grooves overlaps the groove of the handle main body. The positions where the recesses and projections are formed may also be reversed.

FIG. 13 is a cross-sectional view illustrating a position regulating mechanism 100 applied to the manipulating handle of Embodiment 4. The position regulating mechanism 100 is provided in the handle main body 52 in Embodiment 1, and has a projection 102 biased toward the slider guide 56, and recesses 104 formed at intervals (at four positions in this embodiment) corresponding to the respective slider guide grooves 66A to 66D in the outer circumferential surface of the slider guide 56 in the same cross section as that in which the projection 102 is formed. The projection 102 is a member to which a biasing force toward the slider guide 56 is imparted, and which is movable in a direction in which it comes in contact with or separates from the slider guide 56. Specifically, the projection 102 is a ball 102a (i.e., a ball plunger) biased by a biasing spring 102b toward the slider guide 56.

The four recesses 104 are formed such that, when one of the four recesses 104 overlaps (is fit-engaged with) the projection 102, the groove 68 of the handle main body 52 is overlapped by the corresponding one of the slider guide grooves 66A to 66D.

By thus configuring the position regulating mechanism 100, it is possible to regulate the position of the slider guide 56 such that one of the slider guide grooves 66A to 66D overlaps the groove 68 of the handle main body 52, and the slider guide 56 stops at the overlapping position.

In the position regulating mechanism 100 illustrated in FIG. 13, the projection 102 includes the ball plunger. However, as in a position regulating mechanism 110 illustrated in FIGS. 14A and 14B, a projection 112 may be an engagement claw made of resin, and including a cantilever 114 biased toward the slider guide 56, and a protrusion 116 provided at the surface of the cantilever 114 coming in contact with the slider guide 56 to be fit-engaged with one of the recesses 104 of the slider guide 56. In this case, it is necessary to provide the handle main body 52 with a space which allows the cantilever 114 to move.

A position regulating mechanism 120 illustrated in FIGS. 15A and 15B has a projection 122 provided at the outer circumferential surface of the slider guide 56, and recesses 124 formed at intervals (at four positions in this embodiment) corresponding to the respective slider guide grooves 66A to 66D in the inner circumferential surface of the handle main body 52 in the same cross section in which the projection 122 is formed. The projection 122 is a member to which a biasing force toward the handle main body 52 is imparted, and which is movable in a direction in which it comes in contact with and separates from the slider guide 56. Specifically, the projection 122 is an engagement claw made of resin, and including a cantilever 126 biased toward the handle main body 52, and a protrusion 128 provided at the surface of the cantilever 126 coming with contact with the handle main body 52 to be fit-engaged with one of the recesses 124 of the handle main body 52.

The cantilever 126 has a longitudinal direction corresponding to a direction parallel with the axis of the handle main body 52, and the longitudinal end portion thereof serves as a proximal end.

Thus, the position regulating mechanism may also be configured such that the projection is provided in the slider guide 56, and the recesses are formed in the handle main body 52.

In the position regulating mechanism 120 illustrated in FIGS. 15A and 15B, the cantilever 126 constituting the projection 122 has a cantilever configuration in which the direction parallel with the axis of the handle main body 52 serves as the longitudinal direction, and the longitudinal end portion serves as the proximal end. However, as illustrated in FIGS. 16A and 16B, it is also possible to provide a cantilever 134 of a projection 132 of a position regulating mechanism 130, which is curved along the circumferential direction of the handle main body 52.

In each of the position regulating mechanisms 100, 110, 120, and 130, the rotating direction of the slider guide 56 is not regulated. However, it is also possible to regulate the rotating direction of the slider guide to one direction by changing the shapes of the recesses and the projections (into, e.g., asymmetrical shapes).

FIGS. 17A to 17D are partial cross-sectional views illustrating respective modifications of the positional regulating mechanisms 100, 110, 120, and 130.

A position regulating mechanism 101 illustrated in FIG. 17A is a modification of the position regulating mechanism 100 illustrated in FIG. 13. A protrusion (specifically, a protrusion having a surface perpendicular to a tangential line of a ball 136a at the downstream end portion of the slider guide 56 in the rotating direction) 136b is provided at a part of the surface of the ball 136a of a ball plunger constituting a projection 136 which is in contact with the slider guide 56. As a matter of course, at this time, the slider guide 56 is provided with recesses 137 which are each fit-engaged with the ball 136a having the protrusion 136b. As a result, it is possible to cause the slider guide 56 to rotate only in a direction from the side without the protrusion 136b toward the side with the protrusion 136b, i.e., in the direction indicated by the mark "o" in the drawing, and prevent the slider guide 56 from rotating in the reverse direction, i.e., in the direction indicated by the mark "×" in the drawing.

A position regulating mechanism 111 illustrated in FIG. 17B is a modification of the position regulating mechanism 110 illustrated in FIGS. 14A and 14B. At one circumferential end surface of a protrusion 138a of a projection 138, a tapered surface at a gentle inclination is formed, while a step at a sharp inclination is formed in the other circumferential end surface thereof. At this time, the slider guide 56 is provided with recesses 139 which are each fit-engaged with the protrusion 138a. As a result, it is possible to cause the slider guide 56 to rotate from the side with the tapered surface at a gentle inclination angle toward the side with the step at a sharp inclination (in the direction indicated by the mark "o" in the drawing), and prevent the slider guide 56 from rotating in the reverse direction (the direction indicated by the mark "×" in the drawing).

A position regulating mechanism 121 illustrated in FIG. 17C is a modification of the position regulating mechanism 120 illustrated in FIGS. 15A and 15B. At one circumferential end surface of a protrusion 140a of a projection 140, a tapered surface at a gentle inclination is formed, while a step at a sharp inclination is formed at the other end surface thereof. The slider guide 56 is provided with recesses 141 which are each fit-engaged with the protrusion 140a.

A position regulating mechanism 131 illustrated in FIG. 17D is a modification of the position regulating mechanism 130 illustrated in FIGS. 16A and 16B. At one circumferential end surface of a protrusion 142a of a projection 142, a tapered surface at a gentle inclination is formed, while a step at a sharp inclination is formed at the other end surface thereof. The slider 56 is provided with recesses 143 which are each fit-engaged with the protrusion 142a.

By thus configuring the protrusions 140a and 142a of the projections 140 and 142 such that the upstream end portions thereof in the rotating direction of the slider guide 56 have steps, e.g., plan shapes perpendicular to the circumferential direction (tangential lines of the rotator), the rotation of the slider guide 56 can be regulated to one direction (the direction indicated by the mark "o" in the drawing).

It is to be noted that a method, means, and mechanism for regulating the stopping position of the slider guide and the rotating direction of the slider guide are not limited to the method, means, and mechanism described above, and various methods, means, and mechanisms each having an interlocking function can be used.

Embodiment 5

In the manipulating handle of the present invention, it is preferable to provide a mechanism for transmitting that the slider pin has reached the clipping complete position to the manipulator via the slider.

Figure 19:
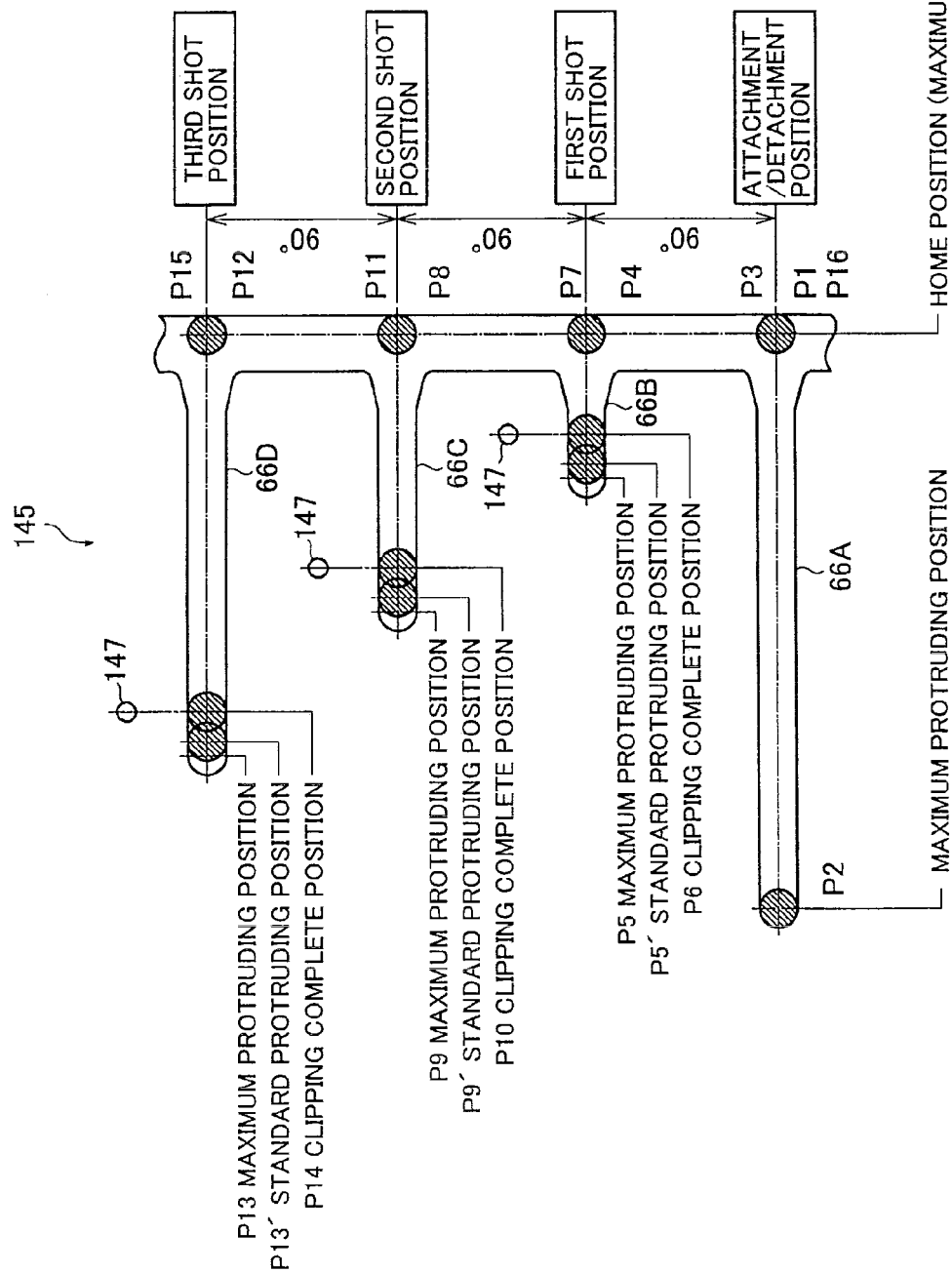
FIG. 19 is a partial developed view of the outer circumferential surface of the slider guide in Embodiment 5.

FIG. 18A is a lateral cross-sectional view illustrating the relationship between a slider 144 and a slider guide 145 in a manipulating handle of Embodiment 5. FIG. 18B is an axial cross-sectional view of FIG. 18A. FIG. 19 is a partial developed view illustrating the positional relationship between the slider guide grooves of the slider guide 145 and the slider pin of the slider 144 during an operation of clipping manipulation, and the positional relationship between the projection of the slider 144 and recesses of the slider guide 145 which are each fit-engaged therewith. The slider 144 and the slider guide 145 have the same configurations as those of the slider 54 and the slider guide 56 in Embodiment 1 except that the slider 144 has a projection 146, and the slider guide 145 has recesses 147 which are each fit-engaged with the projection 146, and hence description is given of the difference therebetween.

Specifically, as illustrated in FIGS. 18A and 18B, the slider 144 is provided with a projection 146 to which a biasing force toward the slider guide 145 is imparted, and which is movable in the direction of the center of the slider 144. The projection 146 of this embodiment is a ball 146a (i.e., a ball plunger) biased by a biasing spring 146b toward the slider guide. The configuration of the projection 146 is not particularly limited, and the projection 146 may be any mechanism having desired resilience, and biased toward the slider guide 145. For example, the projection 146 may also be an engagement claw made of resin, and biased toward the slider guide 145.

On the other hand, as illustrated in FIGS. 18B and 19, the outer circumferential surface of the slider guide 145 has recesses 147 formed at the positions corresponding to positions of the projection 146 when the slider pin 70 has reached clipping complete positions to be each fit-engaged with the projection 146.

Here, the recesses 147 are formed correspondingly to the respective clipping complete positions (P6, P10, and P14) of the individual slider guide grooves (66B to 66D). Therefore, a recess corresponding to the slider guide groove (66A) for loading the clip series 13 to the manipulating wire 20 is not provided.

By thus providing the slider 144 with the projection 146, and forming the slider guide 145 with the recesses 147, the projection 146 of the slider 144 is fit-engaged with one of the recesses 147 of the slider guide 145 when the slider pin 70 reaches the clipping complete position (P6, P10, or P14). The impact produced at this time is transmitted as a sense of clicking to the manipulator.

In this manner, the manipulator can feel that a clipping operation has completed from the sense of clicking, and can feel a sense of manipulation.

Embodiment 6

Figure 20:
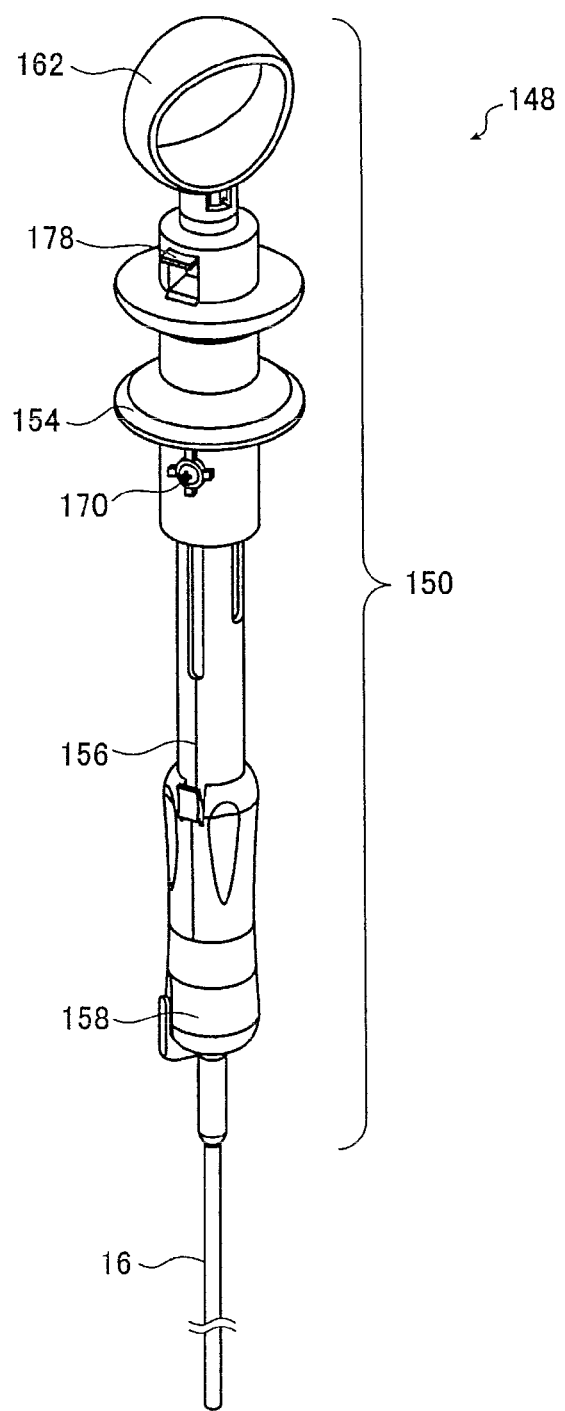
FIG. 20 is a perspective view illustrating a schematic structure of a successive clipping device using a manipulating handle according to Embodiment 6.
Figure 22:
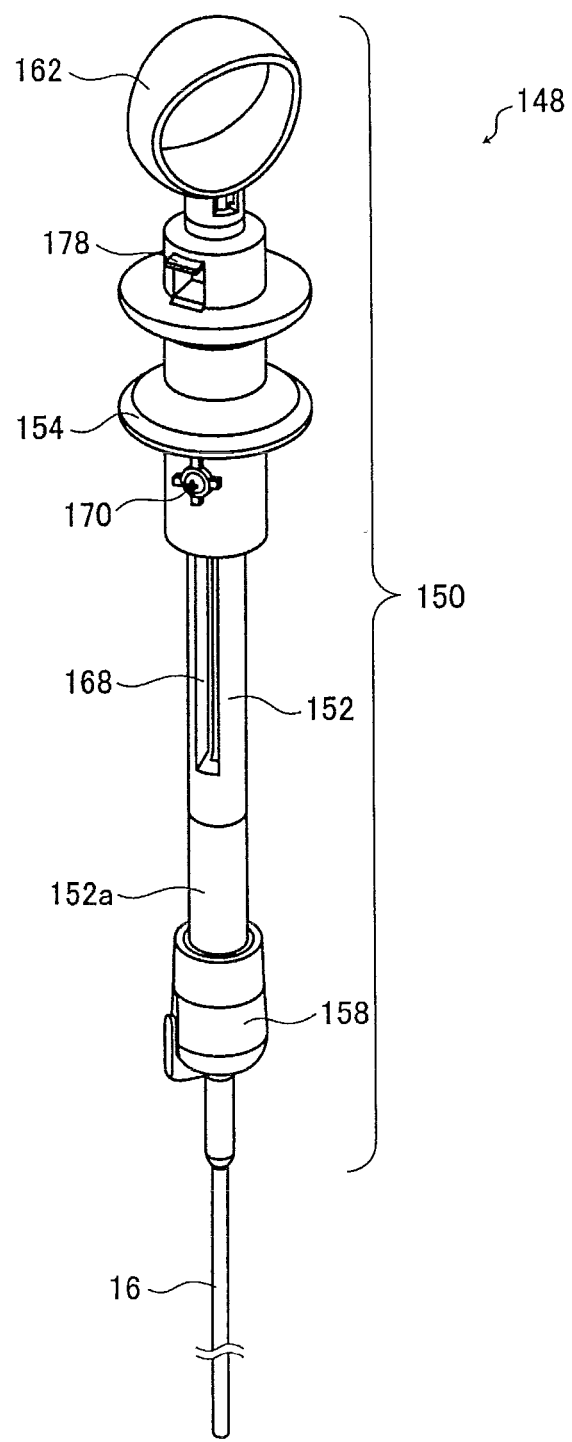
FIG. 22 is a perspective view illustrating a state in which a slider guide has been removed from the manipulating handle illustrated in FIG. 20.

FIG. 20 illustrates a manipulating handle 148 according to Embodiment 6. FIG. 21A is a cross-sectional view diagrammatically illustrating a schematic configuration of a manipulating handle 148. FIG. 21B is a cross-sectional view along the line A-A of FIG. 21A. FIG. 22 is a perspective view illustrating the schematic configuration in a state in which a slider guide 156 has been detached from the manipulating handle 148 illustrated in FIG. 20.

The manipulating handle 148 includes a manipulating portion 150, the sheath 16, the manipulating wire 20, and the hook-shaped connected member (hook) 21 attached to the forward end of the manipulating wire 20. The manipulating portion 150 includes a handle main body 152, a slider 154, the slider guide 156, a position regulating member 158, a biasing spring 160, a finger hook ring 162, and a slider stopper 178.

As illustrated in FIG. 21A, the handle main body 152 is a stepped circular tubular member having three cylindrical portions with different outer circumferential diameters. As illustrated in FIG. 22, a cylindrical portion 152a with an intermediate outer circumferential diameter is provided with a groove 168 extending in the center axis direction. In the handle main body 152, the forward end portion of a cylindrical portion 152b with a small outer circumferential diameter is connected to the proximal end of the sheath 16 and, in the inside thereof, i.e., in the insides of the two cylindrical portions 152a and 152b, the manipulating wire 20 inserted through the sheath 16 has been inserted to extend therethrough. Of the handle main body 152, a portion (proximal end portion) 152c with the largest outer circumferential diameter is located closest to the proximal end of the handle main body 152, and the finger hook ring 162 described later is attached to the portion 152c.

The slider 154 is a cylindrical member arranged around the outer circumference of the handle main body 152 to be movable over the outer circumferential surface of the handle main body 152 in the axial direction thereof, and has a spool-like shape so as to be caught by a manipulator with a hooked finger, and easily moved in the advancing/retreating direction. The slider 154 has a slider pin 170 attached to a part of the inner circumferential surface of the cylindrical member so as to protrude toward the center axis. The slider pin 170 is inserted in the groove 168 to fix the manipulating wire 20 inserted in and through the handle main body 152.

By moving the slider 154 with respect to the handle main body 152 in the axial direction thereof, it is possible to move the manipulating wire 20 fixed to the slider 154 with respect to the sheath 16, and it is possible to move the clip 12 connected to the forward end of the manipulating wire 20 with respect to the sheath 16.

The slider stopper 178 is a member arranged in a recess of the proximal-end-side portion 152c of the handle main body 152, and having a substantially U-shaped cross section. The slider stopper 178 defines the range of movement of the slider 154 on the proximal-end side with a stopper portion 178a at the forward end thereof. The width (width in a direction in FIG. 21A orthogonal to a surface of a paper sheet of FIG. 21A) of the slider stopper 178 may be set appropriately as long as it allows the manipulator to push the slider stopper 178 at the replacement of a slider guide attachment/detachment portion 176 described later, and does not interrupt manipulation during normal clipping manipulation. For example, the slider stopper 178 can have a width substantially equal to that of the groove 168 of the handle main body 152.

In normal use such as during clipping manipulation, the stopper portion 178a of the slider stopper 178 is caused to protrude outwardly of the outer circumference of the proximal end portion 152c of the handle main body 152 by a biasing spring 178b, and the proximal end portion of the slider 154 comes in contact with the stopper 178a, whereby the slider 154 is regulated so as not to move to a position closer to the proximal end of the manipulating portion 150 than the stopper portion 178a.

The slider stopper 178 is pushed at the replacement of the slider guide attachment/detachment portion 176 described later to retract the stopper portion 178a to a position inward of the outer circumference of the proximal end portion 152c, thereby allowing the slider 154 to move to a position closer to the proximal end of the manipulating portion 150 than the stopper portion 178a.

As illustrated in FIG. 21A, the slider guide 156 is integrally formed of a combination of a slider guide base portion 172 and the slider guide attachment/detachment portion 176. The slider guide 156 is a cylindrical member arranged to be circumferentially rotatable over the outer circumferential surface of the handle main body 152 to regulate the amount of movement of the slider 154 in the axial direction of the handle main body 152, and arranged on the outer circumferential surface of the handle main body 152 to be closer to the sheath 16 (the forward end of the sheath 16) than the slider 154. The slider guide base portion 172 includes a forward-end-side projecting joint portion 156a, and a large-diameter portion 156b held by the manipulator for rotating the slider guide 156.

The forward-end-side projecting joint portion 156a of the slider guide 156 is fitted in a rotatable state into a proximal-end-side recessed joint portion 158a of a position regulating member 158 for regulating the position of the slider guide 156 described later, especially the rotational position thereof, and is supported in a rotatable state by the handle main body 152.

The inner diameter of the forward end portion (joint portion 156a) of the slider guide 156 is substantially equal to the outer diameter of the smaller-diameter portion 152b of the handle main body 152 which is inserted therethrough. The proximal-end-side inner diameter of the slider guide 156 is substantially equal to the outer diameter of the larger-diameter portion 152a of the handle main body 152 which is inserted therethrough. The slider guide 156 is supported by the handle main body 152, specifically by the larger-diameter portion 152a and the smaller-diameter portion 152b thereof to be slidable in the circumferential (rotating) direction thereof and in the axial direction thereof. The outer diameter of the proximal-end-side portion of the slider guide 156, i.e., the slider guide attachment/detachment portion 176 is slightly smaller than the inner diameter of the slider 154. Therefore, when the slider 154 moves toward the forward-end side, the slider guide attachment/detachment portion 176 can enter the interior of the slider 154.

The slider guide 156 is manipulated by the manipulator to rotationally move with respect to the position regulating member 158 at the forward end thereof. Thus, the slider guide base portion 172 (portion closer to the proximal end than the joint portion 156a) thereof is provided with the large-diameter portion 156b larger in outer diameter than that of the slider guide attachment/detachment portion 176, and the outer surface of the large-diameter portion 156b is provided with an inclined surface and depressions/protrusions in accordance with a finger, for easy gripping by the manipulator.

As illustrated in FIG. 21A, the slider guide 156 includes the slider guide base portion 172 and the slider guide attachment/detachment portion 176, and the slider guide base portion 172 and the slider guide attachment/detachment portion 176 are detachable. The slider guide base portion 172 is provided with a slider guide engagement portion 174 for engagement with the slider guide attachment/detachment portion 176. The slider guide attachment/detachment portion 176 has been fitted into the slider guide base portion 172. The slider guide base portion 172 is slidable with respect to the handle main body 152 in the circumferential direction and in the axial direction. The slider guide base portion 172 forms the joint portion 156a and the large-diameter portion 156b of the slider guide 156.

The slider guide engagement portion 174 includes a button 174a provided in the slider guide base portion 172, and elastically deformable in the radial direction of the slider guide base portion 172, a claw 174b provided inwardly of the button 174a, and a recess 174c formed in the inner circumferential surface of the slider guide base portion 172 in a position corresponding to the position of the button 174a. The claw 174b is inside the recess 174c, and provided on the inner circumferential side of the button 174a (see FIG. 21B). The slider guide attachment/detachment portion 176 has a projection 176c provided to be engaged with the recess 174c, and elastically deformable in the radial direction of the slider guide attachment/detachment portion 176. By the engagement of the projection 176c with the recess 174c, the slider guide attachment/detachment portion 176 is fixed to the slider guide base portion 172 in the axial direction and the circumferential direction of the handle main body 152. By pressing the button 174a, it is possible to press down the projection 176c of the slider guide attachment/detachment portion 176 with the claw 174b, disengage the projection 176c from the recess 174c, cancel the fit-engagement between the slider guide attachment/detachment portion 176 and the slider guide base portion 172, and detach the slider guide attachment/detachment portion 176 from the slider guide base portion 172.

Similarly to the slider guide 56 of the manipulating handle 48 of Embodiment 1 illustrated in FIGS. 7A and 7B, the slider guide 156 is provided with the four slider guide grooves 66A, 66B, 66C, and 66D extending along the axial direction, and having different lengths.

Similarly to the slider guide 56 and the position regulating member 58 of Embodiment 1, the slider guide 156 and the position regulating member 158 are configured to allow the position of the slider guide 156 in at least one of the rotating direction and the axial direction to be regulated with the tapered shapes and the steps provided in the contact surfaces of the slider guide 156 and the position regulating member 158.

FIG. 23A is a view illustrating the slider guide attachment/detachment portion 176 in detail. The projection 176c is provided in projecting relation at the outer surface of the forward end (on the left side in FIG. 21A) of the slider guide attachment/detachment portion 176.

As illustrated in FIGS. 23B to 23E, the slider guide attachment/detachment portion 176 can be split into halves in the axial direction of the slider guide 156 so as to be detachable from the manipulating portion 150 after the fit-engagement between itself and the slider guide base portion 172 is cancelled. The slider guide attachment/detachment portion 176 includes a split piece 176a and a split piece 176b obtained by halving the slider guide 156 in the axial direction thereof.

The split pieces 176a and 176b are provided with an engagement pin 184 and an engagement hole 186, respectively, for allowing engagement therebetween. By engaging the engagement pin 184 of the split piece 176a with the engagement hole 186 of the split piece 176b, the split pieces 176a and 176b are integrated to configure the cylindrical slider guide attachment/detachment portion 176.

The slider guide attachment/detachment portion 176 is replaceable according to the type of the clip 12. A plurality of types of the slider guide attachment/detachment portions 176 are used according to the types of the clips 12. Therefore, by changing the pitch between the engagement pin 184 and the engagement hole 186 and the positions thereof according to the clip of each size, the combination of the split pieces 176a and 176b of different sizes is prevented to preferably prevent erroneous use thereof.

Next, description is given of the amount of manipulation of the manipulating wire 20 which is needed in clipping manipulation when the types of the clips 12 are different, and the shapes of the slider guide grooves 66A to 66D corresponding thereto.

Figure 24A:
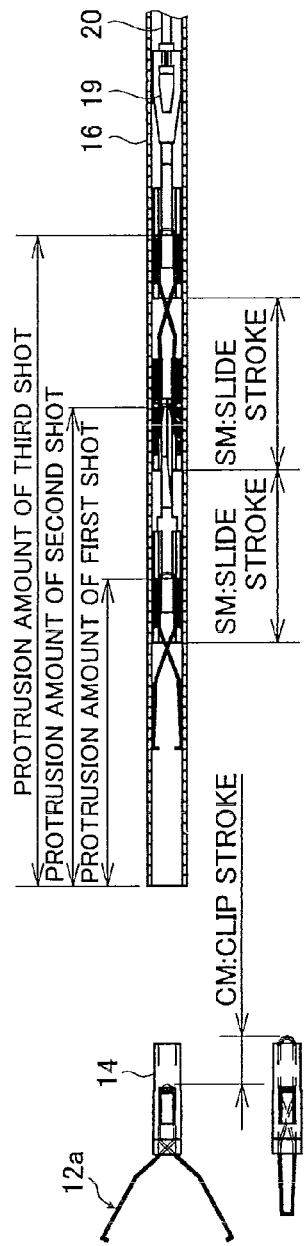
FIGS. 24A to 24C are cross-sectional views illustrating clips of different sizes, and the forward end portions of the clipping device in which the clips are loaded.
Figure 24B:
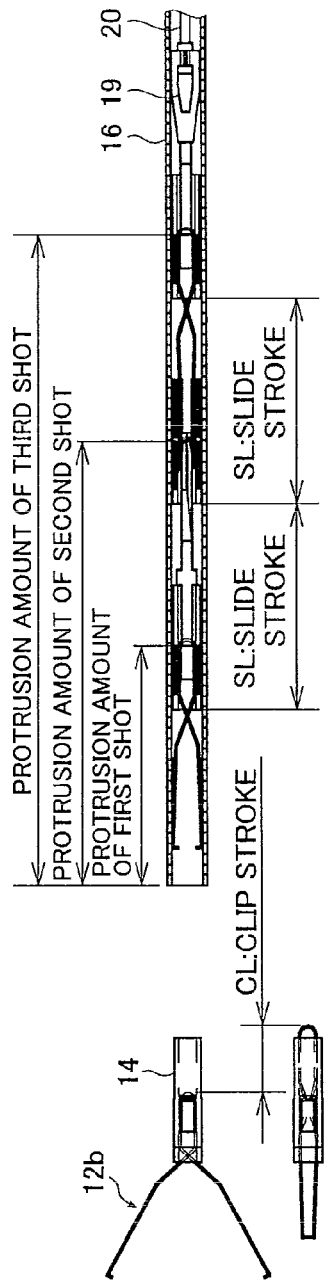
Figure 24C:
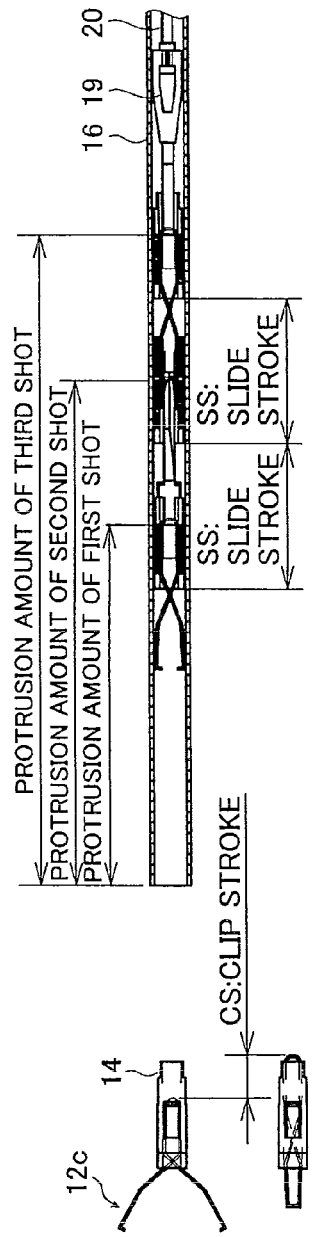

FIGS. 24A to 24C are cross-sectional views of the forward end portion of the sheath 16 illustrating three types of clips of different lengths, and illustrating states when the individual clips are loaded in the sheath 16 of the clipping device 10, of which FIG. 24A illustrates a middle-type clip 12a, FIG. 24B illustrates a long-type clip 12b longer than the middle type, and FIG. 24C illustrates a short-type clip 12c shorter than the middle type.

The individual types of clips 12 (12a, 12b, and 12c) are different in clip strokes CM, CL, and CS, slide strokes SM, SL, and SS, and the amounts of protrusion of the first-shot to third-shot clips 12 illustrated in FIGS. 24A to 24C. Here, a clip stroke is a stroke from a position where the arm portions of the clip 12 are maximally diverged at the forward end portion of the sheath 16 to a position where the arm portions are closed to pinch a target site, and the preceding clip 12 is disconnected from the subsequent clip 12. A slide stroke corresponds to the length of each one of the clips 12, which is the difference between a distance to be covered by the first-shot clip 12 to protrude from the forward end of the sheath 16 (hereinafter referred to as an amount of protrusion of the first shot) and a distance to be covered by the second-shot clip 12 to protrude from the forward end of the sheath 16 (hereinafter referred to as amount of protrusion of the second shot). That is, the amount of protrusion of the second shot is the sum of the amount of protrusion of the first shot and the slide stroke. The amount of protrusion of the clip 12 is the amount of movement of the clip 12 from the position thereof when the slider 154 is at the home position to a position where the clip 12 is in a clipping-manipulation capable state at the forward end portion of the sheath 16.

Compared with the middle-type clip 12a, the long-type clip 12b has a larger entire length and a wider space between the claws when they are diverged, and hence each of the slide stroke and clip stroke thereof is longer. Compared with the middle-type clip 12a, the short-type clip 12c has a smaller entire length and a narrower space between the claws when they are diverged, and hence each of the slide stroke and clip stroke thereof is shorter. Examples of the clip strokes and the slide strokes given herein are CM=4.6 mm, CL=7.8 mm, CS=4.3 mm, SM=13.5 mm, SL=16.5 mm, and SS=11 mm.

Figure 25A:
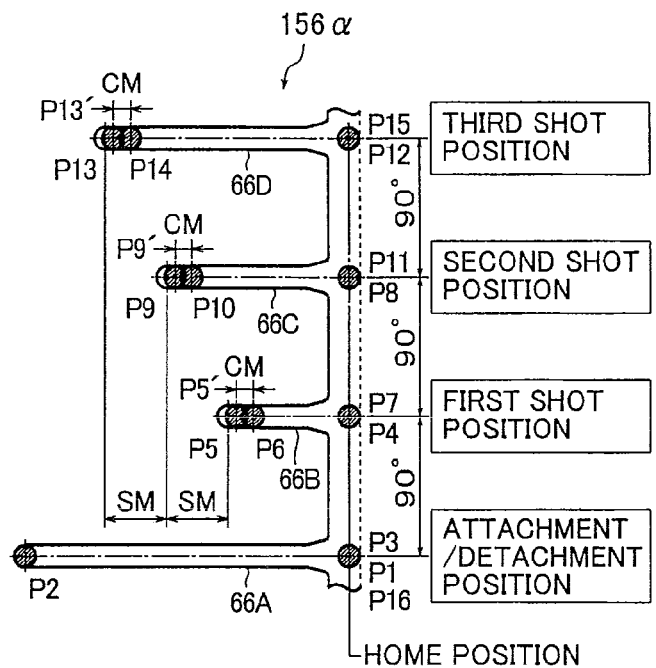
Figure 25B:
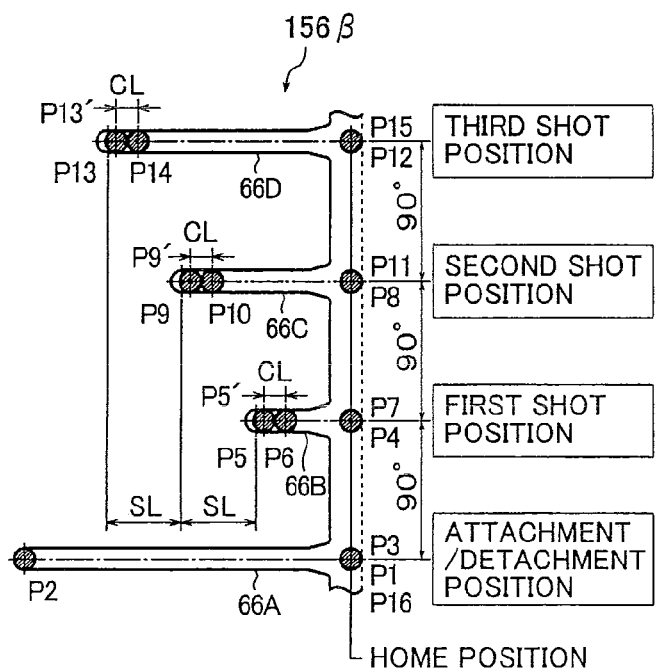

FIGS. 25A to 25C illustrate slider guides 156α, 156β, and 156γ corresponding to the individual types of clips 12a, 12b, and 12c having the slider guide grooves 66B, 66C, and 66D of different lengths. In the drawings, reference symbols illustrating the positions of the slider pin 170, such as P1, are common to those used in Embodiment 1 illustrated in FIG. 9. The slider guide grooves 66A correspond to the attachment/detachment positions of the clips, and therefore the slider guide grooves 66A of the individual types have equal lengths which allow attachment and detachment of a predetermined number of the longest-type clips 12.

The slider guide grooves 66B, 66C, and 66D of the slider guide 156 have lengths corresponding to the individual sizes (middle, long, and short) of the clips 12. When the middle-type clip 12a is used, the middle-type slider guide 156α illustrated in FIG. 25A is used. When the long-type clip 12b is used, the long-type slider guide 156β illustrated in FIG. 25B is used. When the short-type clip 12c is used, the short-type slider guide 156γ illustrated in FIG. 25C is used.

The individual types of slider guide grooves 66B, 66C, and 66D have the lengths corresponding to the respective slide strokes (SM, SL, and SS) and to the respective clip strokes (CM, CL, and CS). Thus, clipping manipulation can be easily performed using the clips 12 of the individual sizes by merely moving the slider 154 along the individual slider guide grooves 66B, 66C, and 66D irrespective of the sizes of the clips 12, i.e., by the same operation irrespective of the sizes of the clips 12.

In addition, the individual types of slider guides 156 (156α, 156β, and 156γ) can be interchanged by changing the slider guide attachment/detachment portion 176 described later, and hence clipping manipulation can be easily performed using the clips 12 of the individual sizes with the single manipulating handle 148.

Next, description is given of a method for changing the slider guide attachment/detachment portion 176 of the slider guide 156.

FIG. 26A is a cross-sectional view of the manipulating handle 148 during use. In this state, the slider guide attachment/detachment portion 176 is inserted in the slider 145, and the slider guide attachment/detachment portion 176 cannot be detached.

First, as illustrated in FIG. 26B, the slider 154 is moved along the axial direction of the handle main body 152 toward the proximal end of the manipulating portion 150 till abutting the stopper portion 178a of the slider stopper 178 (in the direction indicated by the arrow J in the drawing). Here, the forward end portion of the slider 154 is substantially at the same position as that of the proximal end portion of the slider guide attachment/detachment portion 176. This position is the same as the home position during clipping manipulation, i.e., a maximum retracted position during the loading of the clip. It is to be noted that, even in the case where the slider 154 is configured to move further toward the proximal end of the manipulating portion 150 beyond the proximal end portion of the slider guide attachment/detachment portion 176, the slider 154 is retained by the proximal end portion 152c of the handle main body 152, the center of the slider 154 in the axial direction thereof becomes substantially the same as that of the handle main body 152. With this, it is possible to prevent the center of the slider 154 from shifting from that of the handle main body 152, and prevent the slider 154 from being caught by the slider guide attachment/detachment portion 176.

Next, by pressing down the slider stopper 178 in the direction indicated by the arrow K in FIG. 26C, the stopper portion 178a coming in contact with the slider 154 is contained inside the proximal end portion 152c of the handle main body 152 to allow the slider 154 to further move toward the proximal end of the manipulating portion 150 (the direction indicated by the arrow J).

As illustrated in FIG. 26C, the slider 154 is capable of moving till the slider pin 170 comes in contact with the proximal terminal end portion of the groove 168 of the handle main body 152. The distance β between the proximal end portion of the slider guide attachment/detachment portion 176 and the forward end portion of the slider 154 at this time serves as a retreat allowance at the attachment/detachment of the slider guide attachment/detachment portion 176. In addition, the length α of the forward end portion of the slider guide attachment/detachment portion 176 fitted in the slider guide base portion 172 serves as an allowance for the engagement between the slider guide attachment/detachment portion 176 and the slider guide base portion 172. The length α and the distance β satisfy the relationship of α<β.

Next, when the button 174a of the slider guide engagement portion 174 provided in the slider guide base portion 172 is pressed down as illustrated in FIG. 26D, the claw 174b pushes down the projection 176c of the slider guide attachment/detachment portion 176 as illustrated in FIG. 26E, so that the recess 174c of the slider guide engagement portion 174 is disengaged from the projection 176c of the slider guide attachment/detachment portion 176. This allows the slider guide attachment/detachment portion 176 to freely advance and retreat in the axial direction of the manipulating portion 150, and enables, as illustrated in FIG. 26F, the slider guide attachment/detachment portion 176 to move toward the proximal end of the manipulating portion 150 (in the direction indicated by the arrow L in the drawing).

Next, the slider guide attachment/detachment portion 176 is moved toward the proximal end of the manipulating portion 150 till coming into contact with a surface 152d of the proximal end portion 152c of the handle main body 152. This cancels the fit-engagement between the slider guide base portion 172 and the forward end of the slider guide attachment/detachment portion 176 that has been fitted in the slider guide base portion 172. Consequently, as illustrated in FIG. 26G, by being split into the split pieces 176a and 176b, the slider guide attachment/detachment portion 176 can be detached from the handle main body 152.

Next, in order to attach the slider guide attachment/detachment portion 176 corresponding to the size of the clip 12 to be newly used, the split pieces 176a and 176b to be newly used are placed over the handle main body 152, and the engagement pin 184 of the newly used split piece 176a is engaged with the engagement hole 186 of the newly used split piece 176b.

The circumferential position of the handle main body 152 is aligned such that the projection 176c of the slider guide attachment/detachment portion 176 is engaged with the recess 174c of the slider guide engagement portion 174, i.e., the position of the slider guide attachment/detachment portion 176 is aligned such that the projection 176c of the slider guide attachment/detachment portion 176 is on the same line as the button 174a of the slider guide engagement portion 174, and the slider guide attachment/detachment portion 176 is moved toward the forward end portion of the manipulating portion 150 to be fitted into the slider guide base portion 172. As a result, the projection 176c of the slider guide attachment/detachment portion 176 is engaged with the recess 174c of the slider guide engagement portion 174, and the slider guide attachment/detachment portion 176 is fixed to the slider guide base portion 172 in the axial and circumferential directions of the handle main body 152.

Next, when the slider 154 is moved toward the forward end of the handle main body 152, the stopper portion 178a of the slider stopper 178 stored in the proximal end portion 152c of the handle 152 by the slider 154 is caused to partially protrude to the outside of the proximal end portion 152c by the biasing spring 178b. As a result, the proximal-end-side position of the manipulating portion 150 of the slider 154 is defined by the stopper 178a. The position is the home position during clipping manipulation, i.e., the maximum retracted position during the loading of the clip. Afterward, the loading of the clip 12 of the new size corresponding to the newly used slider guide attachment/detachment portion 176, manipulation, and the like become possible.

It is preferable to provide, by using a colored resin, the slider guide attachment/detachment portion 176 with the same color as those of the clip and clip case of each size. The clip case is a case where a new clip is stored. When the manipulator uses the new clip, the new clip is loaded from the clip case into the clipping device 10.

Figure 27A:
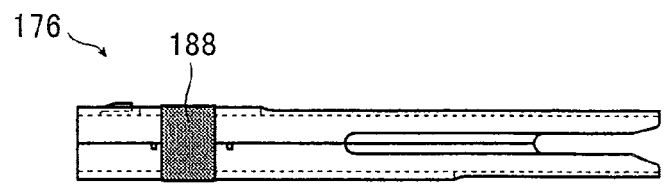
FIGS. 27A and 27B are front views illustrating the slider guide attachment/detachment portions provided with respective marked portions.

It is also preferable not to change the color of the entire slider guide attachment/detachment portion 176, but to provide a marked portion 188 in the slider guide attachment/detachment portion 176, as illustrated in FIG. 27A. The marked portion 188 is provided in the slider guide attachment/detachment portion 176 by labeling or printing. For example, it is possible to provide the marked portion 188 with the same color as those of the clip 12 of each size and the clip case thereof. The same slider guide attachment/detachment portion 176 can be used for those of the clips 12 of each size which have the same clip size (same arm length), but are different in the angle of the forward end of the claw thereof. Thus, it is also preferable that the marked portion 188 be represented by a plurality of colors, such as colors showing the angles of the forward ends of the claws. The marked portion 188 may also be represented not only by color, but also by a letter, a symbol, a barcode, a two-dimensional code, or the like.

Here, an example of the color correspondence between the slider guide attachment/detachment portion 176 and the clip case storing therein the clip 12 is shown in TABLE 1.

TABLE 1

| | Clip size (arm length) | | |
|---|---|---|---|
| | Long | Middle | Short |
| Color of clip case | Blue | Yellow | White (Transparent) |
| Color of slider guide attachment/detachment portion or color of marked portion | Blue | Yellow | White |

In the example of TABLE 1, the clip case and slider guide attachment/detachment portion 176 of the long-size clip 12 are each colored in blue, the clip case and slider guide attachment/detachment portion 176 of the middle-size clip 12 are each colored in yellow, and the clip case and slider guide attachment/detachment portion 176 of the short-size clip 12 are each colored in white or made transparent. Besides changing the color of the entire slider guide attachment/detachment portion 176, the color of the marked portion 188 may be changed (see FIG. 27A).

In this manner, it is possible to easily recognize the slider guide attachment/detachment portion 176 and the clip case, and prevent the misrecognition of the type of the clip 12 to be used. For example, when the long-type clip 12 is used, the clip size can be easily recognized by using the blue slider guide attachment/detachment portion 176 or the slider guide attachment/detachment portion 176 having the blue marked portion 188, and the blue clip case.

Another example of the color correspondence between the slider guide attachment/detachment portion 176 and the clip case storing the clip 12 therein is shown in TABLE 2.

TABLE 2

| | Clip size (arm length) | | | | |
|---|---|---|---|---|---|
| | Long | Middle | | Short | |
| Angle of forward end of claw | 90° | 90° | 135° | 90° | 135° |
| Color of clip case | Blue | Yellow | Pink | White (Transparent) | Green |
| Color of marked portion | Blue | Yellow | Pink | White | Green |

Figure 27B:
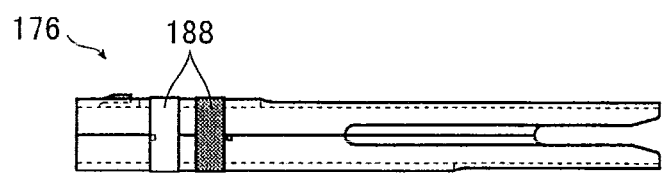

The example of TABLE 2 shows, in addition to the example of TABLE 1, the case where the forward end of the claw of the clip 12 has two angles. For the forward end of the claw of each of the middle-size clip 12 and the short-size clip 12, the two angles of 90° and 130° are prepared. When the angle of the forward end of the claw of the middle size clip is 135°, the clip case and the marked portion of the slider guide attachment/detachment portion 176 thereof are each colored in pink. When the angle of the forward end of the claw of the short size clip is 135°, the clip case and the marked portion of the slider guide attachment/detachment portion 176 thereof are each colored in green. The slider guide attachment/detachment portion 176 need not be selectively used according to the different angles of the forward end of the claw. For each of the middle-size clips 12 in which the respective angles of the forward ends of the claws are 90° and 130°, the same slider guide attachment/detachment portion 176 can be used. Therefore, as illustrated in FIG. 27B, by providing the slider guide attachment/detachment portion 176 with the two marked portions 188, and representing the two marked portions 188 in yellow and pink, it can be recognized that each one of the clips 12 is usable irrespective of the angle of the forward end of the claw.

In the case with the short-size clips also, it can be recognized that each one of the clips 12 can be used irrespective of the angle of the forward end of the claw by representing the two marked portions 188 in white (or transparent and green), similarly to the case with the middle-size clips. In the example of TABLE 2, the forward ends of the claws of the long-type clips 12 have one angle of 90°. Therefore, the long-type clips 12 may be represented in blue by the marked portions 188 thereof similarly to the clips 12 of the other sizes, or the slider guide attachment/detachment portions 176 thereof may be entirely colored in blue.

Embodiment 7

Figure 28:
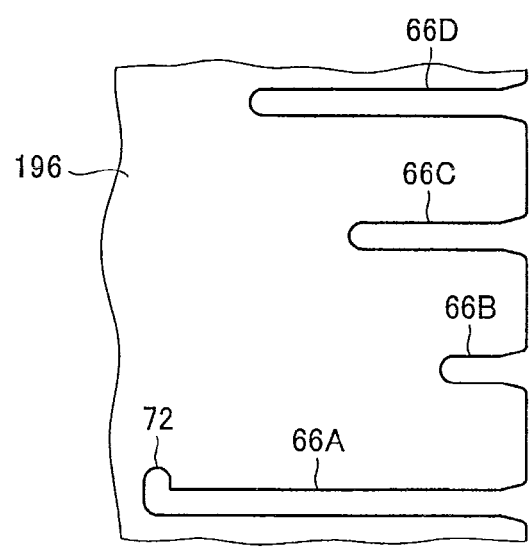
FIG. 28 is a partial developed view of the outer circumferential surface of a slider guide used in Embodiment 7.

In the manipulating handle of Embodiment 1, a slider guide 196 having a groove shape as illustrated in FIG. 28 may also be used instead of the slider guide 56. The slider guide 196 is formed not only with the four slider guide grooves 66A, 66B, 66C, and 66D of different lengths, similarly to the slider guide 56 of Embodiment 1, but also with a position fixing groove 72 connected to the slider guide groove 66A.

The position fixing groove 72 and the slider pin 70 constitutes a wire position fixing mechanism.

The position fixing groove 72 is connected to the forward end portion of the slider guide groove 66A closer to the sheath 16 to extend in the circumferential direction of the slider guide 196 by a predetermined distance, and has a width which allows fit-engagement with the slider pin 70.

In a state in which the slider pin 70 has been moved by the slider 54 to the forward end portion of the slider guide groove 66A closer to the sheath 16, the slider guide 196 is further rotated, whereby the slider pin 70 is fit-engaged with the position fixing groove 72.

By thus engaging or fit-engaging the slider pin 70 with the position fixing groove 72, the slider 54 and the slider pin 70 are fixed to predetermined positions in the axial direction of the manipulating handle. That is, the slider 54 and the slider pin 70 are inhibited from moving along the slider guide groove 66A, and the manipulating wire 20 is temporarily fixed in a state of protruding from the sheath 16 by a given length.

Description is given here of a method of loading the clip series in the clipping device and of devices used therefor.

Figure 29:
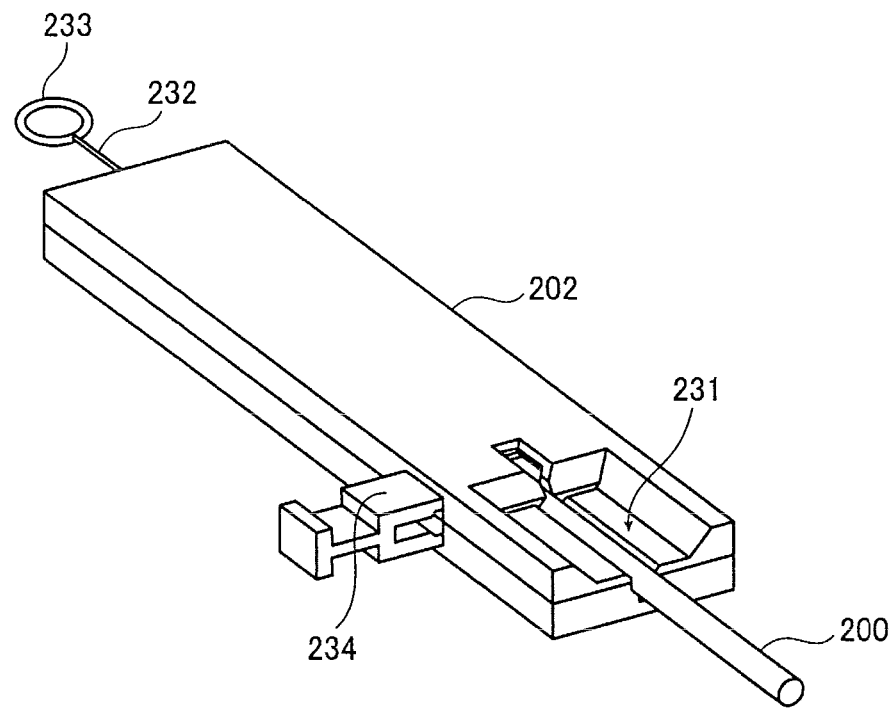
FIG. 29 is a perspective view illustrating a clip case and an attachment jig each used in Embodiment 7.
Figure 30:
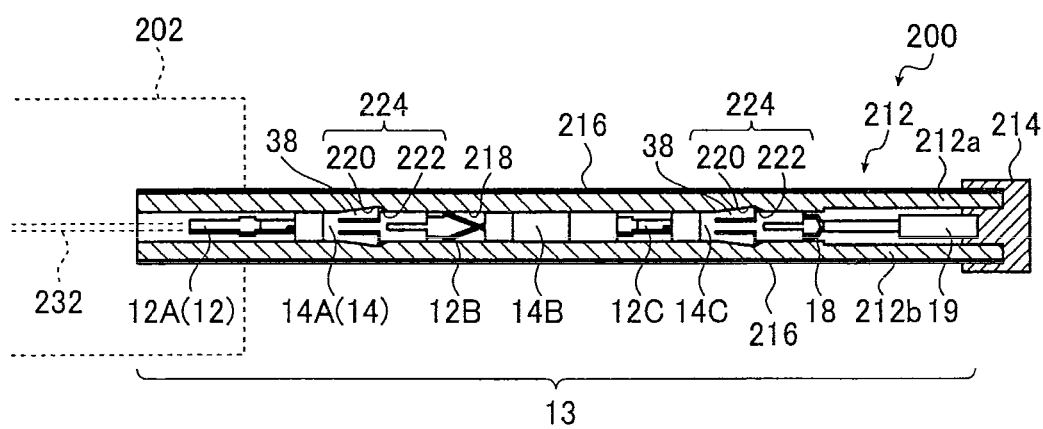
FIG. 30 is a cross-sectional view illustrating the clip case.
Figure 31A:
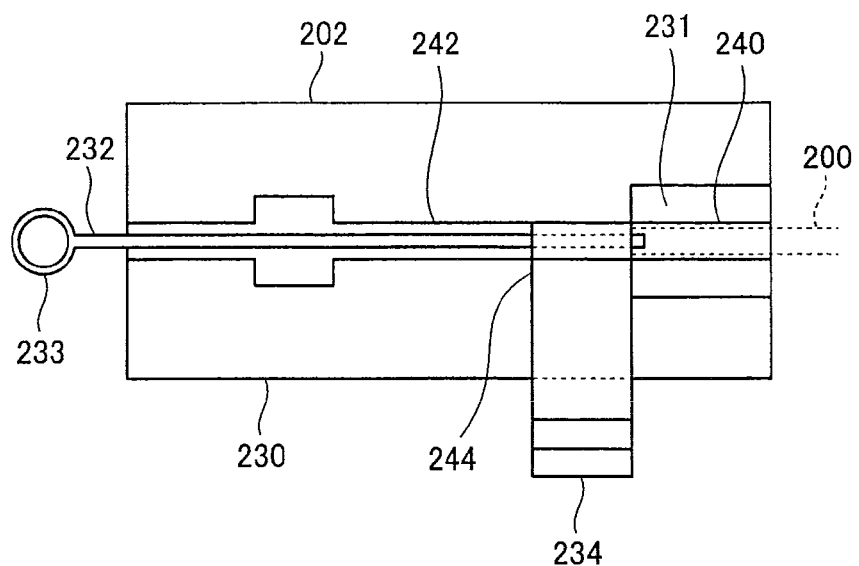
FIG. 31A is a plan view illustrating the attachment jig.
Figure 31B:
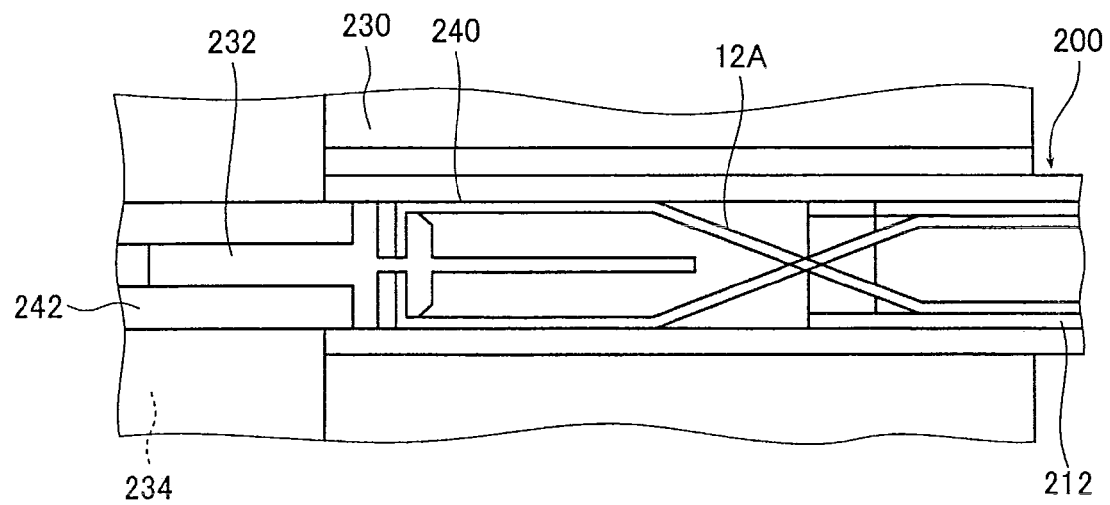
FIG. 31B is an enlarged cross-sectional view illustrating a part of the clip case in the attachment jig.

FIG. 29 is a perspective view illustrating the clip case and an attachment jig for mounting the clip series in the clipping device according to Embodiment 7. FIG. 30 is a cross-sectional view illustrating the clip case. FIG. 31A is a plan view illustrating the attachment jig. FIG. 31B is an enlarged cross-sectional view illustrating a part of the clip case in the attachment jig.

A clip case 200 illustrated in FIG. 29 retains the clip series 13 including the three clips 12A to 12C in the interior thereof. When the clip series is attached to the manipulating wire 20 of the clipping device 10 to be connected thereto, and loaded in the sheath 16 thereof, the attachment jig 202 receives the clip series 13 retained in the clip case 200 therefrom, closes the skirt portions 38 of the connection rings 14, and temporarily retains the skirt portions 38 in a closed state.

The clip case 200 and the attachment jig 200 are in a connected state during distribution and during storage (i.e., till the clip series 13 is loaded in the clipping device 10).

As illustrated in FIG. 30, the clip case (hereinafter simply referred to as "case") 200 is for the distribution and storage of the clip series 13 to be loaded in the clipping device 10, and has a case main body 212, and a cap 214.

The case main body 212 has a cylindrical shape, and accommodates therein the clip series 13 including the plurality of bleeding stop clip members composed of the clips 12 (12A to 12C), and the connection rings 14 (14A to 14C). As illustrated in FIGS. 29 and 30, the case main body 212 is formed of a combination of two semicylindrical case components 212a and 212b having substantially the same shape. The forward ends of the two case components 212a and 212b have been fitted in the attachment jig 202, and the rear ends thereof have been fitted in the cap 214 to maintain the case main body 212 in the closed state.

Preferably, the case main body 212 is transparent or semi-transparent to allow the interior thereof to be visible. In terms of impact resistance, ease of handling, and ease of molding, the case main body 212 is preferably formed of a resin which does not denature at an ambient temperature, i.e., at a temperature in a use environment, in a variation range (e.g., 5° C. to 70° C.) of a sterilization temperature in a sterilization step, by ethylene oxide gas (EOG) sterilization, by low-temperature plasma sterilization, or by γ-ray sterilization. In this embodiment, the case main body 212 has the cylindrical shape, but the outer shape of the case main body 212 is not limited to a cylinder, and may also be a rectangular column.

In order to accommodate therein the medical clips 12, it is necessary for the case 200 to keep the interior of the case main body 212 air-tight. Therefore, in the case main body 212, the outer surfaces of the case components 212a and 212b are covered with a cover 216 made of a transparent resin to ensure air tightness of the interior of the case main body 212. Alternatively, the case components 212a and 212b of the case main body 212 may be formed of an elastic material, and retained by the cap 214 and the attachment jig 202 described later with the contact surfaces thereof being pressed against each other to ensure air-tightness. Otherwise, a packing material may be provided between the case components 212a and 212b to ensure air-tightness.

The cap 214 may be any member as long as the member seals the case components 212a and 212b in an air-tight state, and may be made of rubber or resin. The cap 214 is detachable. When the clip series 13 inside the case main body 212 is loaded into the sheath, the clip series 13 in the interior thereof is temporarily pulled out by the attachment jig 202, while remaining in the connection state (see FIG. 31A).

As illustrated in FIG. 30, in the case main body 212, a hole having an inner diameter slightly larger than the outer diameter of the connection ring 14, and substantially equal to the inner diameter of the sheath 16 into which the clip series 13 is loaded is formed through the entire case main body 212. The hole accommodates therein the clip series 13 including the three connected clips 12A to 12C, the dummy clip 18, the three connection rings 14A to 14C covering the connection portions therebetween, and the connecting member 19 connected to the rear end of the dummy clip 18. The forward end of the foremost clip 12A is protected by the attachment jig 202. The connecting member 19 at the rear end of the dummy clip 18 connected to the rearmost clip 12C is retained by the cap 214.

Further, to the forward end of the foremost clip 12A, a pull rod 232 of the attachment jig 202 is connected.

Additionally, as illustrated in FIG. 30, recesses 224 having shapes corresponding to the shapes of the skirt portions 38 are provided in the inner surface of the case main body 212 (case components 212a and 212b) and at the positions where the connection rings 14A to 14E are accommodated. The recesses 224 are each formed of a first oblique portion 220 which radially and outwardly diverges from a straight portion 218 in substantially conformal relation to the divergence of the skirt portions 38 at substantially the same angle as that of the inclination of the skirt portions 38 in the natural state, and a second oblique portion 222 radially tapers from the diverged end (rear end) portion of the first oblique portion 220.

As described above, the clips 12A to 12C are connected, while changing the orientations thereof by 90° at a time. Correspondingly, the connection rings 14A to 14C are also fitted in the clips 12A to 12C, while changing the orientations thereof by 90° at a time from those of the preceding and subsequent connection rings 14. Therefore, the positions of the recesses 224 in the case main body 212 are also circumferentially shifted by 90° at a time correspondingly to the respective connection rings 14A to 14C.

Accordingly, in FIG. 30, the recesses 224 having shapes corresponding to the skirt portions 38 of the connection rings 14A and 14C are illustrated at upper two portions and lower two positions. The recesses 224 having shapes corresponding to the skirt portions 38 of the connection ring 14B are not shown, but are formed at two positions in a direction perpendicular to a surface of a paper sheet of FIG. 30. The recesses 224 may also be formed in the inner surface of the case main body 212 and at positions corresponding to the respective skirt portions 38 of the individual connection rings 14 around the entire circumference.

By the first oblique portions 220 of the recesses 224, the connection rings 14A to 14C are accommodated in the case main body 212, with the skirt portions 38 being diverged without receiving an external force. As a result, it is possible to prevent degradation of the elasticity of the skirt portions 38 while the skirt portions 38 are stored in the case main body 212, and maintain the performance of the connection rings 14A to 14C.

The second oblique portions each inclined at a predetermined angle are provided between the rear-end-side surfaces of the first oblique portions 220 and the straight portions 218, but the present invention is not limited thereto. Surfaces extending along the skirt portions 38 in a diverged state, and perpendicular to the straight portions 218 may also be provided between the rear-end-side surfaces of the first oblique portions 220 and the straight portions 218.

As illustrated in FIG. 31A, the attachment jig 202 includes a jig main body 230, the pull rod 232, and an opening diameter varying member 234.

The jig main body 230 has a rectangular parallelpiped shape whose longitudinal direction corresponds to the extending direction of the case 200, and is engaged with the forward end portion of the case 200. The jig main body 230 also includes a recess 231 formed on its proximal-end side, an engagement groove 240 formed in the recess 231, and engaged with the forward ends of the case 200 and the sheath 16 inserted therein, a guide path 242 shaped as a circular hole, and formed extensively on the extension line of the engagement groove 240, and a hollow portion 244 opened in the side surface of the jig main body 230, and formed between the engagement groove 240 and the guide path 242 to support the opening diameter varying member 234 slidably in a direction orthogonal to the guide path 242. In this embodiment, the jig main body 230 has the rectangular parallelpiped shape, but the shape of the jig main body 230 is not limited to a rectangular parallelpiped, and may be any. The shape of the jig main body 230 may also be a column, a rectangular column, a cylinder, a semi-cylinder, a pyramid, or the like.

The engagement groove 240 has an inner diameter slightly larger than the outer diameters of the case 200 and the sheath 16. At first, the case 200 is fitted in the engagement groove 240, and then pulled away therefrom so that the sheath 16 is fitted therein instead. The engagement groove 240 is formed in the recess 231 of the attachment jig 202 along the longitudinal direction thereof. The upper portion of the engagement groove 240 is opened.

The guide path 242 is a circular hole for closing the skirt portion 38 of the connection ring 14 opened in the case 200, which is formed on the extension line of the engagement groove 240 to extend through the interior of the jig main body 230. One end portion of the guide path 242 opposes the engagement groove 240 with the hollow portion 244 interposed therebetween, while the other end portion thereof serves as an opening formed in the end surface of the jig main body 230. The guide path 242 basically has a shape having the same inner diameter as that of the straight portion 218 of the case main body 212 and a portion adjacent to the end portion on the opposite side of the engagement groove 240 which is larger in diameter than the other portion. The guide path 242 may also include a tubular path or the like.

The hollow portion 244 is a rectangular parallelpiped space provided between the engagement groove 240 and the guide path 242 in orthogonal relation to the guide path 242, and having a longitudinal direction thereof corresponding to a direction parallel with a plane in which the engagement groove 240 is opened.

The opening diameter varying member 234 is fit-engaged with the hollow portion 244, and supported thereby.

The pull rod 232 is a rod-shaped member inserted through the engagement groove 240. As illustrated in FIG. 31B, one end portion of the pull rod 232 is engaged with the forward end of the clip 12A, and the other end portion thereof is provided with a finger hook ring 233 so as to be capable of being pulled by the user.

The opening diameter varying member 234 is a member fit-engaged with the hollow portion 244 to be movable in a direction orthogonal to the guide path 242, and having a two-forked forward end. Both the opposing surfaces of the two-forked portion are provided with respective recesses (not shown) having substantially the same inner diameters as the outer diameters of the case 200 and the sheath 16.

The opening diameter varying member 234 has the function of being pushed into the hollow portion 244 to be fit-engaged therewith, and thereby pushing the connected member 21 at the forward end of the manipulating wire 20 to a position where the connected member 21 is inserted into the guide path 242, and the function of causing the case 200 and the sheath 16 to be alternately caught in the recess of the two-forked portion described above.

Hereinbelow, description is given of a method of loading the clip series retained in the clip case into the sheath of the clipping device.

Figure 32:
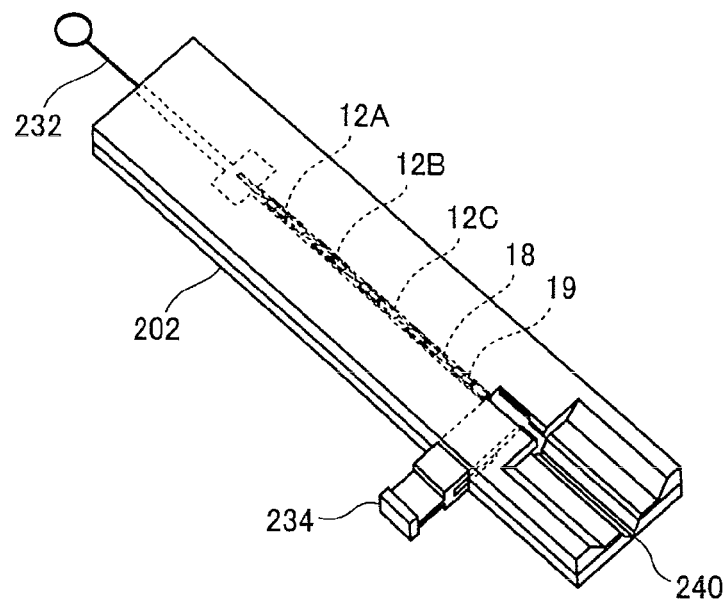
FIG. 32 is a perspective view of the attachment jig in a state in which a clip series has been moved in the interior thereof.
Figure 33:
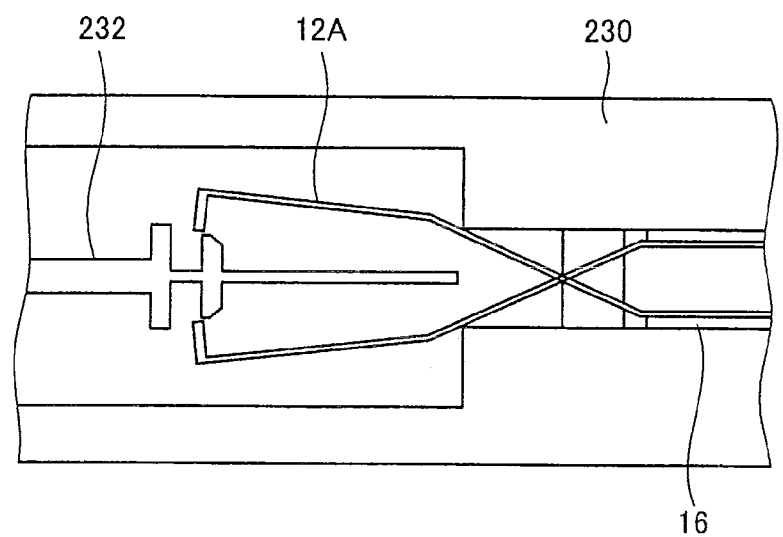
FIG. 33 is a plan view illustrating the relationship between the clip and a pull bar in the attachment jig.
Figure 34A:
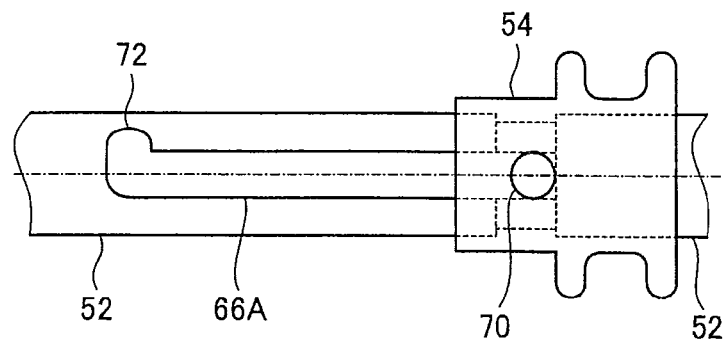
FIGS. 34A to 34C are plan views illustrating the states in respective steps of the manipulating handle of Embodiment 7 in individual steps.
Figure 34B:
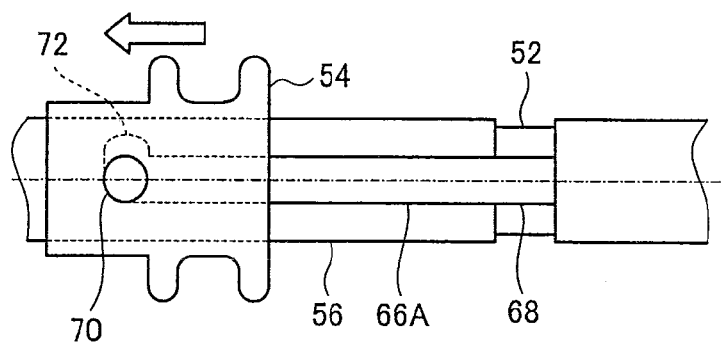
Figure 34C:
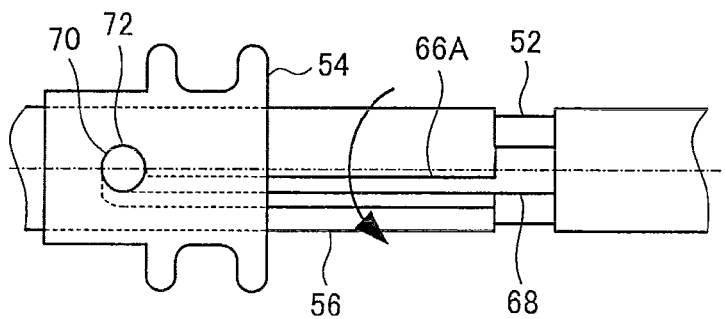
Figure 35A:
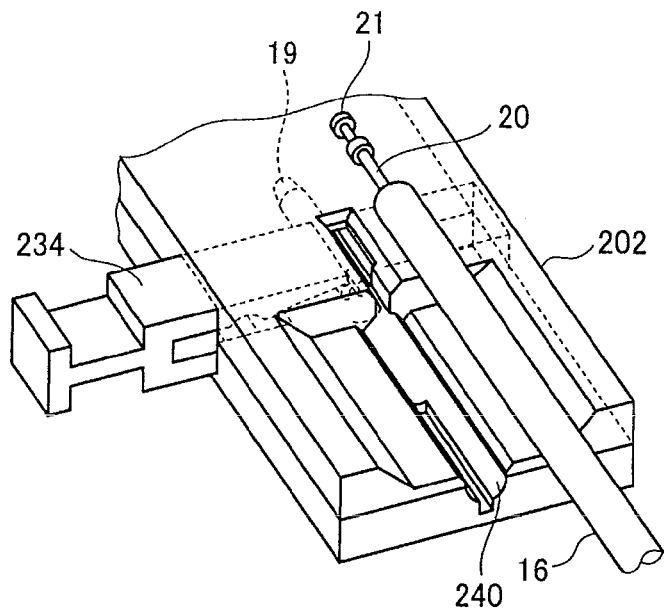
FIGS. 35A and 35B are perspective views each illustrating the relationship between a clipping device and the attachment jig.
Figure 35B:
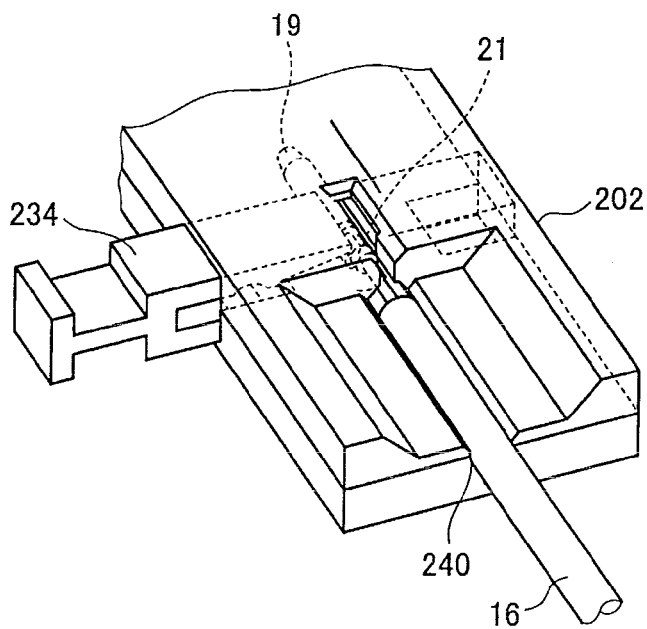

FIG. 32 is a perspective view illustrating a state in which the clip series in the clip case illustrated in FIG. 30 has been moved in the interior thereof. FIG. 33 is a plan view illustrating the relationship between the clip and the pull rod in the attachment jig illustrated in FIG. 29. FIGS. 34A to 34C are plan views illustrating the respective states of the manipulating handle in individual steps. FIGS. 35A and 35B are perspective views each illustrating the relationship between the attachment jig 202 and the clipping device 10.

At first, during storage, the case 200 retaining the clip series 13 therein, and the attachment jig 202 are in a connection state.

In this state, the pull rod 232 of the attachment jig 202 is pulled to withdraw the finger hook away from the jig main body 230.

By pulling the pull rod 232, the clip series 13 engaged with the pull rod 232 is pulled toward the attachment jig 202 to be brought into a state in which the clip series 13 is retained in the inside of the guide path 242, as illustrated in FIG. 32. By causing the clip series 13 to be retained in the guide path 242 having the same diameter as that of the straight portion 218 of the case main body 218, the skirt portions 38 are closed.

As illustrated in FIG. 32, when the end portion engaged with the clip 12A reaches the region of the guide path 242 which is larger in diameter than the other portion thereof, the forward end of the clip 12A opens to allow the pull rod 232 to be detachable from the clip 12A, as illustrated in FIG. 33.

At this time, the connecting member 19 of the rearmost dummy clip 18 of the clip series 13 is partially placed on the opening diameter varying member 234.

On the other hand, as illustrated in FIG. 34A, the clipping device 10 rotates the slider guide 56 such that the slider guide groove 66A overlaps the engagement groove 68 of the handle main body 52, and adjusts the orientation of the slider guide 56. At this time, the slider pin 70 is retained at the end portion (hereinafter referred to as "home position") of the movable region of the slider pin 70 (and of the slider 54) closer to the finger hook ring 62.

Next, as illustrated in FIG. 34B, the slider 54 and the slider pin 70 are moved to the end portion of the slider guide groove 66A closer to the sheath 16. By thus moving the slider 54 and the slider pin 70 to the end portion of the slider guide groove 66A closer to the sheath 16, the manipulating wire 20 is brought into a state of protruding from the forward end of the sheath 16 by a predetermined distance.

Next, the slider guide 54 is rotated to fit-engage the slider pin 70 with the position fixing groove 72. By thus fit-engaging the slider pin 70 with the position fixing groove 72, the slider pin and the slider guide 54 are brought into a state in which they cannot move along the slider guide groove 66A, and hence the manipulating wire 20 is temporarily fixed in the state of protruding from the forward end of the sheath 16 by the predetermined distance.

Next, the connected member 21 of the manipulating wire 20 protruding from the forward end of the sheath 16 by the predetermined distance is connected to the connecting member 19 of the rearmost dummy clip 18 of the clip series retained by the attachment jig 202.

Specifically, as illustrated in FIG. 35A, the forward end of the sheath 16 is moved onto the opening diameter varying member 234.

Then, the sheath 16 is fit-engaged with the engagement groove 240 to cause the connected member 21 of the manipulating wire 20 protruding from the forward end of the sheath 16 by the predetermined distance to overlap the connecting member 19 of the dummy clip 18 placed on the opening diameter varying member 234.

Next, the opening diameter varying member 234 is moved to align the opening having the same diameter as that of the guide path 242 and the guide path 242 on the same straight line. At this time, the part of the two-forked portion of the opening diameter varying member 234, where the two forks have a smaller distance therebetween, passes through the portion where the connected member 21 overlaps the connecting member 19, and the connected member 21 is pushed into the connecting member 19 to result in a mutually meshing state.

Then, the slider guide 54 is rotated in a direction in which the slider guide groove 66A is engaged with the slider pin 70. After that, by moving the slider 54 toward the home position, the clip series in the attachment jig 202 is pulled by the manipulating wire 20 to enter a state in which it is loaded inside the sheath 16.

Thus, with the clipping device 10, it is possible to fix the manipulating wire 20 in the state of protruding from the sheath 16 by the predetermined distance when the connecting member 19 of the dummy clip 18 is connected to the connected member 21 of the manipulating wire 20. This allows easy connection between the connecting member 19 and the connected member 21. In particular, when the connecting member 19 and the connected member 21 are connected in a direction other than extending directions of the manipulating wire 20 and the clips 12, it is possible to maintain a uniform amount of protrusion of the manipulating wire 20, to thereby increase manipulating properties.

Further, it is possible to maintain the uniform amount of protrusion of the manipulating wire 20, and hence the occurrence of a faulty operation such that the connecting member 19 and the connected member 21 cannot be connected due to a small amount of protrusion of the manipulating wire 20 can be prevented. It is also possible to prevent a failure such as the deformation of the manipulating wire caused by a load placed on the manipulating wire.

Embodiment 8

In Embodiment 7 described above, the slider pin 70 and the position fixing groove 72 are configured to be fit-engaged as the position fixing mechanism. However, the present invention is not limited thereto. The same effect is also obtainable by providing a recess in one of the two members of the slider and the slider guide, and providing a projection in the other member as the position fixing mechanism. In this case, it is necessary to provide the recess and the projection at the positions where the slider is fixed (i.e., the position where the amount of protrusion of the manipulating wire is fixed), and where the recess is fit-engaged with the projection. It is also necessary to fit-engage the recess and the projection in detachable relation.

Figure 36A:
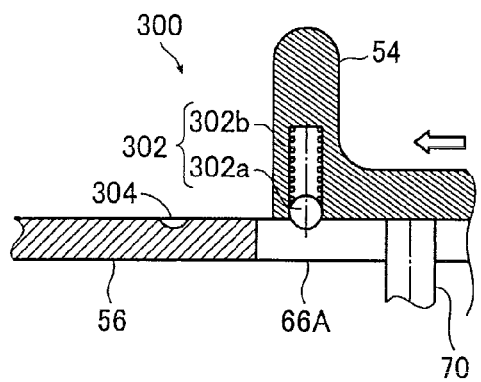
FIGS. 36A and 36B are partial cross-sectional views each illustrating a position fixing mechanism used in Embodiment 8.
Figure 36B:
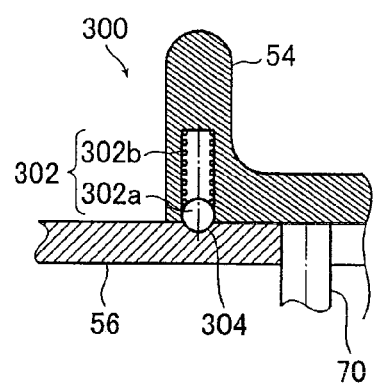

FIGS. 36A and 36B illustrate a position fixing mechanism 300 used in Embodiment 8. FIG. 36A illustrates the slider 54 in a movable state. FIG. 36B illustrates the slider 54 whose position has been fixed. The position fixing mechanism 300 has a projection 302 provided at the inner circumferential surface of the slider 54, and a recess 304 formed in the outer circumferential surface of the slider guide 56.

The projection 302 is a member to which a biasing force toward the slider guide 56 is imparted, and which is movable in a direction in which it comes in contact with and separates from the slider guide 56. Specifically, the projection 302 is a ball 302a (i.e., a ball plunger) biased by a biasing spring 302b toward the slider guide 56. The projection 302 is provided at the same position as that of the slider pin 70 in the circumferential direction to be closer to the sheath 16 than the slider pin 70 of the slider 54 in the moving direction of the slider pin 70.

The recess 304 is formed to be closer to the sheath by a predetermined distance than the end portion of the slider guide groove 66A in the outer circumferential surface of the slider guide 54 closer to the sheath 16.

As illustrated in FIG. 36B, the recess 304 and the projection 302 are provided to have a positional relationship therebetween such that they are fit-engaged with each other when the slider pin 70 comes in contact with the sheath-side end portion of the slider guide groove 66A (i.e., when the slider pin 70 is moved to the maximum protruding position).

By configuring the position fixing mechanism 300 as described above, it is possible to temporarily fix the manipulating wire 20 (and the slider 54) in the state in which the manipulating wire 20 is protruding from the sheath 16 by the predetermined distance.

Figure 37A:
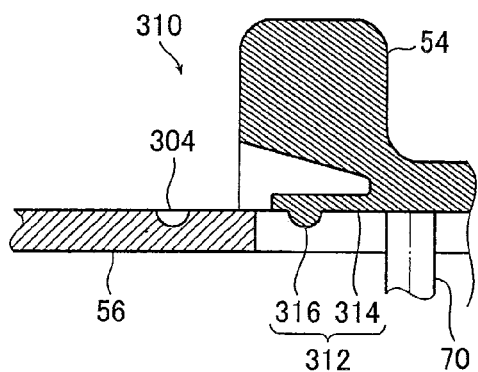
FIGS. 37A and 37B are partial cross-sectional views each illustrating a position fixing mechanism used in a modification of Embodiment 8.
Figure 37B:
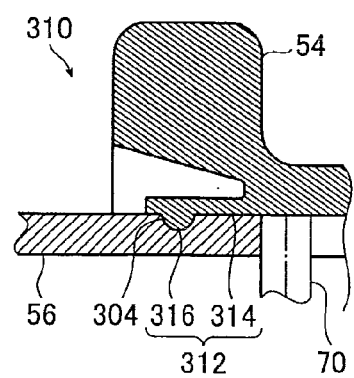

In the position fixing mechanism 300, the projection 302 is configured by the ball plunger. However, as in a position fixing mechanism 310 illustrated in FIGS. 37A and 37B, a projection 312 may also be an engagement claw, which is made of resin, and has a cantilever 314 biased toward the slider guide 56, and a protrusion 316 to be fit-engaged with a recess 304 in the surface of the cantilever 314 in contact with the slider guide 56. In this case, it is necessary to provide the handle main body 52 with a space for allowing the cantilever 314 to be movable. FIG. 37A illustrates the slider 54 in a movable state. FIG. 37B illustrates the slider 54 whose position has been fixed.

Thus, even though the engagement claw is used, when, as illustrated in FIG. 37B, the slider pin 70 is moved to the position where it comes in contact with the end portion of the slider guide groove 66A closer to the sheath 16, the projection 312 and the recess 304 are fit-engaged to fix the slider 54 at a predetermined position. Thus, with the position fixing mechanism 310 also, the manipulating wire 20 can be temporarily fixed in the state of protruding from the sheath 16 by the predetermined distance.

In each of the position fixing mechanisms 300 and 310 described above, the projection 302 or 312 is provided in the slider 54, and the recess 304 is provided in the slider guide 56. However, the recess and the projection may also be provided in reversed relation.

Figure 38A:
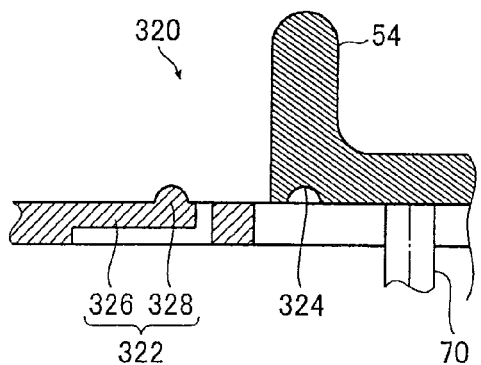
FIGS. 38A and 38B are partial cross-sectional views each illustrating a position fixing mechanism used in another modification of Embodiment 8.
Figure 38B:
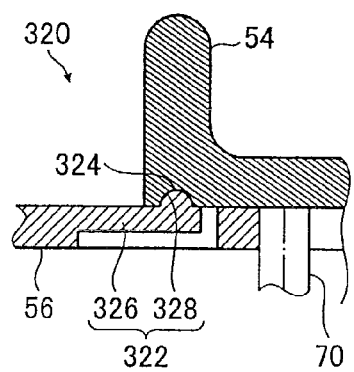

A position fixing mechanism 320 illustrated in FIGS. 38A and 38B includes a projection 322 provided at the outer circumferential surface of the slider guide 56, and a recess 324 provided in the inner circumferential surface of the slider 54. FIG. 38A illustrates the slider 54 in a movable state, and FIG. 38B illustrates the slider 54 whose position has been fixed.

The projection 322 is formed to be closer to the sheath 16 by a predetermined distance than the end portion of the slider guide groove 66A closer to the sheath 16. The projection 322 is a member to which a biasing force toward the slider 54 is imparted, and which is movable in a direction in which it comes in contact with and separates from the slider guide 56. Specifically, the projection 322 is an engagement claw, which is made of resin, and has a cantilever 326 biased toward the slider guide 56 and a protrusion 328 to be fit-engaged with the recess 324 in the surface of the cantilever 326 in contact with the slider guide 56.

The cantilever 326 has a longitudinal direction corresponding to a direction parallel with the axis of the slider guide 56 (the moving direction of the slider 54), and has a longitudinal end portion serving as a proximal end.

Thus, the position fixing mechanism 320 may also be configured such that the projection 322 is provided in the slider guide 56, and the recess 324 is formed in the slider 54.

Embodiment 9

As in Embodiment 2 illustrated in FIG. 11, a position fixing groove can also be formed in a slider guide provided with curved slider guide grooves. FIG. 39 illustrates a partial developed view of the outer circumferential surface of a slider guide 402 used in Embodiment 9.

In the slider guide 402, the four slider guide grooves 82A to 82D are formed in the same manner as in the slider guide 80 illustrated in FIG. 11, and a position fixing groove 404 connected to the forward end portion of the slider guide groove 82A to circumferentially extend by a predetermined distance is formed. The position fixing groove 404 has a width which allows fit-engagement with the slider pin 70.

By thus forming the position fixing groove 404, it is possible to fix the manipulating wire in a state of protruding from the forward end of the sheath by a given amount during the loading of the clips.

As in Embodiment 3 illustrated in FIG. 12 also, a position fixing groove can also be formed in a slider guide provided with steps. FIG. 40 illustrates a partial developed view of the outer circumferential surface of such a slider guide 406.

In the slider guide 406, the five sides 92A to 92E are formed in the same manner as in the slider guide 90 illustrated in FIG. 12, and a position fixing groove 408 connected to the side 92A to circumferentially extend by a predetermined distance is formed. The position fixing groove 408 has a width which allows fit-engagement with the slider pin 70.

By thus forming the position fixing groove 408, it is possible to fix the manipulating wire in the state of protruding from the forward end of the sheath by the given amount.

While the manipulating handle and the successive clipping device using such a manipulating handle have thus been described in detail, the present invention is not limited to the embodiments, examples, and modifications described above. Various improvements and changes may be made in the present invention without departing from the spirit thereof.

For example, in the embodiments of the clipping device described above, the three clips 12 are loaded in the single sheath, and clipping is performed three times so that the four slider guide grooves (including the three grooves corresponding to the individual clips 12, and the groove for the loading of the clips) are provided. However, the present invention is not limited thereto. It is appropriate to provide the slider guide grooves whose number is the sum of the number of the grooves corresponding to the clips to be loaded and one for the loading of the clips.

In each of Embodiments 1 to 9 described above, clipping can be performed a plurality of times at a time so that the clips are connected to each other, and connected to the single manipulating wire. However, the present invention is not limited thereto, and, though manipulating properties are degraded, individual manipulating wires may be provided for individual clips inside a single sheath, and the clips may be connected to the respective forward ends of the plurality of manipulating wires. Otherwise, though manipulating properties are further degraded, a single manipulating wire may be provided inside a single sheath, and a single clip is connected to the forward end of the manipulating wire.

In the case where a manipulating handle is not provided with a slider guide, a position fixing mechanism may be provided in a handle main body and in a slider. In this case, the groove of the handle main body may be used as a slider guide groove.

What is claimed is:

1. A manipulating handle for a successive clipping device, the manipulating handle comprising:
   a sheath;
   a manipulating wire, which is arranged in an interior of the sheath, and has a forward end to which a plurality of clips are connected;
   a cylindrical handle main body connected to the sheath, with the manipulating wire extending from the sheath being arranged in an interior thereof;
   a slider, which is attached onto an outer circumferential surface of the handle main body to be movable in an axial direction thereof, and engaged with the manipulating wire, for moving the manipulating wire in the axial direction of the handle main body; and
   a slider-movement-amount regulating member attached onto the outer circumferential surface of the handle main body so as to be rotatable in a circumferential direction of the handle main body, for regulating, according to a rotational position in a circumferential direction thereof, an amount of movement of the slider in the axial direction of the handle main body to one of a plurality of different amounts of movement required for respective clipping manipulations using the plurality of clips connected to the manipulating wire,
   wherein the slider is moved in the axial direction of the handle main body so as to move the manipulating wire arranged in the interior of the sheath in an extending direction of the sheath, to thereby move the plurality of clips connected to the manipulating wire.

2. The manipulating handle for the successive clipping device according to claim 1, wherein:
   the slider-movement-amount regulating member has a plurality of regulating portions, which correspond to the plurality of different amounts of movement, and are arranged at respective different axial positions according to circumferential positions thereof; and
   the slider has an engagement member which is engaged with one of the plurality of regulating portions selected according to the rotational position of the slider-movement-amount regulating member.

3. The manipulating handle for the successive clipping device according to claim 2, wherein:
   the handle main body has a guide groove of a predetermined length formed along the axial direction thereof; and
   the slider is movable in the axial direction in a state in which the engagement member is guided by the guide groove of the handle main body.

4. The manipulating handle for the successive clipping device according to claim 1, further comprising a position regulating member, which is fixed to the handle main body and fit-engaged with the slider-movement-amount regulating member, for regulating a position of the slider-movement-amount regulating member in at least one of a rotating direction thereof and an axial direction thereof.

5. The manipulating handle for the successive clipping device according to claim 4, wherein the position regulating member and the slider-movement-amount regulating member have, in respective contact surfaces thereof, a plurality of indented projections and recesses each formed along respective circumferential directions thereof, and the plurality of indented projections and recesses of one of the contact surfaces and the plurality of indented projections and recesses of another contact surface are caused to mesh with each other so that the position of the slider-movement-amount regulating member is regulated.

6. The manipulating handle for the successive clipping device according to claim 5, further comprising: a biasing means for biasing the contact surface of the slider-movement-amount regulating member toward the contact surface of the position regulating member.

7. The manipulating handle for the successive clipping device according to claim 5, wherein the plurality of respective projections and recesses of the position regulating member and the slider-movement-amount regulating member have shapes of saw teeth to allow the slider-movement-amount regulating member to be rotatable only in a single predetermined direction.

8. The manipulating handle for the successive clipping device according to claim 1, wherein at least a part of the slider-movement-amount regulating member is replaceable so as to differentiate, according to a type of each of the clips to be used, the amount of movement of the slider to be regulated.

9. The manipulating handle for the successive clipping device according to claim 8, further comprising:
   a single cylindrical slider guide base portion fit-engaged with the handle main body; and
   a plurality of replaceable cylindrical slider guide attachment/detachment portions corresponding to a plurality of types of the clips,
   each of the slider guide attachment/detachment portions being detachably attached to the slider guide base portion and having a plurality of regulating portions correspond to the plurality of different amounts of movement and arranged at different axial positions according to circumferential positions thereof;
   one of the plurality of slider guide detachment/attachment portions, which is selected according to the type of each of the clips to be used, and the slider guide base portion forming the slider-movement-amount regulating member.

10. The manipulating handle for the successive clipping device according to claim 9, wherein the slider has an engagement member to be engaged with one of the plurality of regulating portions which is selected according to a rotational position of the slider guide attachment/detachment portion used in the slider-movement-amount regulating member.

11. The manipulating handle for the successive clipping device according to claim 9, wherein each of the slider guide attachment/detachment portions includes a pair of substantially semicircular tubular members, the pair of substantially semicircular tubular members are combined with the handle main body interposed therebetween to provide a cylindrical shape, and a forward end portion thereof is fitted into the slider guide base portion so that the slider guide attachment/detachment portion is attached to the handle main body.

12. The manipulating handle for the successive clipping device according to claim 9, wherein the plurality of slider guide attachment/detachment portions have respective marked portions which allow visual recognition of the types of the clips corresponding thereto.

13. The manipulating handle for the successive clipping device according to claim 12, further comprising a plurality of clip cases corresponding to the plurality of types of the clips for accommodating therein the corresponding clips,
   the marked portion of the slider guide attachment/detachment portion and the clip case which correspond to the same type of clip being colored in the same color.

14. A successive clipping device comprising:
   the manipulating handle for the successive clipping device according to claim 1;
   a plurality of clips loaded in an interior of a forward end of the sheath each in a state of being engaged with another of the clips arranged in a front-rear direction; and
   a connecting member connected to the rearmost one of the plurality of clips,
   wherein a forward end of the manipulating wire is detachably connected to the connecting member in the sheath.

* * * * *